United States Patent
Zeidan et al.

(10) Patent No.: US 10,584,099 B2
(45) Date of Patent: Mar. 10, 2020

(54) MULTI-API LOADING PRODRUGS

(71) Applicant: Alkermes Pharma Ireland Limited, Dublin (IE)

(72) Inventors: Tarek A. Zeidan, Lexington, MA (US); Laura Cook Blumberg, Lincoln, MA (US)

(73) Assignee: Alkermes Pharma Ireland Limited, Dublin (IE)

(*) Notice: Subject to any disclaimer, the term of this patent is extended or adjusted under 35 U.S.C. 154(b) by 0 days.

(21) Appl. No.: 15/864,305

(22) Filed: Jan. 8, 2018

(65) Prior Publication Data

US 2018/0194732 A1    Jul. 12, 2018

Related U.S. Application Data

(63) Continuation of application No. 14/702,967, filed on May 4, 2015, which is a continuation of application No. 13/335,405, filed on Dec. 22, 2011.

(60) Provisional application No. 61/427,026, filed on Dec. 23, 2010.

(51) Int. Cl.
| | |
|---|---|
| *C07D 401/14* | (2006.01) |
| *A61K 31/496* | (2006.01) |
| *A61P 25/18* | (2006.01) |
| *C07D 215/227* | (2006.01) |
| *C07D 417/14* | (2006.01) |
| *C07D 471/04* | (2006.01) |
| *C07D 263/58* | (2006.01) |
| *C07D 277/34* | (2006.01) |
| *C07D 519/00* | (2006.01) |

(52) U.S. Cl.
CPC ....... *C07D 215/227* (2013.01); *C07D 263/58* (2013.01); *C07D 277/34* (2013.01); *C07D 401/14* (2013.01); *C07D 417/14* (2013.01); *C07D 471/04* (2013.01); *C07D 519/00* (2013.01)

(58) Field of Classification Search
CPC ............................ A61K 31/496; C07D 401/14
See application file for complete search history.

(56) References Cited

U.S. PATENT DOCUMENTS 8,431,576 B2 * 4/2013 Remenar .............. A61K 31/497
514/249

OTHER PUBLICATIONS

Andrezina et al. Current Medical Research and Opinions 2006, 22 (11), 2209-2219.*
Guarino et al. Prodrugs of amides, imides and other NH-acidic compounds. In Prodrugs: Challenges and Rewards; Stella et al., Eds.; Springer: New York, 2007; Part 1, Chapter 3.4, p. 133-187.*
Bhosle et al. Indian Journal of Pharmaceutical Sciences 2006, May-Jun., p. 286-294.*

* cited by examiner

*Primary Examiner* — Irina Neagu
(74) *Attorney, Agent, or Firm* — Elmore Patent Law Group, P.C.; Joseph Zucchero; Carolyn Elmore

(57) ABSTRACT

The present invention accomplishes this by having multiple molecules of parent drugs attached to carrier moieties and by extending the period during which the parent drug is released and absorbed after administration to the patient and providing a longer duration of action per dose than the parent drug itself. Prodrug conjugates are suitable for sustained delivery of heteroaryl, lactam-amide-, imide-, sulfonamide-, carbamate-, urea-, benzamide-, acylaniline-, cyclic amide- and tertiary amine-containing parent drugs that are substituted at the amide nitrogen or oxygen atom with labile aldehyde-linked prodrug moieties. The carrier groups of the prodrugs can be hydrophobic to reduce the polarity and solubility of the parent drug under physiological conditions.

6 Claims, No Drawings

MULTI-API LOADING PRODRUGS

RELATED APPLICATIONS

This application is a continuation of U.S. application Ser. No. 14/702,967, filed on May 4, 2015, which is a continuation of U.S. application Ser. No. 13/335,405, filed Dec. 22, 2011, now abandoned, which claims the benefit of U.S. Provisional Application No. 61/427,026, filed on Dec. 23, 2010. The entire teachings of the above applications are incorporated herein by reference.

FIELD OF THE INVENTION

The present invention relates to prodrugs that can be linked to multiple drug molecules.

BACKGROUND OF THE INVENTION

Drug delivery systems are often critical for the safe and effective administration of a biologically active agent. Perhaps the importance of these systems is best realized when patient compliance and consistent dosing are taken under consideration. For instance, reducing the dosing requirement for a drug from four-times-a-day to a single dose per day would have significant value in terms of ensuring patient compliance and optimizing therapy. Many of the currently administered prodrugs and formulations require large amounts of drug/excipient/prodrug mixtures for administration.

Optimization of a drug's bioavailability has many potential benefits. For patient convenience and enhanced compliance it is generally recognized that less frequent dosing is desirable. By extending the period through which the drug is released, a longer duration of action per dose is expected. This will then lead to an overall improvement of dosing parameters such as taking a drug once a day where it has previously required four doses per day or dosing once a week or even less frequently when daily dosing was previously required. Many drugs are presently dosed once per day, but not all of these drugs have pharmacokinetic properties that are suitable for dosing intervals of exactly twenty-four hours. Extending the period through which these drugs are released would also be beneficial.

One of the fundamental considerations in drug therapy involves the relationship between blood levels and therapeutic activity. For most drugs, it is of primary importance that serum levels remain between a minimally effective concentration and a potentially toxic level. In pharmacokinetic terms, the peaks and troughs of a drug's blood levels ideally fit well within the therapeutic window of serum concentrations. For certain therapeutic agents, this window is so narrow that dosage formulation becomes critical.

In an attempt to address the need for improved bioavailability, several drug release modulation technologies have been developed. For example, poorly soluble 5,5-diphenylimidazolidine-2,4-diones have been derivatized into phosphate ester prodrugs to improve solubility (Stella et al., U.S. Pat. No. 4,260,769, 1981). Enteric coatings have been used as a protector of pharmaceuticals in the stomach and microencapsulating active agents using proteinaceous microspheres, liposomes or polysaccharides have been effective in abating enzymatic degradation of the active agent. Enzyme inhibiting adjuvants have also been used to prevent enzymatic degradation.

A wide range of pharmaceutical formulations provide sustained release through microencapsulation of the active agent in amides of dicarboxylic acids, modified amino acids or thermally condensed amino acids. Slow release rendering additives can also be intermixed with a large array of active agents in tablet formulations. Many of these formulations, however, deliver relatively low amounts of parent drugs in comparison with the overall weight of the formulations.

While microencapsulation and enteric coating technologies impart enhanced stability and time-release properties to active agent substances these technologies suffer from several shortcomings. Incorporation of the active agent is often dependent on diffusion into the microencapsulating matrix, which may not be quantitative and may complicate dosage reproducibility. In addition, encapsulated drugs rely on diffusion out of the matrix or degradation of the matrix, or both, which is highly dependent on the chemical properties and water solubility of the active agent. Conversely, water-soluble microspheres swell by an infinite degree and, unfortunately, may release the active agent in bursts with limited active agent available for sustained release. Furthermore, in some technologies, control of the degradation process required for active agent release is unreliable. For example, because an enterically coated active agent depends on pH to release the active agent and pH and residence time varies, the release rate is difficult to control.

Several implantable drug delivery systems have utilized polypeptide attachment to drugs. Additionally, other large polymeric carriers incorporating drugs into their matrices are used as implants for the gradual release of drugs. Yet another technology combines the advantages of covalent drug attachment with liposome formation where the active ingredient is attached to highly ordered lipid films.

There is a generally recognized need for sustained delivery of drugs that reduces the daily dosing requirement and allows for controlled and sustained release of the parent drug and also avoids irregularities of release and cumbersome formulations encountered with typical dissolution controlled sustained release methods. Furthermore, there is a need to accomplish the above listed goals with high relative ratios of parent drugs in relation to the dry weight of the formulation.

SUMMARY OF THE INVENTION

The present invention accomplishes this by having multiple molecules of parent drugs attached to carrier moieties and by extending the period during which the parent drug is released and absorbed after administration to the patient and providing a longer duration of action per dose than the parent drug itself. In one embodiment, the compounds suitable for use in the methods of the invention are derivatives of heteroaryl, lactam-, amide-, imide-, sulfonamide-, carbamate-, urea-, benzamide-, N-acylaniline-, and cyclic amide-, and tertiary amine containing parent drugs that are substituted at a nitrogen or oxygen atom with a labile aldehyde-linked prodrug moieties. In one embodiment, the prodrug moieties are hydrophobic and reduce the polarity and solubility of the parent drug under physiological conditions.

In one embodiment, the invention provides a prodrug compound of Formula I, IA or IB:

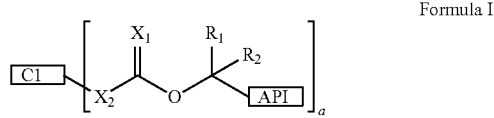

Formula I

-continued

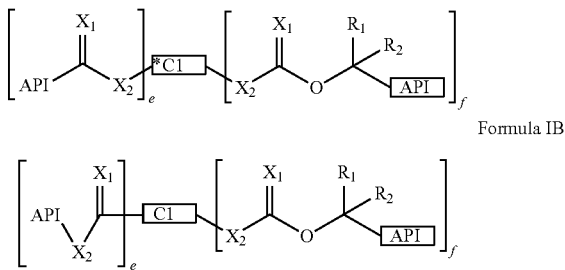

Formula IA

Formula IB wherein a is 2, 3, 4, 5, 6, 7, 8, 9, 10, 11, 12, 13, 14, 15 or 16;

e is selected from 1, 2, 3, 4, 5, 6, 7, 8, 9, 10, 11, 12, 13, 14, 15 or 16;

f is selected from 0, 1, 2, 3, 4, 5, 6, 7, 8, 9, 10, 11, 12, 13, 14, 15 or 16, wherein the sum of e and f is at least two;

each $R_1$ and $R_2$ is independently selected hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl and optionally substituted heterocyclyl;

wherein each $R_{20}$ and $R_{21}$ is independently selected from hydrogen, halogen, aliphatic, substituted aliphatic, aryl and substituted aryl;

$X_1$ is selected from O or S;

$X_2$ is selected from direct bond, O, S or $NR_{20}$;

C1 is a carrier moiety; and each API is independently a biologically active moiety.

The invention further relates to prodrugs of secondary amine containing drugs of Formula LI:

Formula LI

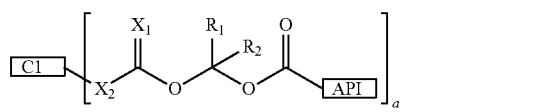

In one embodiment, each API is the same biologically active moiety. In another embodiment, the API groups represent two or more different biologically active moieties.

The invention further provides a method for sustained delivery of a parent drug by the administration of a conjugate of the parent drug with a labile moiety, wherein the conjugate is represented by Formula I, IA or IB.

DETAILED DESCRIPTION OF THE INVENTION

The present provides a method for attaching multiple parent drugs (biologically active moieties) to a carrier moiety resulting in a conjugate that can undergo spontaneous or enzyme assisted cleavage in physiological conditions to release the parent drug. In one embodiment, the release of the parent drug is sustained release. The sustained release is accomplished by extending the period during which the parent drug is released and absorbed after administration to the patient and providing a longer duration of action per dose than the parent drug itself. In one embodiment, the prodrug moieties are hydrophobic and reduce the polarity and solubility of the parent drug under physiological conditions.

One of the challenges for delivering a prodrug is the high amount of prodrug needed to be dosed compared to the parent drug due to the higher molecular weight of the prodrug compared to the parent drug. Having a multivalent carrier moiety that can link two or more parent drug moieties can decrease the dose load. Also, such a multivalent carrier can link two different APIs. For example, molecules of Aripiprazole and Dehydroaripiprazole can be linked to the same carrier moiety. In another embodiment, two molecules can be linked to the same carrier so that they will be released through different mechanisms. For example, a quaternary ammonium prodrug can easily hydrolyze in physiological conditions. On the other hand, a parent drug linked through another functional group that relies on enzymatic action might release more slowly. Thus, two parent drugs can be linked to a single carrier moiety, the first via a quaternary ammonium group on one end and the second through a labile functional group. This allows one to tailor the release of the two parent drugs, with faster delivery of one parent drug compared to the other based on chemical reactivity and/or enzymatic activity.

In one embodiment, the invention provides a prodrug compound of Formula I, IA or IB:

Formula I

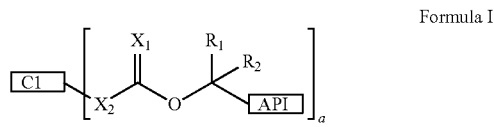

Formula IA

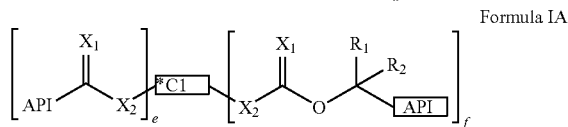

Formula IB

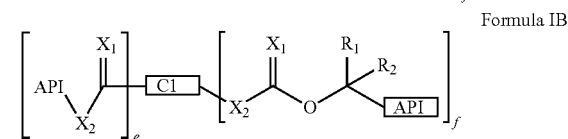

wherein a is 2, 3, 4, 5, 6, 7, 8, 9, 10, 11, 12, 13, 14, 15 or 16;

e is selected from 1, 2, 3, 4, 5, 6, 7, 8, 9, 10, 11, 12, 13, 14, 15 or 16;

f is selected from 0, 1, 2, 3, 4, 5, 6, 7, 8, 9, 10, 11, 12, 13, 14, 15 or 16, wherein the sum of e and f is at least two;

each $R_1$ and $R_2$ is independently selected hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl and optionally substituted heterocyclyl;

wherein each $R_{20}$ and $R_{21}$ is independently selected from hydrogen, halogen, aliphatic, substituted aliphatic, aryl and substituted aryl;

$X_1$ is selected from O or S;

$X_2$ is selected from direct bond, O, S or $NR_{20}$;

C1 is a carrier; and each API is independently a biologically active moiety.

The invention further relates to prodrugs of secondary amine containing drugs of Formula LI:

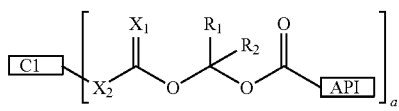

Formula LI

The invention further provides a method for sustained delivery of a parent drug by the administration of a multivalent conjugate of the parent drug with a labile moiety, wherein the conjugate is represented by Formula I, IA, IB or LI.

In some embodiments, C1 is selected from optionally substituted aliphatic, aryl or substituted aryl. In some embodiments, C1 is selected from optionally substituted $C_1$-$C_{30}$ alkyl, optionally substituted $C_2$-$C_{30}$ alkenyl, optionally substituted $C_1$-$C_{30}$ alkynyl, optionally substituted $C_1$-$C_{30}$ aryl. In some embodiments, C1 is selected from optionally substituted bicyclic heteroaryl group selected from benzofuran, benzothiophene, indole, benzimidazole, indazole, benzotriazole, pyrrolo[2,3]pyridine, imidazopyridine, pyrazolopyridine, isoindole, quinoline, isoquinoline, quinazoline, quinoxaline, phthalazine, indazole, purine, indolizine, indole, indoline, isoindoline, benzofuran and chromene. In some embodiments, C1 is a polyethyleneglycol group having a molecular weight of about 400 dalton to about 100,000 dalton.

In some embodiments, C1 is selected from:

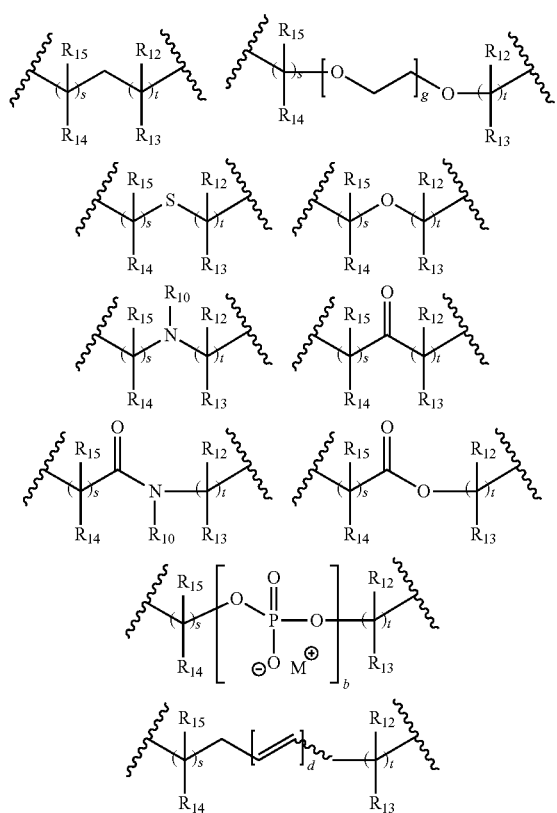

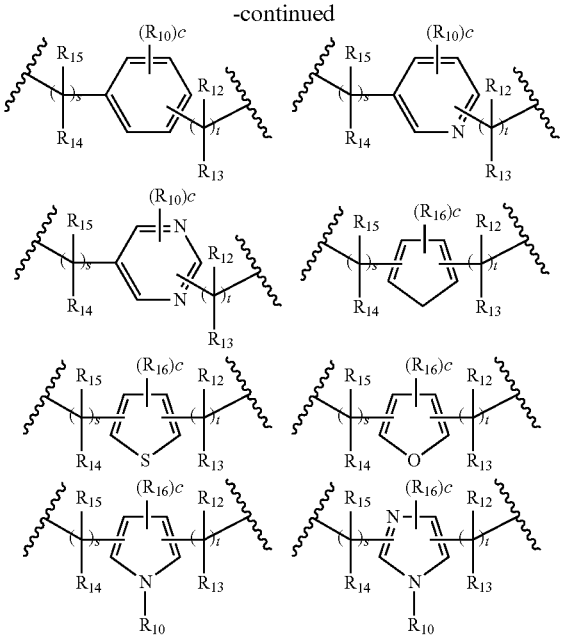

wherein
c is selected from 0, 1, 2, 3 and 4;
g is an integer from 1 to about 1,000;
each b and d is independently selected from 0, 1, 2, 3, 4, 5, 6, 7, 8, 9, 10, 11, 12 and 13;
s and t are each independently selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30;
each $R_{10}$, $R_{11}$, $R_{12}$, $R_{13}$, $R_{14}$, $R_{15}$, and $R_{16}$ is independently selected from absent, hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl and optionally substituted heterocyclyl;
wherein each $R_{20}$ and $R_{21}$ is independently selected from hydrogen, halogen, aliphatic, substituted aliphatic, aryl and substituted aryl;
alternatively two $R_{10}$, $R_{11}$, $R_{12}$, $R_{13}$, $R_{14}$, $R_{15}$, and $R_{16}$ together with the atoms to which they are attached may form an optionally substituted 3, 4, 5, 6 or 7 membered carbocyclic or heterocyclyl ring.

In some embodiments, C1 is a dendrimer.
In some embodiments, the invention relates to a prodrug conjugate of Formula II:

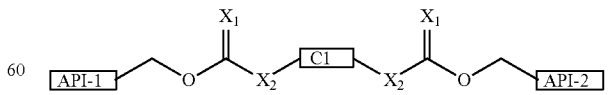

Formula II wherein, each $X_1$ is independently selected from S or O;
each $X_2$ is selected from absent, O, S or $NR_{20}$ wherein $R_{20}$ is selected from hydrogen, halogen, aliphatic, substituted aliphatic, aryl or substituted aryl;
API-1 is a biologically active moiety; and API-2 is a biologically active moiety and is the same or different from API-1.

In some embodiments, the invention relates to a prodrug conjugate having the formula:

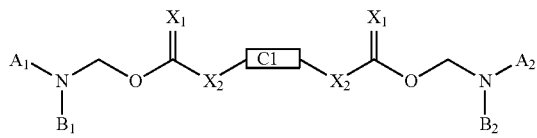

wherein $A_1$ and $B_1$ together with the nitrogen they are attached to form a first biologically active molecule; and, $A_2$ and $B_2$ together with the nitrogen they are attached to form a second biologically active molecule.

In some embodiments, the invention relates to a prodrug conjugate having the formula:

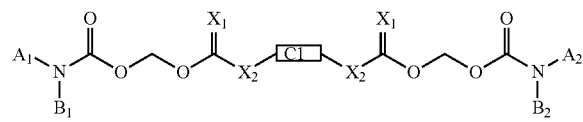

wherein $A_1$ and $B_1$ together with the nitrogen they are attached to form a first biologically active molecule; and, $A_2$ and $B_2$ together with the nitrogen they are attached to form a second biologically active molecule.

In some embodiments, the invention relates to a prodrug conjugate having the formula:

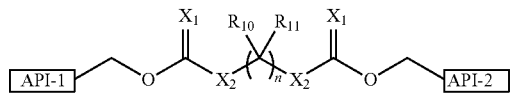

wherein n is an integer between about 1 and about 50; each $R_{10}$ and $R_{11}$ is independently selected from absent, hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl; wherein each $R_{20}$ and $R_{21}$ is selected from hydrogen, halogen, aliphatic, substituted aliphatic, aryl or substituted aryl;
alternatively two $R_{10}$ and $R_{11}$ together with the atoms to which they are attached may form an optionally substituted 3, 4, 5, 6 or 7 membered carbocyclic or heterocyclyl ring.

In some embodiments, the invention relates to a prodrug of a secondary amine containing parent drug having the formula:

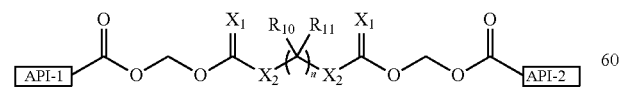

wherein n is an integer between about 1 and about 50; each $R_{10}$ and $R_{11}$ is independently selected from absent, hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl;
wherein each $R_{20}$ and $R_{21}$ is selected from hydrogen, halogen, aliphatic, substituted aliphatic, aryl or substituted aryl; alternatively two $R_{10}$ and $R_{11}$ together with the atoms to which they are attached may form an optionally substituted 3, 4, 5, 6 or 7 membered carbocyclic or heterocyclyl ring.

In a preferred embodiment, n is an integer between about 4 and about 26.

In some embodiments, the invention relates to a prodrug conjugate with three drug moieties attached to a carrier group. For example, three parent drug moieties can be attached to an aconitic acid based carrier:

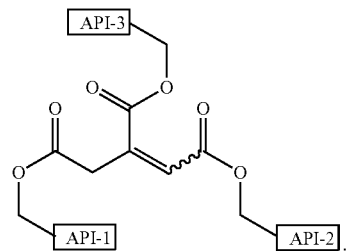 [SMILES: CCOC(=O)C=C(CC(=O)OCC)C(=O)OCC]

Other tricarboxylic acid compounds such as citric acid, isocitric acid, and trimesic acid can be used as carriers. In one embodiment, the invention relates to prodrugs having the formula:

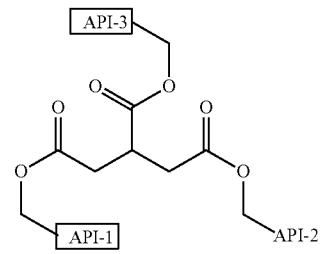

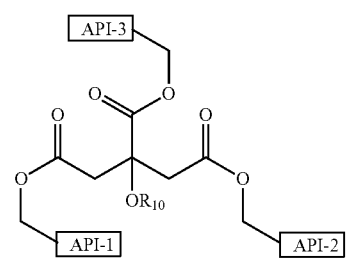

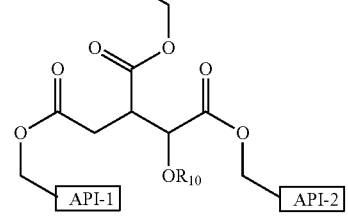

-continued

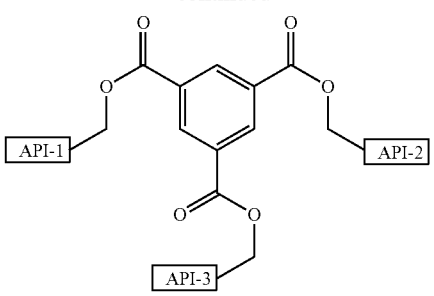

API-1 and API-2 are as defined above, and API-3 is a biologically active moiety and is the same or different from API-1, and API-2.

Prodrugs of Lactam, Cyclic Urea, Imide and Carbamate Containing Pharmacophores

In one embodiment, the compounds of the invention are derivatives of lactam-, imide-, carbamate-, and cyclic urea-, -containing parent drugs that are substituted at the amide nitrogen or oxygen atom with labile aldehyde-linked prodrug moieties.

In some embodiments, the invention relates to a prodrug conjugate having the formula:

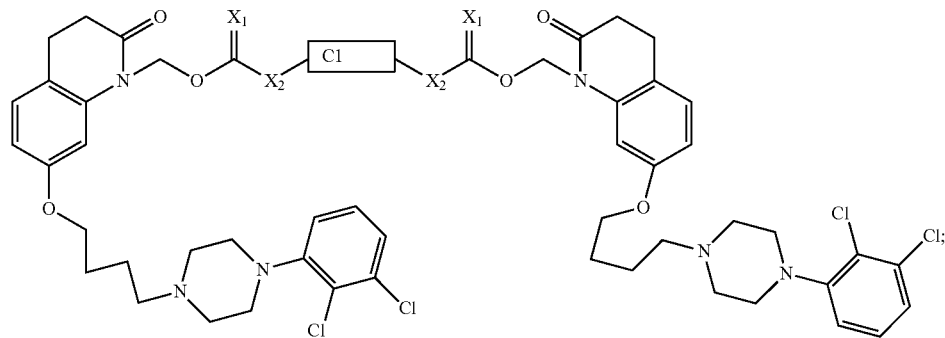

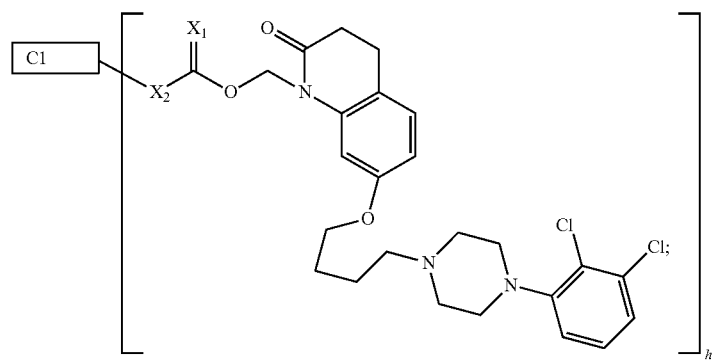

wherein h is 3 or 4;

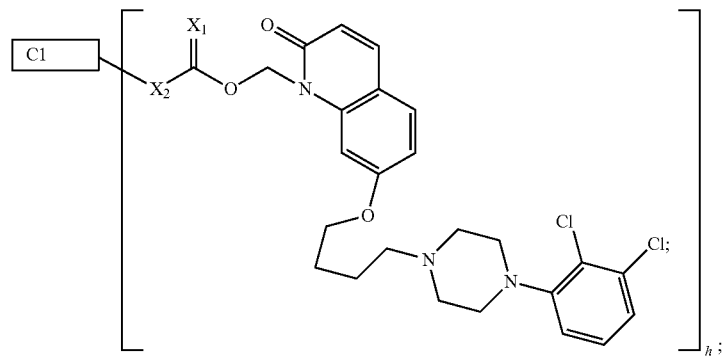

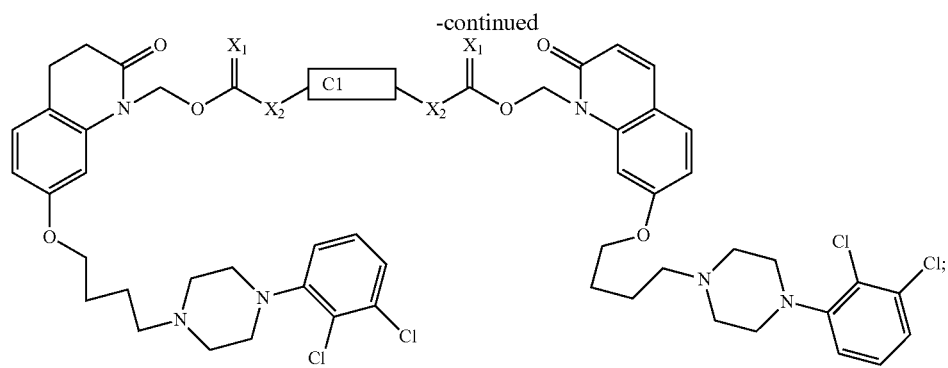
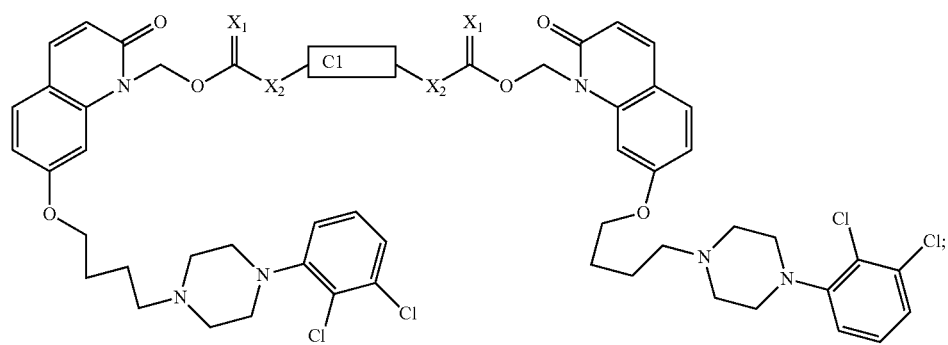
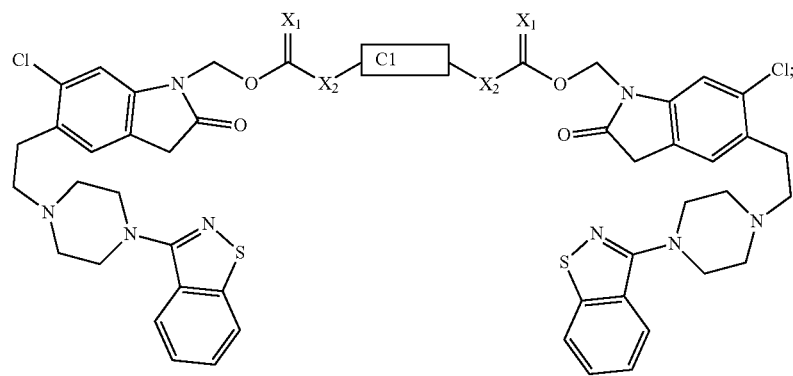

-continued
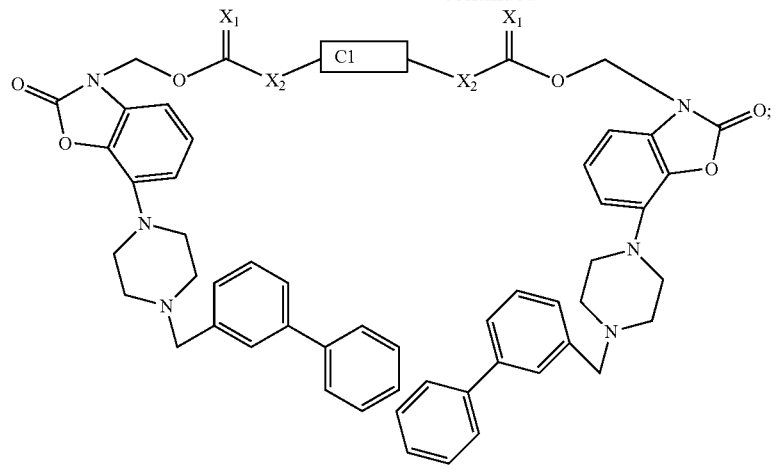
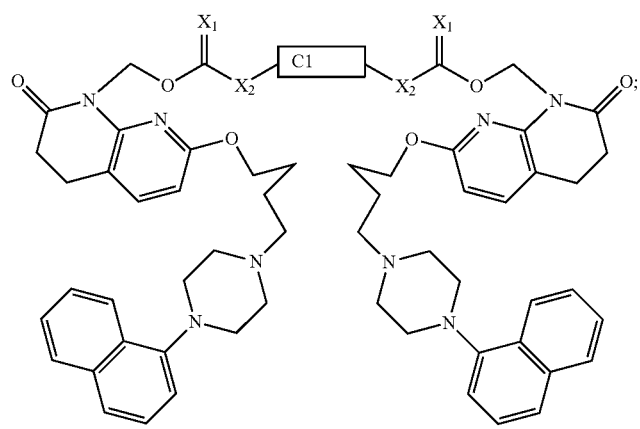
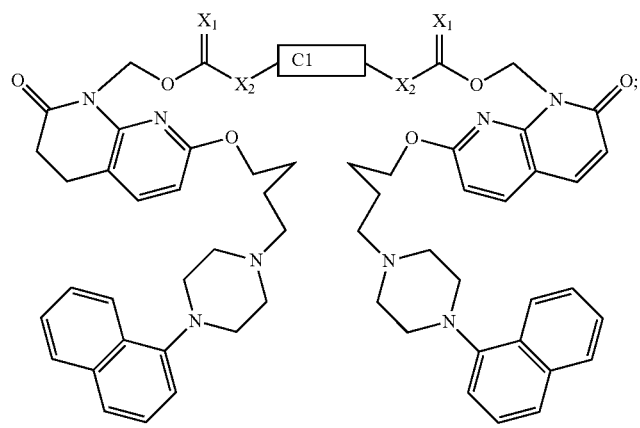

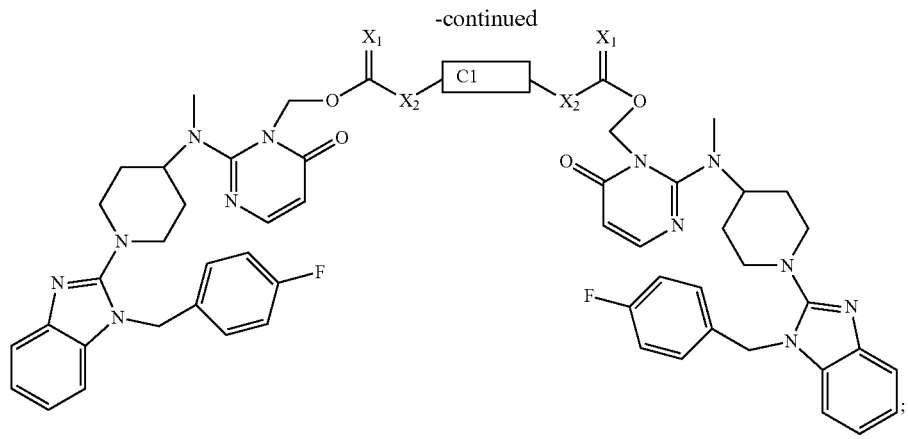

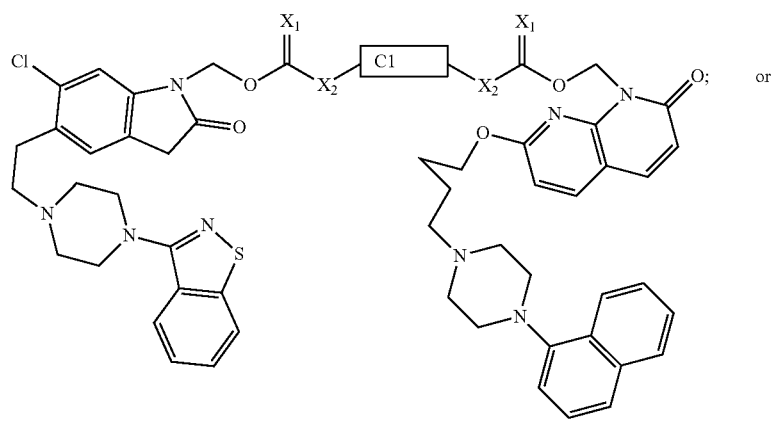

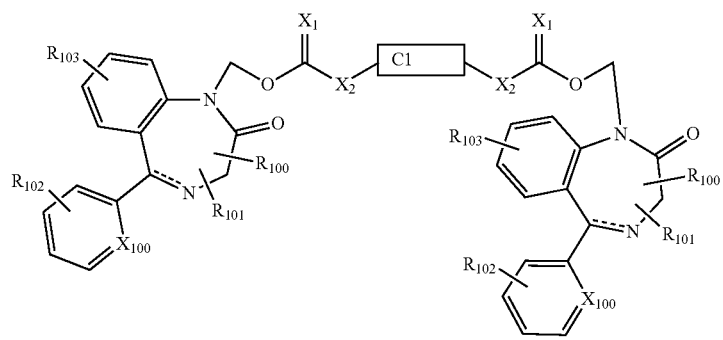

wherein each $R_{100}$, $R_{101}$, $R_{102}$, and $R_{103}$ is independently selected from absent, hydrogen, halogen, —$OR_{10}$, —$SR_{10}$, —$NR_{10}R_{11}$—, optionally substituted aliphatic, optionally substituted aryl or optionally substituted heterocyclyl; alternatively, two $R_{100}$, and $R_{101}$ together form an optionally substituted carbocyclic or heterocyclyl ring;

C1 is as previously defined; and, $X_{100}$ is —CH— or —N—.

In some embodiments, the invention relates to a prodrug conjugates having the formula:

wherein D together with oxygen to which it is attached forms a biologically active moiety; and, $D_2$ together with oxygen to which it is attached forms a biologically active moiety; and C1 is as previously defined.

In some embodiments, the invention relates to a prodrug conjugate having the formula:

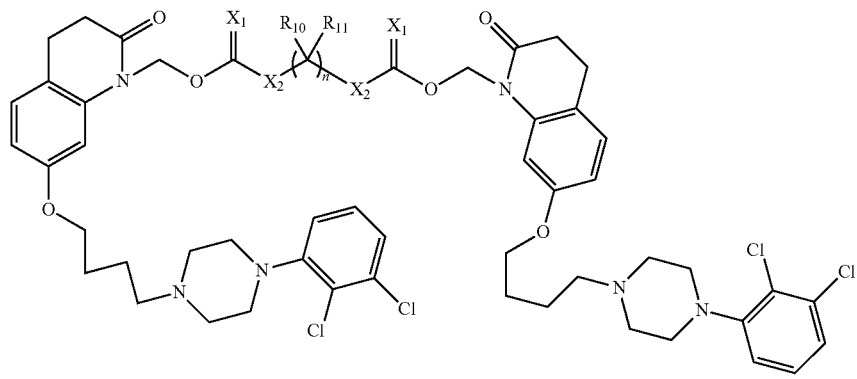
wherein n is selected from 4, 5, 6, 7, 8, 9, 10, 11, 12, 13, 14, 15, 16, 17, 18, 19, 20, 21, 22, 23, 24, 25, 26, 27, 28, 29 and 30.
In one embodiment, the parent drug moieties (APIs) are selected from Table 1. In one embodiment, the prodrug is a compound of Formula II wherein API-1 and API-2 are selected from Table-1. In one embodiment both API-1 and API-2 represent the same parent drug.
TABLE 1
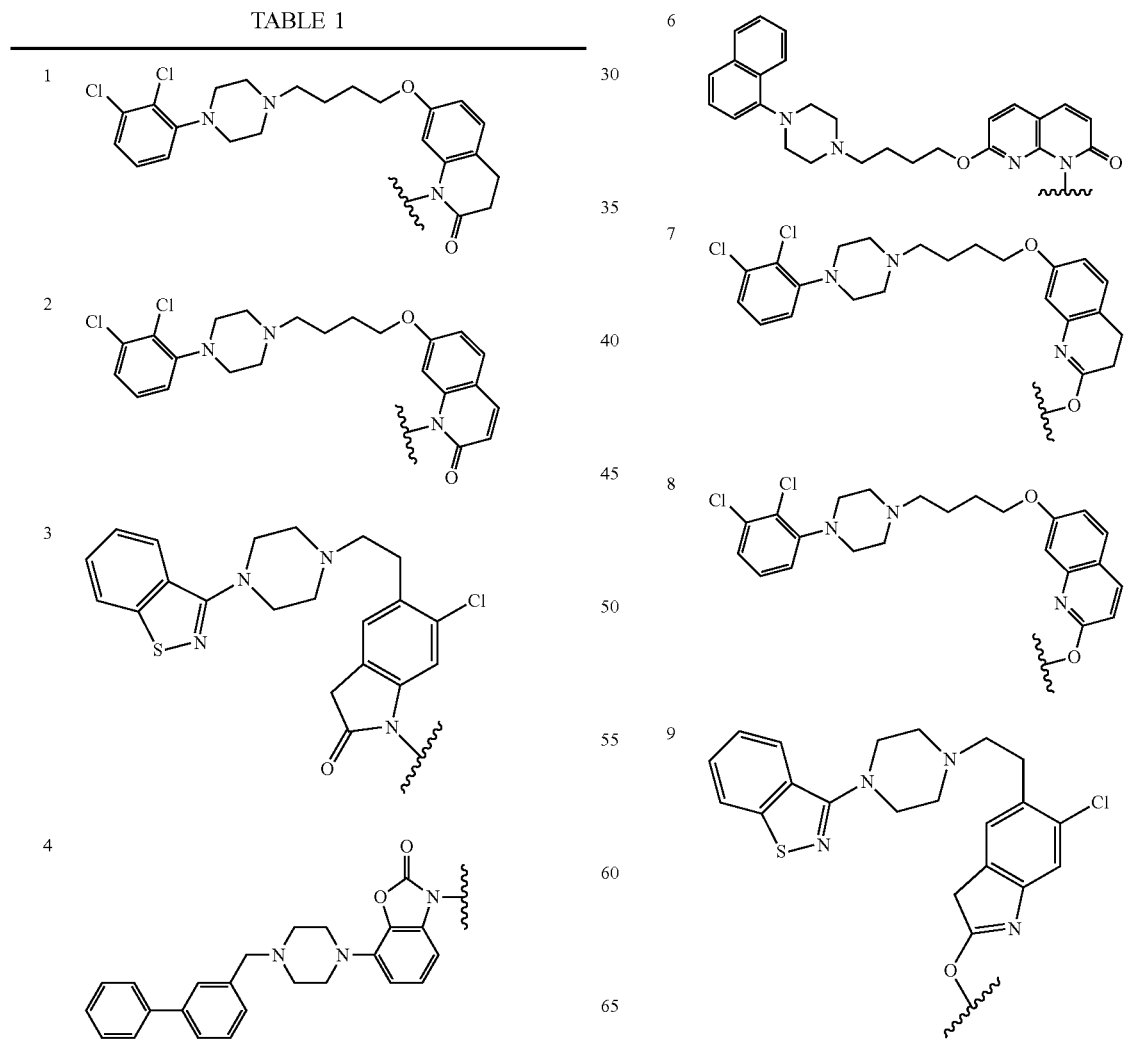

TABLE 1-continued
10 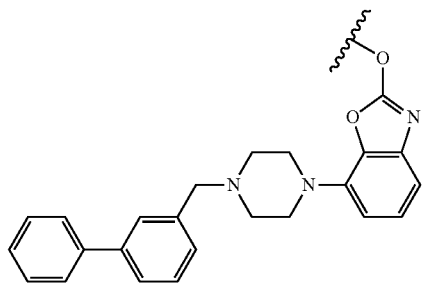 [SMILES: *Oc1nc2cccc(N3CCN(Cc4cccc(-c5ccccc5)c4)CC3)c2o1]
11 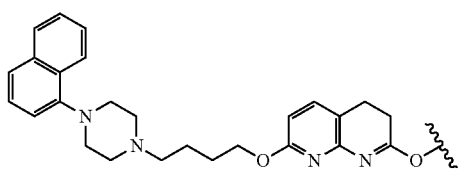 [SMILES: *OC1=Nc2nc(OCCCCN3CCN(c4cccc5ccccc45)CC3)ccc2CC1]
12 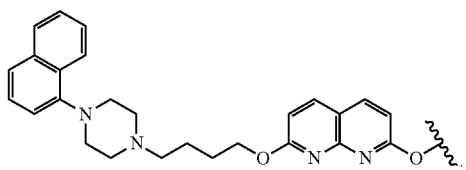 [SMILES: *Oc1ccc2ccc(OCCCCN3CCN(c4cccc5ccccc45)CC3)nc2n1]
In one embodiment, the parent drug moieties (APIs), are selected from Table 2. In one embodiment, the prodrug is a compound of Formula II wherein API-1 and API-2 are selected from Table-2. In one embodiment both API-1 and API-2 represent the same parent drug.
TABLE 2
1 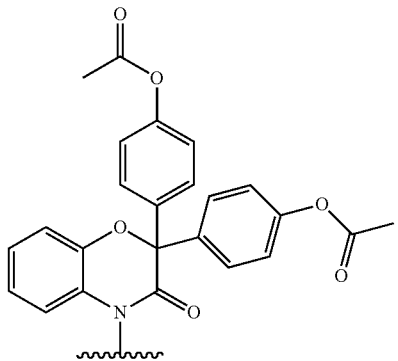 [SMILES: *N1C(=O)C(c2ccc(OC(C)=O)cc2)(c2ccc(OC(C)=O)cc2)Oc2ccccc21]
2 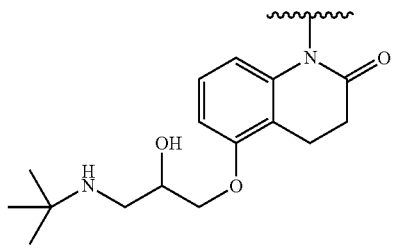 [SMILES: *N1C(=O)CCc2c(OCC(O)CNC(C)(C)C)cccc21]
3 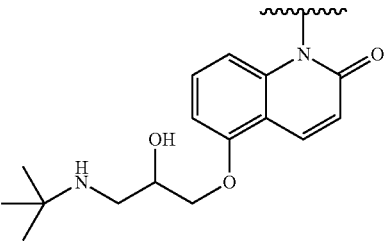 [SMILES: *n1c(=O)ccc2c(OCC(O)CNC(C)(C)C)cccc21]
4 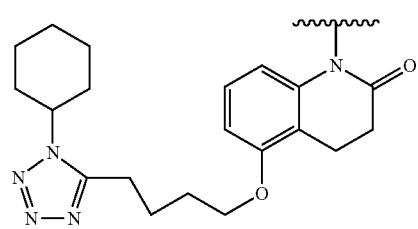 [SMILES: *N1C(=O)CCc2c(OCCCCc3nnnn3C3CCCCC3)cccc21]
5 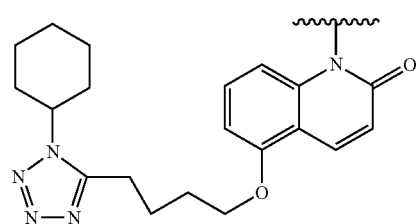 [SMILES: *n1c(=O)ccc2c(OCCCCc3nnnn3C3CCCCC3)cccc21]
6 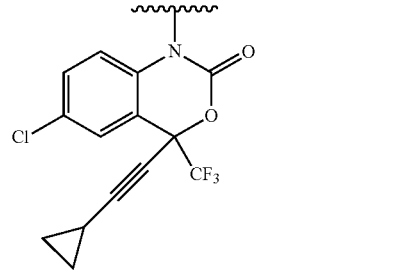 [SMILES: *N1C(=O)OC(C#CC2CC2)(C(F)(F)F)c2cc(Cl)ccc21]
7 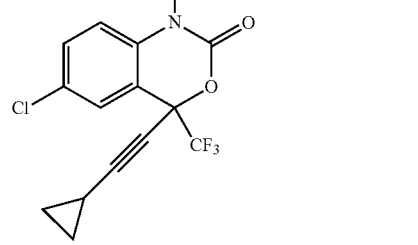

TABLE 2-continued
| 8 | 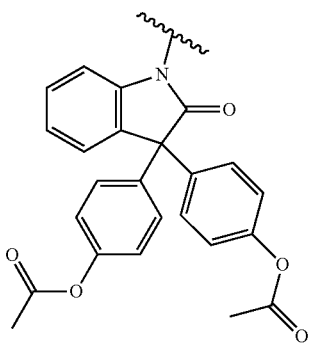 [SMILES: *N1C(=O)C(c2ccc(OC(C)=O)cc2)(c2ccc(OC(C)=O)cc2)c2ccccc21] |
| --- | --- |
| 9 | 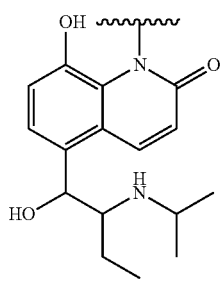 |
| 10 | 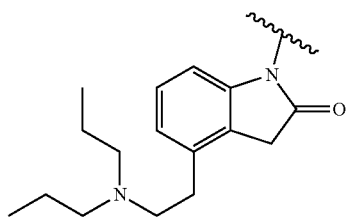 [SMILES: *N1C(=O)Cc2c(CCN(CCC)CCC)cccc21] |
| 11 | 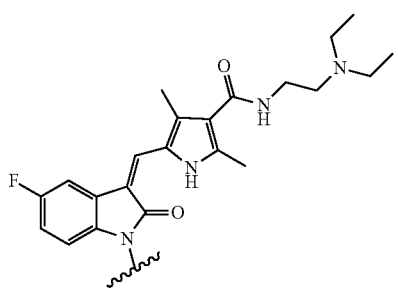 [SMILES: *N1C(=O)/C(=C\c2[nH]c(C)c(C(=O)NCCN(CC)CC)c2C)c2cc(F)ccc21] |
| 12 | 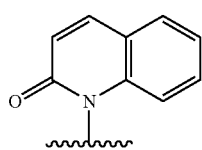 [SMILES: *n1c(=O)ccc2ccccc21] |
| 13 | 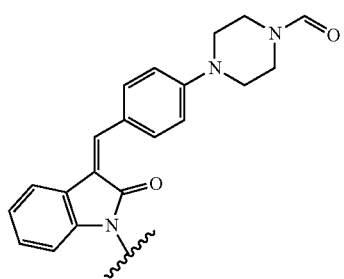 [SMILES: *N1C(=O)/C(=C\c2ccc(N3CCN(C=O)CC3)cc2)c2ccccc21] |
TABLE 2-continued
| 14 | 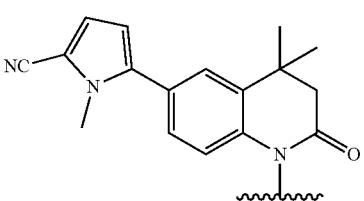 |
| --- | --- |
| 15 | 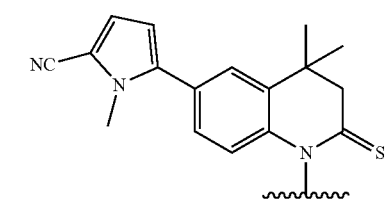 [SMILES: *N1C(=O)CC(C)(C)c2cc(-c3ccc(C#N)n3C)ccc21] |
| 16 | 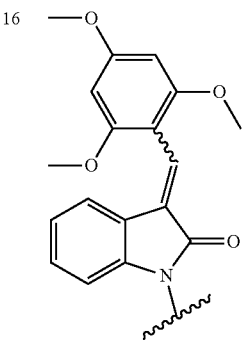 |
| 17 | 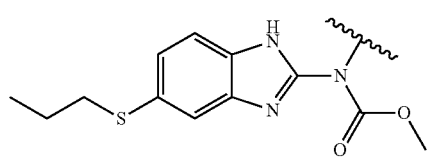 [SMILES: *N(C(=O)OC)c1nc2cc(SCCC)ccc2[nH]1] |
| 18 | 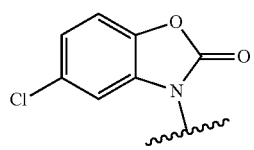 [SMILES: *n1c(=O)oc2ccc(Cl)cc21] |
| 19 | 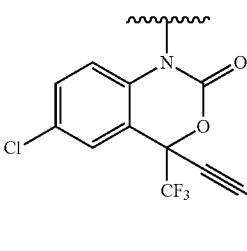 |
| 20 | 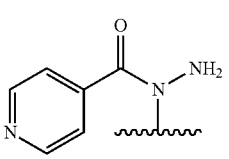 |

TABLE 2-continued
21
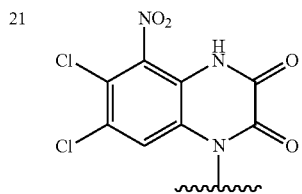
22
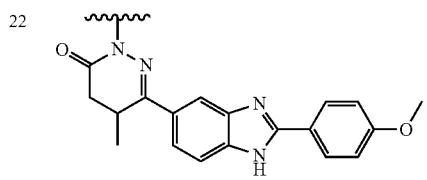
23
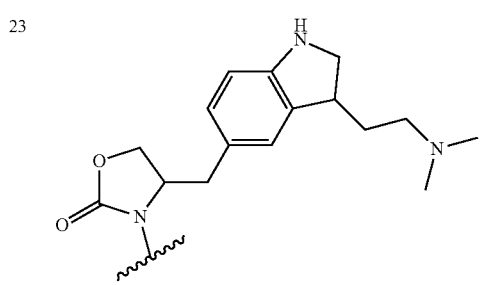
24
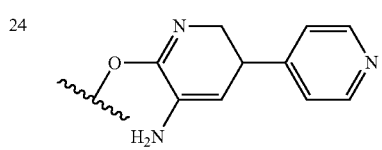
25
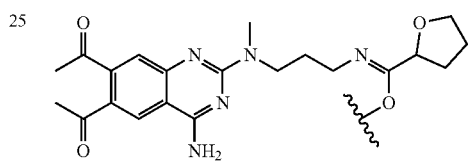
26
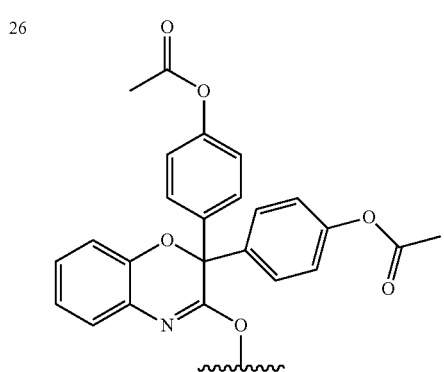
27
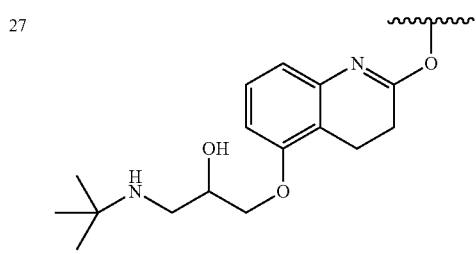
TABLE 2-continued
28
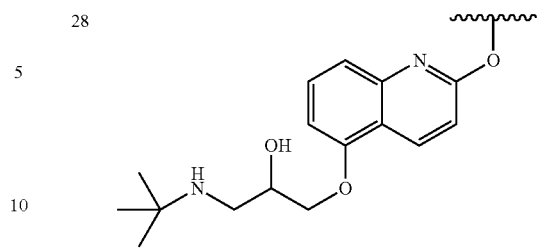
29
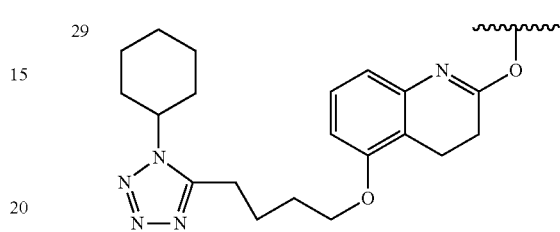
30
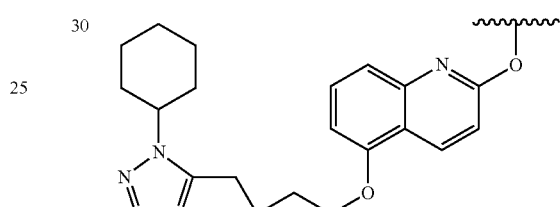
31
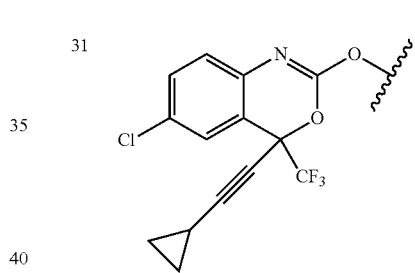
32
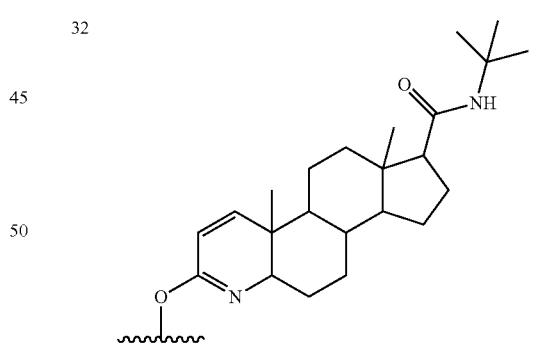
33
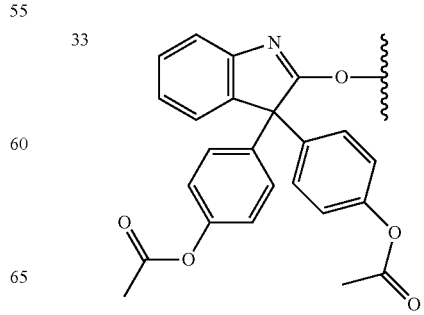

TABLE 2-continued
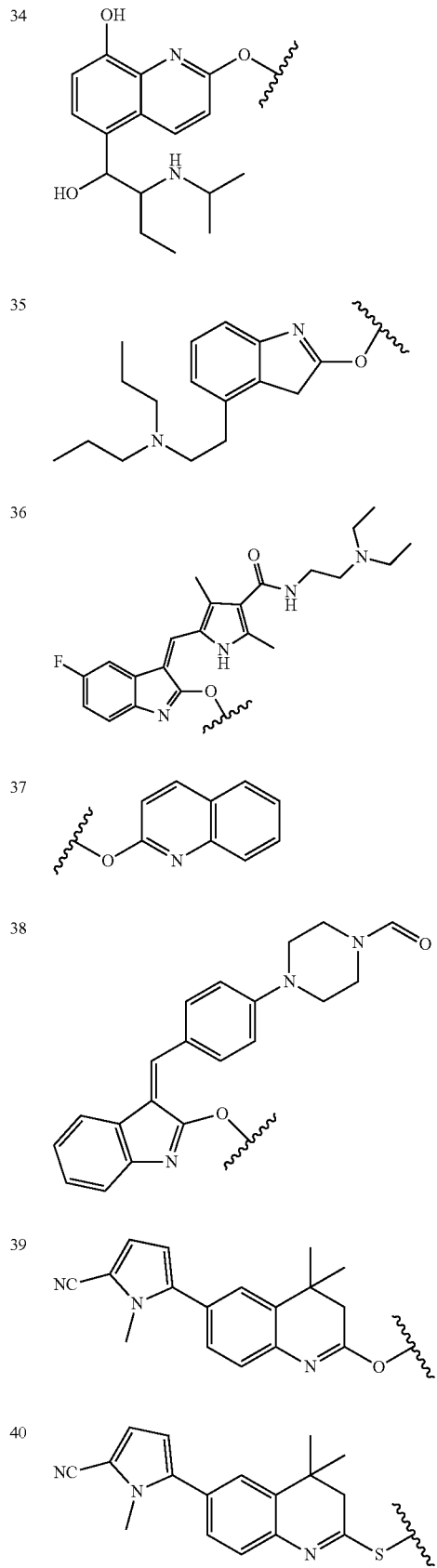
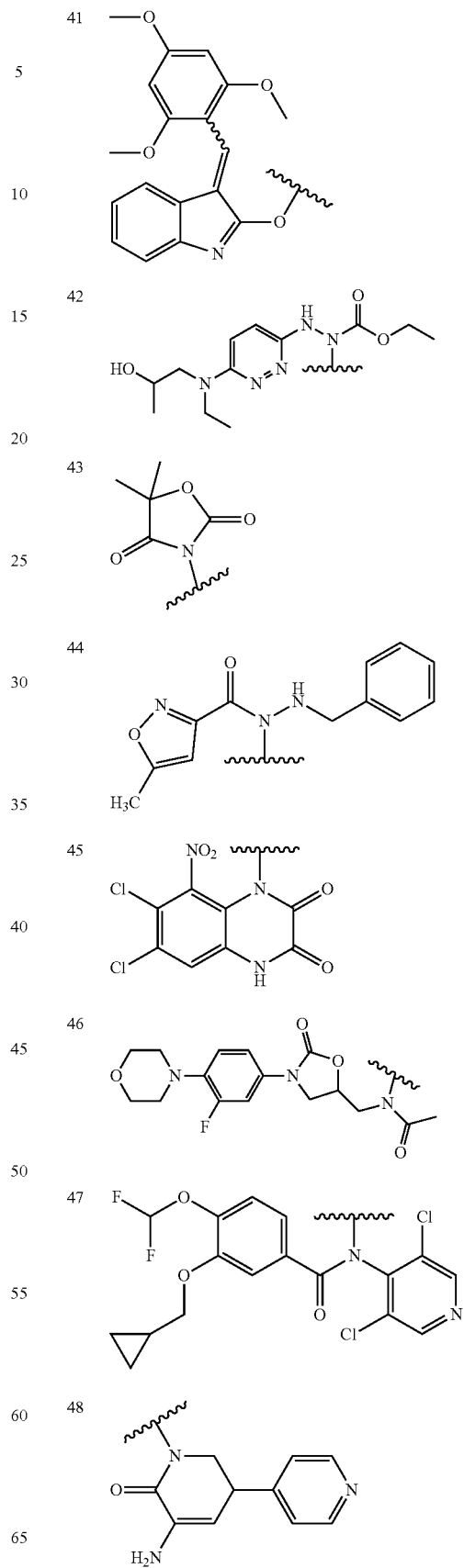

TABLE 2-continued
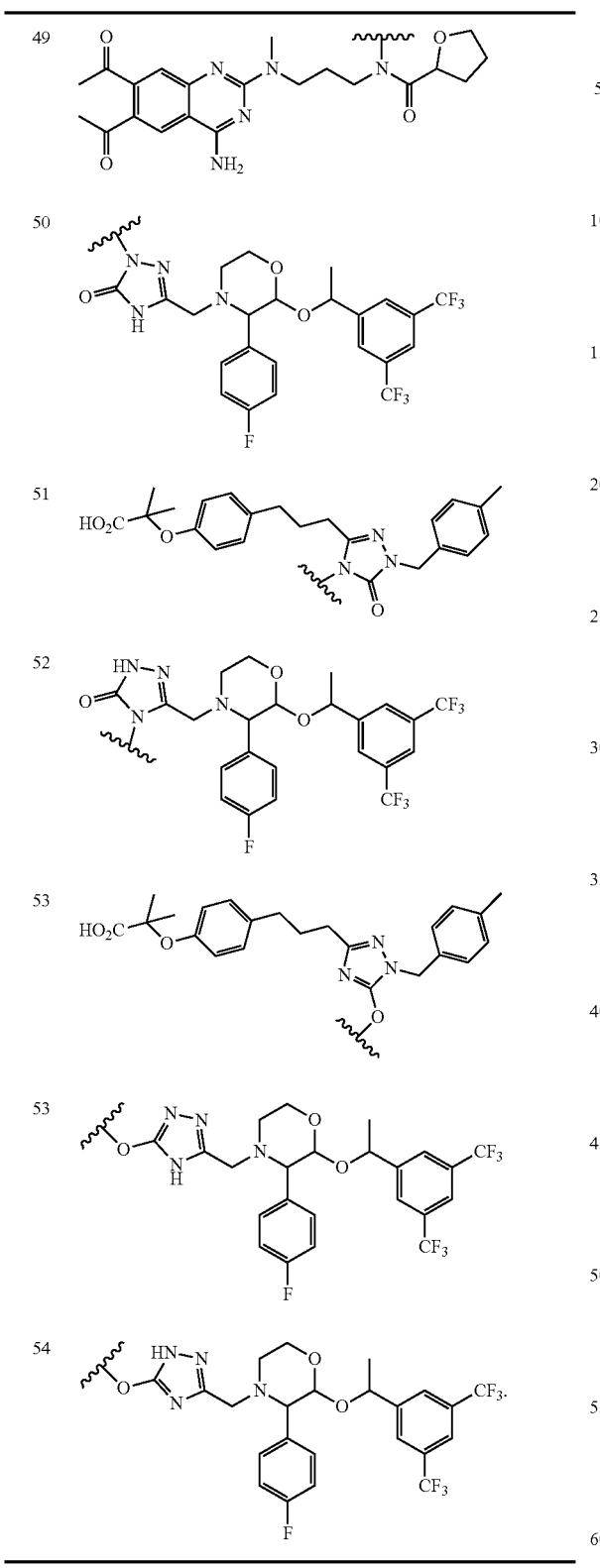
TABLE 3
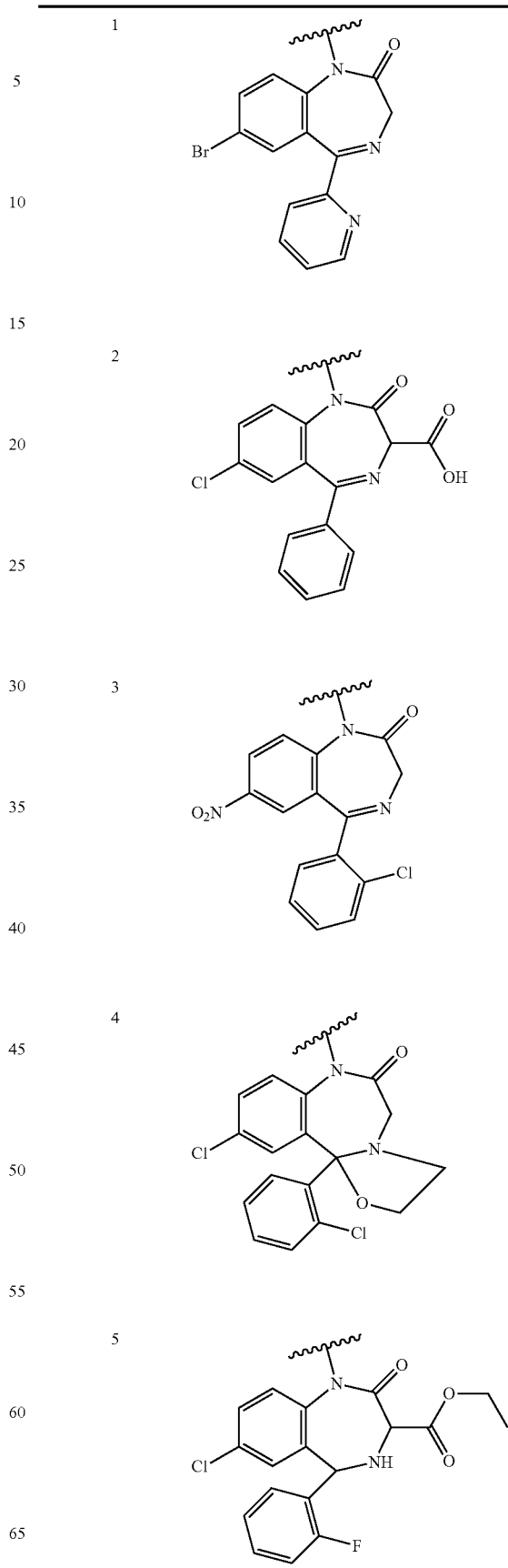
In one embodiment, the parent drug moieties (APIs) are selected from Table 3. In one embodiment, the prodrug is a compound of Formula II wherein API-1 and API-2 are selected from Table 3. In one embodiment both API-1 and API-2 represent the same parent drug.

TABLE 3-continued
| | | | | |
|---|---|---|---|---|
| 6 | 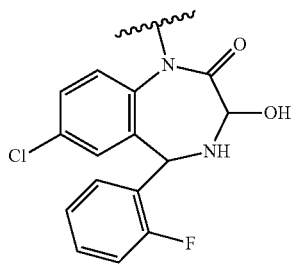 [SMILES: *N1C(=O)C(O)NC(c2ccccc2F)c2cc(Cl)ccc21] | | 11 | 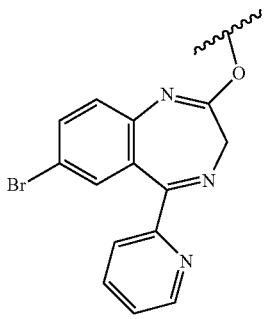 |
| 7 | 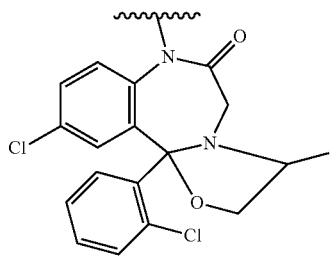 [SMILES: *N1C(=O)CN2C(C)COC2(c2ccccc2Cl)c2cc(Cl)ccc21] | | 12 | 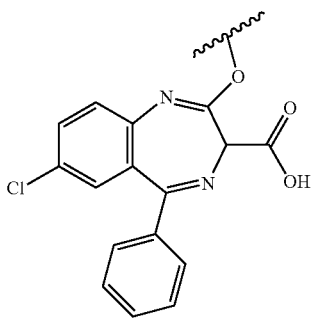 |
| 8 | 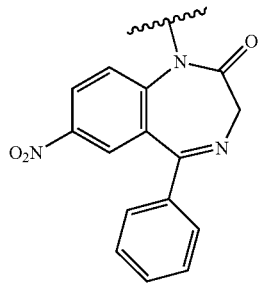 [SMILES: *N1C(=O)CN=C(c2ccccc2)c2cc([N+](=O)[O-])ccc21] | | 13 | 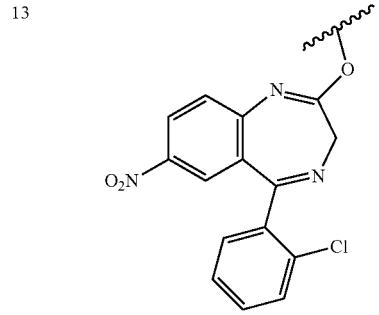 |
| 9 | 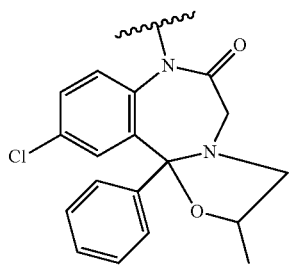 [SMILES: *N1C(=O)CN2CC(C)OC2(c2ccccc2)c2cc(Cl)ccc21] | | 14 | 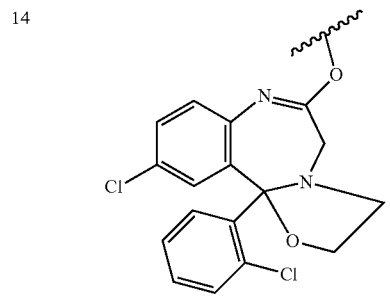 |
| 10 | 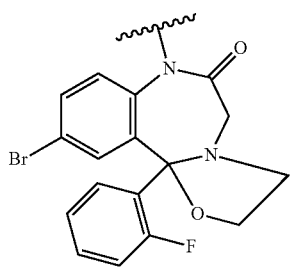 [SMILES: *N1C(=O)CN2CCOC2(c2ccccc2F)c2cc(Br)ccc21] | | 15 | 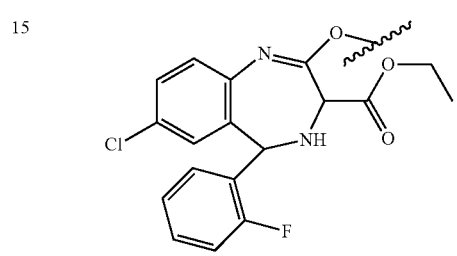 |

TABLE 3-continued

16
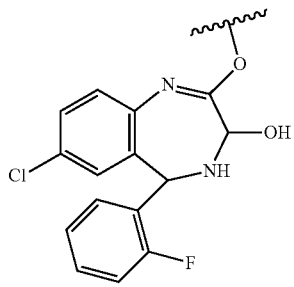 [SMILES: *OC1=Nc2ccc(Cl)cc2C(c2ccccc2F)NC1O]

17
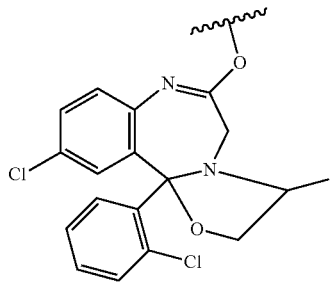 [SMILES: *OC1=Nc2ccc(Cl)cc2C2(c3ccccc3Cl)OCC(C)N2C1]

18
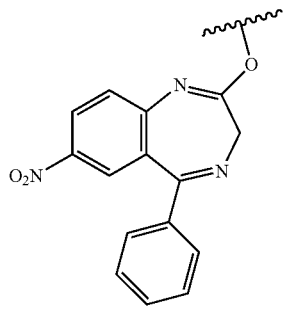 [SMILES: *OC1=Nc2ccc([N+](=O)[O-])cc2C(c2ccccc2)=NC1]

19
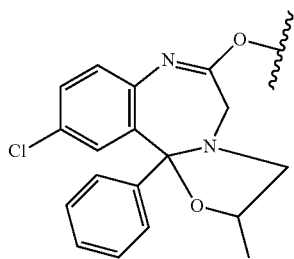 [SMILES: *OC1=Nc2ccc(Cl)cc2C2(c3ccccc3)OC(C)CN2C1]

20
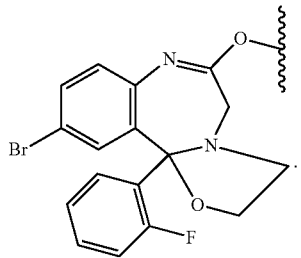 [SMILES: *OC1=Nc2ccc(Br)cc2C2(c3ccccc3F)OCCN2C1]

Prodrugs of Acylanilines

In one embodiment, the compounds suitable for use in the methods of the invention are derivatives of acylaniline-, -containing parent drugs that are substituted at the amide nitrogen or oxygen atom with labile aldehyde-linked prodrug moieties.

In one embodiment, compounds of the present invention are represented by Formula III below, or its geometric isomers, enantiomers, diastereomers, racemates, pharmaceutically acceptable salts and solvates thereof:

Formula III
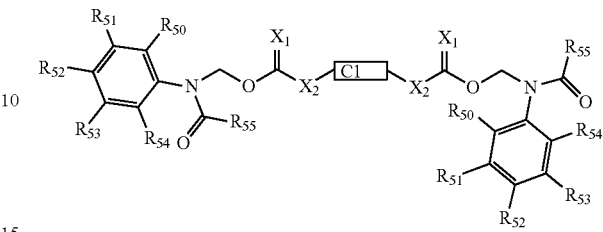

wherein each $R_{50}$, $R_{51}$, $R_{52}$, $R_{53}$, $R_{54}$ and $R_{55}$ is independently selected from hydrogen, halogen, $-OR_{10}$, $-SR_{10}$, $-NR_{10}R_{11}-$, optionally substituted aliphatic, optionally substituted aryl or optionally substituted heterocyclyl; alternatively, two or more $R_{50}$, $R_{51}$, $R_{52}$, $R_{53}$, $R_{54}$ and $R_{55}$ together form an optionally substituted ring.

In one embodiment, the parent drug moieties (APIs), are selected from Table 4. In one embodiment, the prodrug is a compound of Formula II wherein API-1 and API-2 are independently selected from Table-4. In one embodiment both API-1 and API-2 represent the same parent drug.

TABLE 4

1
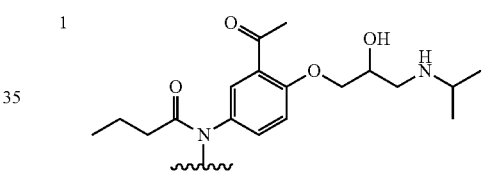

2
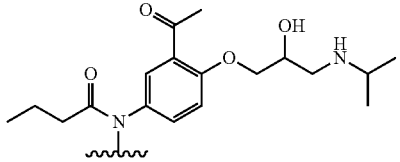 [SMILES: *N(C(=O)CCC)c1ccc(OCC(O)CNC(C)C)c(C(C)=O)c1]

3
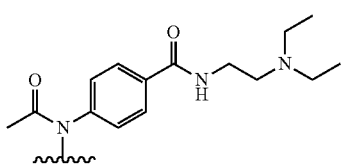 [SMILES: *N(C(C)=O)c1ccc(C(=O)NCCN(CC)CC)cc1]

4
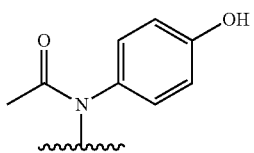 [SMILES: *N(C(C)=O)c1ccc(O)cc1]

5
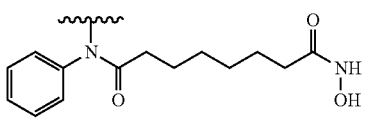 [SMILES: *N(C(=O)CCCCCCC(=O)NO)c1ccccc1]

TABLE 4-continued
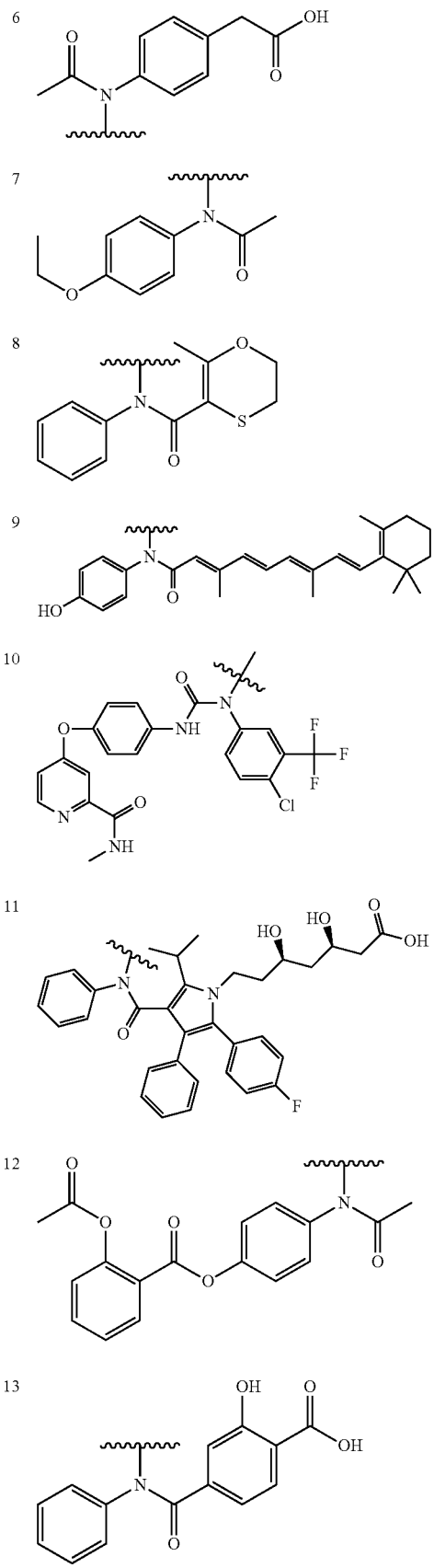
TABLE 4-continued
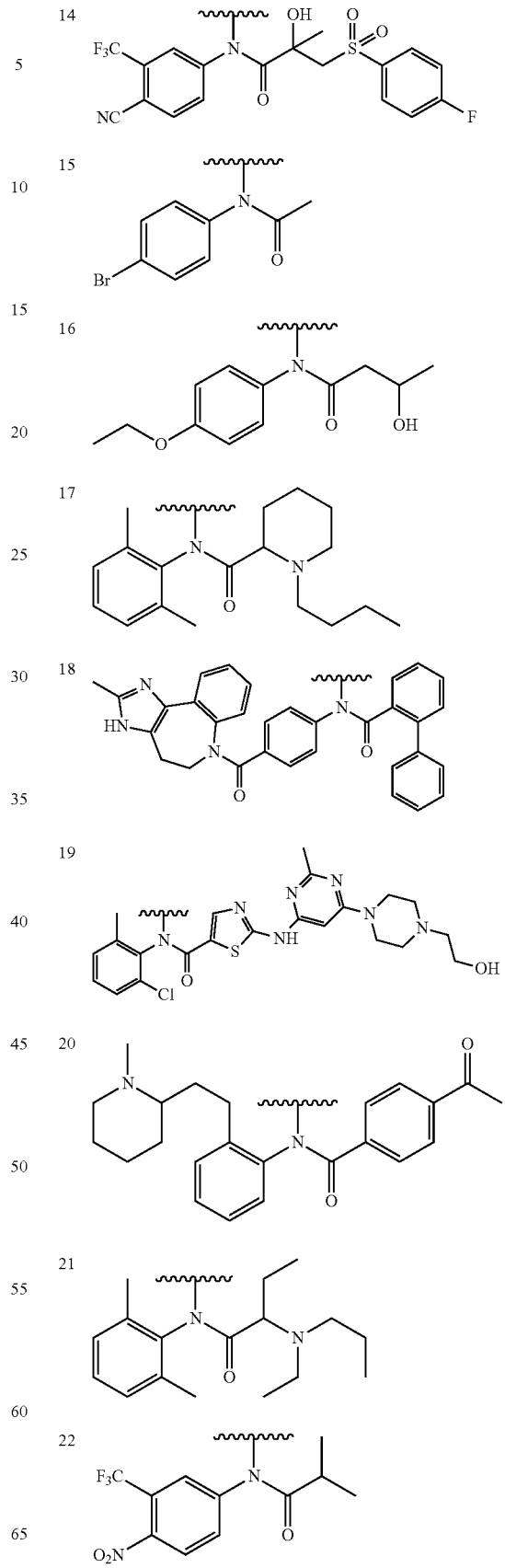

TABLE 4-continued
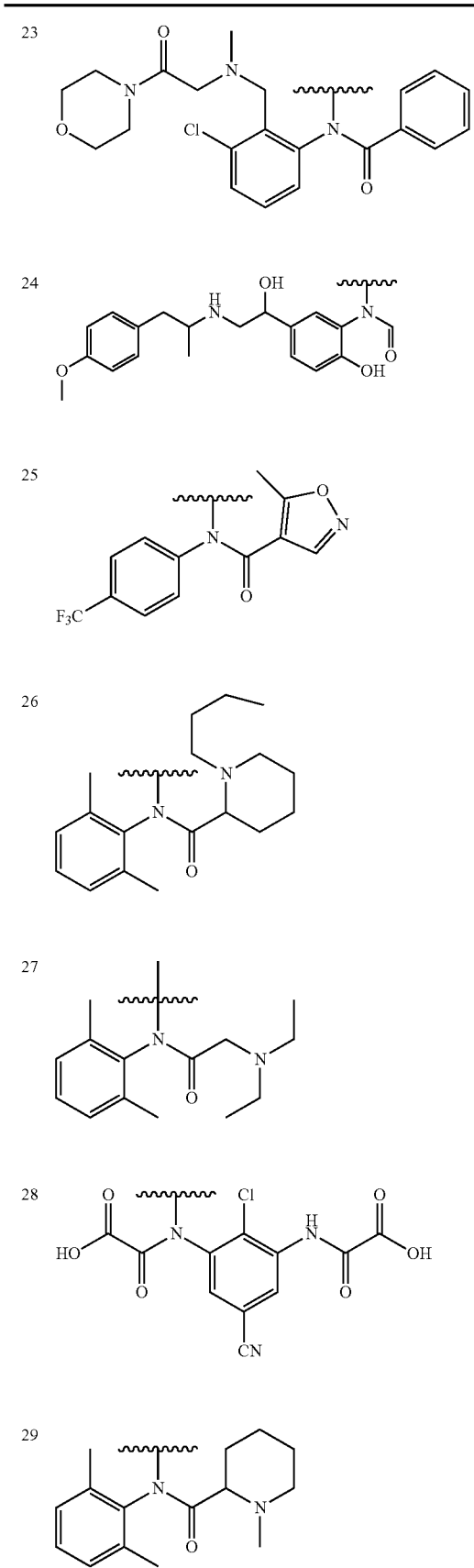
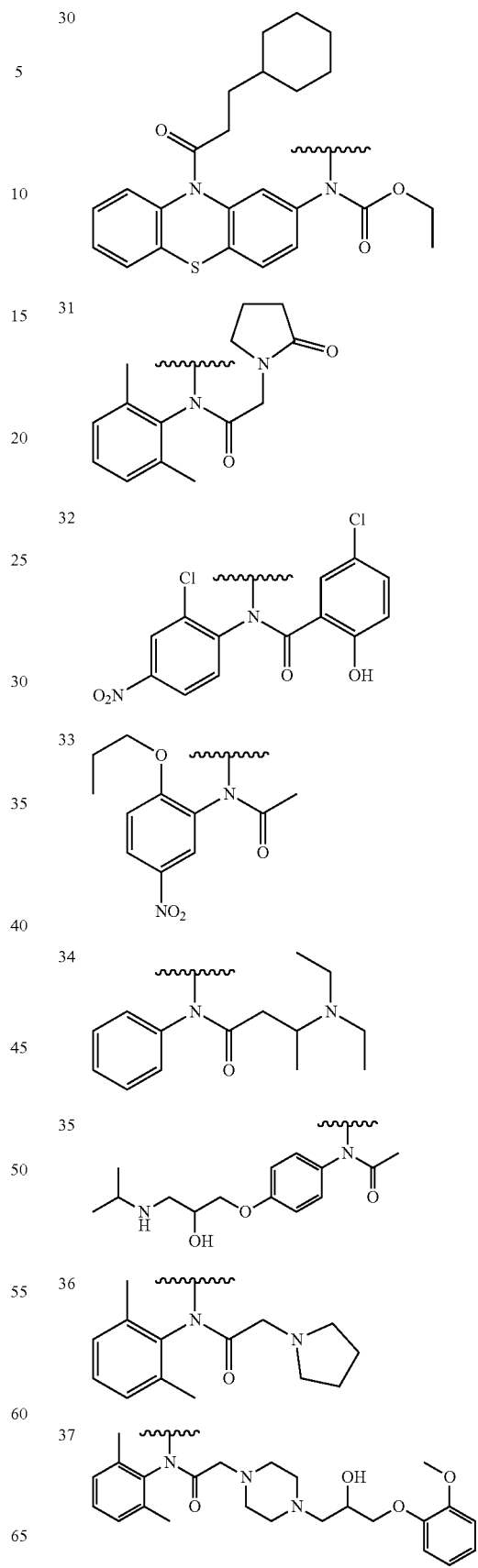

TABLE 4-continued
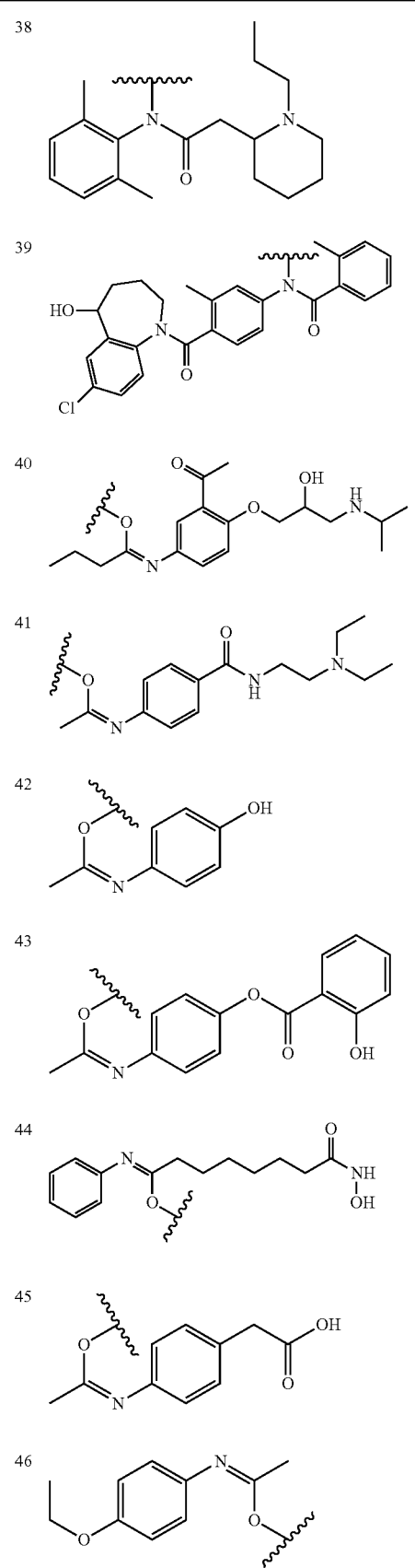
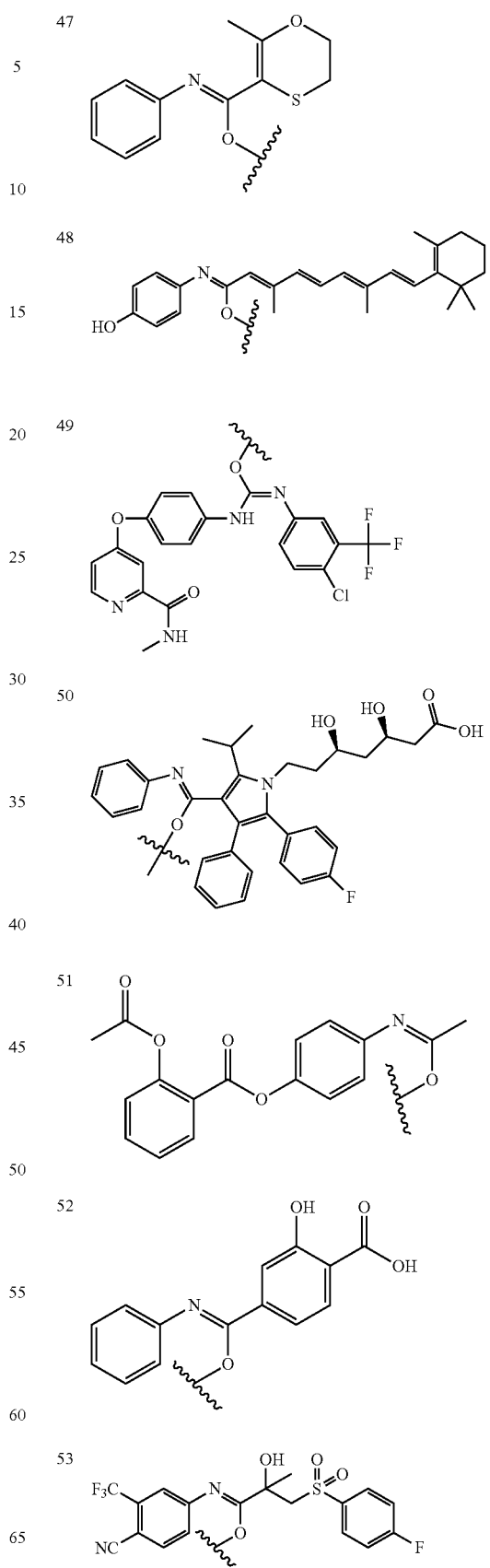

TABLE 4-continued
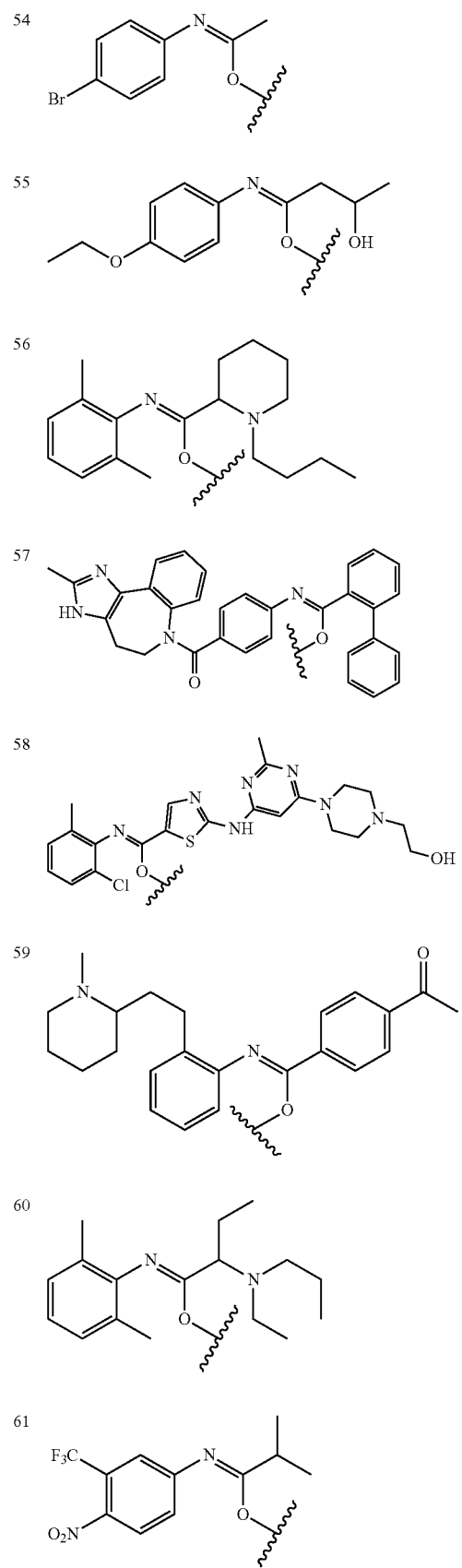
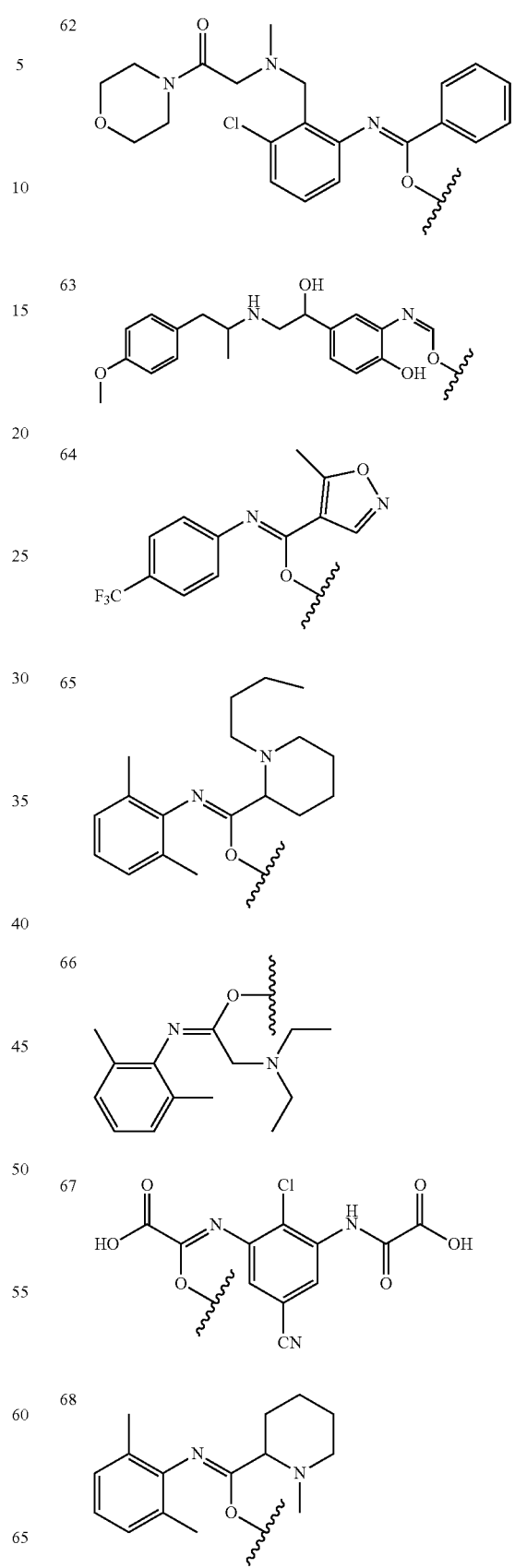

TABLE 4-continued

69 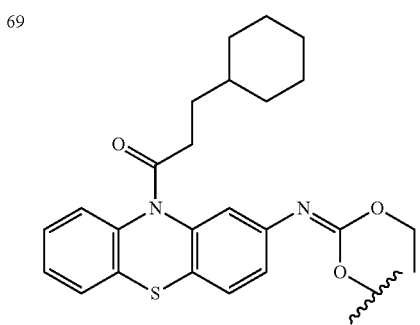

70 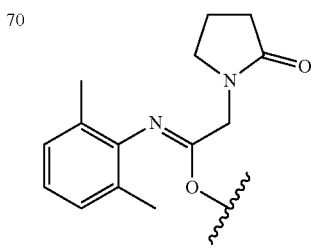

71 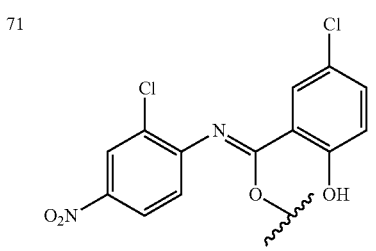

72 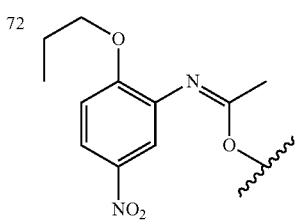

73 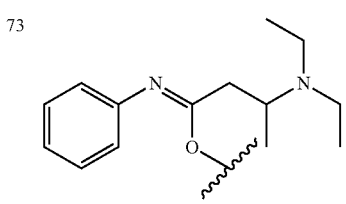

74 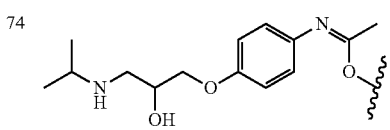

75 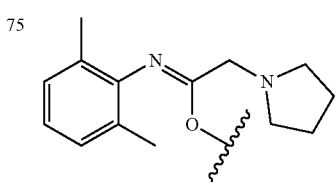

TABLE 4-continued

76

77

78

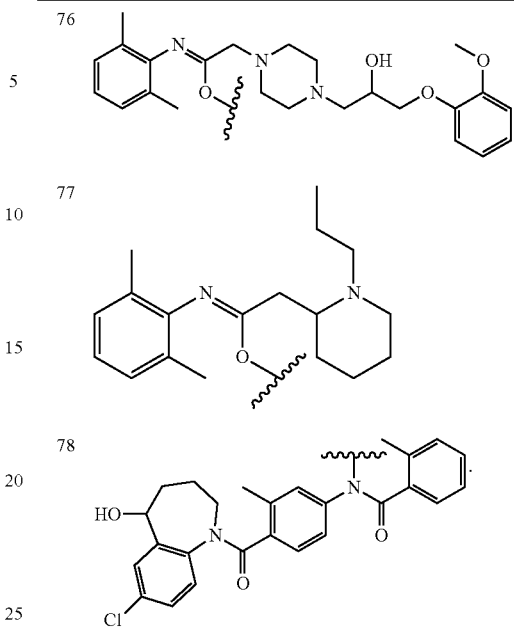

Thiazolidinones

In one embodiment, the compounds suitable for use in the methods of the invention are derivatives of thioazolidine-, -containing parent drugs that are substituted at an amide nitrogen or oxygen atom with labile aldehyde-linked prodrug moieties.

In one embodiment, compounds of the present invention are represented by Formula IV below, or its geometric isomers, enantiomers, diastereomers, racemates, pharmaceutically acceptable salts and solvates thereof:

Formula IV

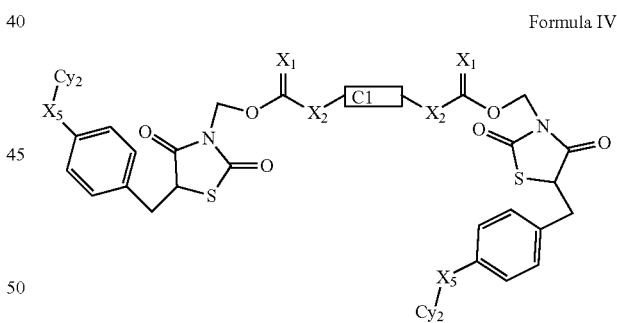

wherein $Cy_2$ is an optionally substituted heterocyclic ring; and $X_5$ is selected from absent, —S—, —O—, —S(O)—, —S(O)$_2$—, —N(R$_{10}$)—, —C(O)—, —C(OR$_{10}$)(R$_{11}$)—, —[C(R$_{10}$)(R$_{11}$)]$_v$—, —O [C(R$_{10}$)(R$_{11}$)]$_v$—, —O [C(R$_{10}$)(R$_{11}$)]$_v$O—, —S[C(R$_{10}$)(R$_{11}$)]$_v$O—, —NR$_{12}$[C(R$_{10}$)(R$_{11}$)]$_v$O—, —NR$_{12}$[C(R$_{10}$)(R$_{11}$)]$_v$S—, —S[C(R$_{10}$)(R$_{11}$)]$_v$—, —C(O)[C(R$_{10}$)(R$_{11}$)]$_v$—, and —C(R$_{10}$)(R$_{11}$)=C(R$_{10}$)(R$_{11}$)—; wherein v is 0, 1, 2, 3, 4, 5, 6, 7, 8, 9 or 10.

In one embodiment, the parent drug moieties (APIs), are independently selected from Table 5. In one embodiment, the prodrug is a compound of Formula II wherein API-1 and API-2 are selected from Table-5. In one embodiment both API-1 and API-2 represent the same parent drug.

TABLE 5
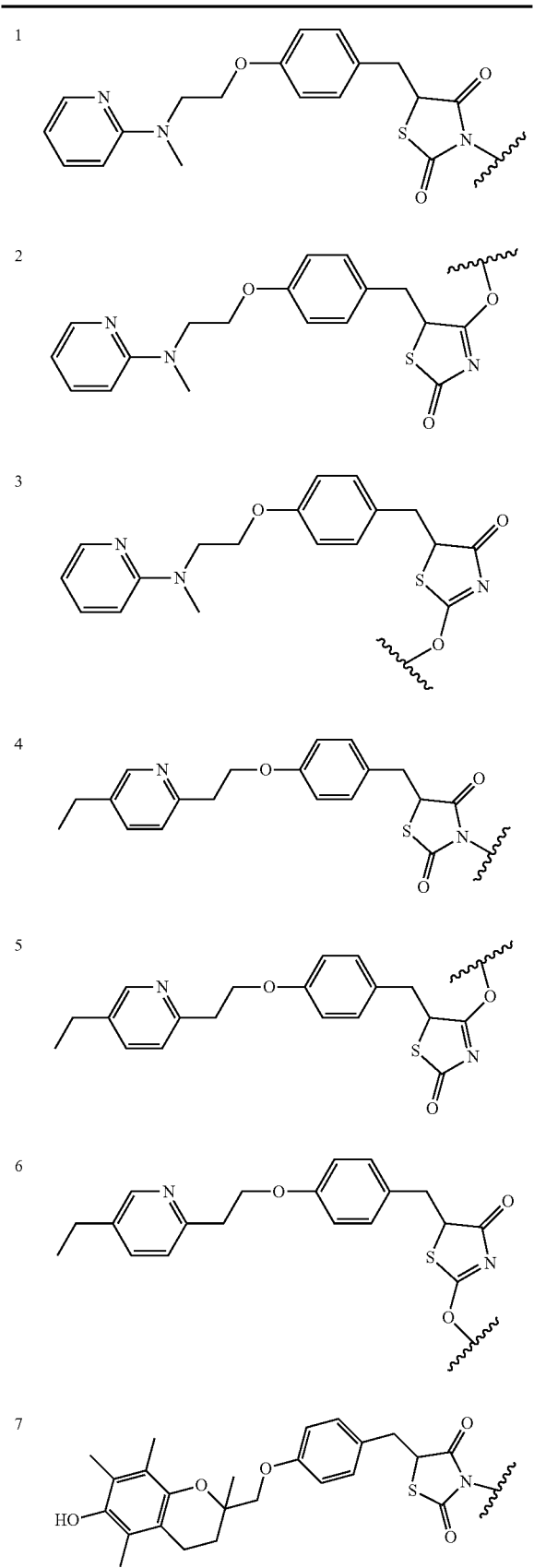
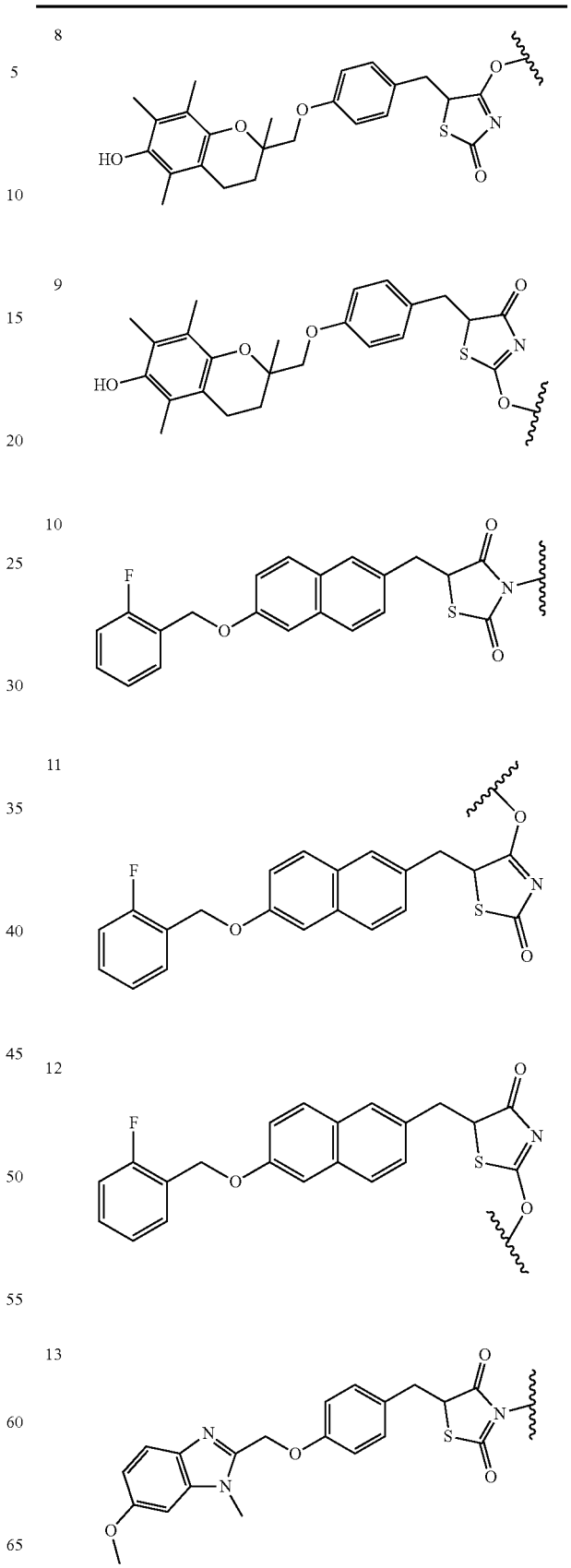

TABLE 5-continued

14 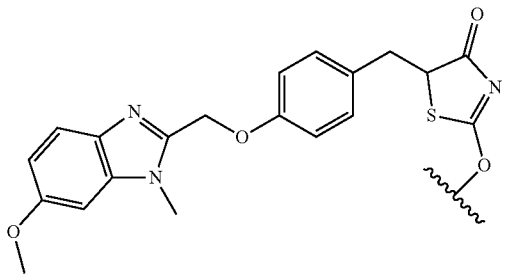 [SMILES: *OC1=NC(=O)C(Cc2ccc(OCc3nc4ccc(OC)cc4n3C)cc2)S1]

15 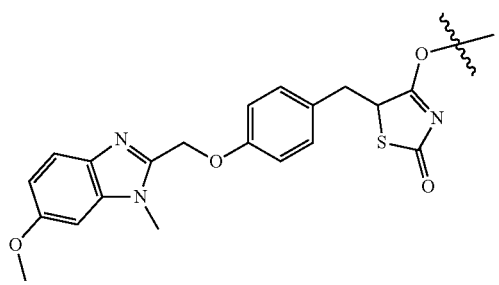 [SMILES: *OC1=NC(=O)SC1Cc1ccc(OCc2nc3ccc(OC)cc3n2C)cc1]

16 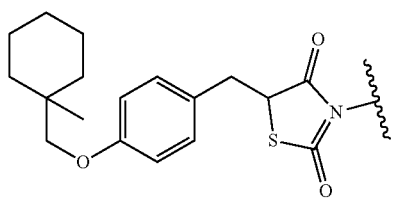

17 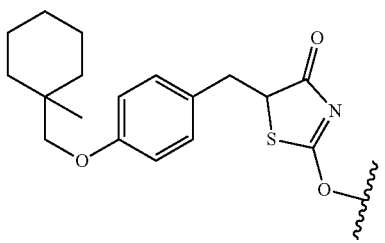 [SMILES: *OC1=NC(=O)C(Cc2ccc(OCC3(C)CCCCC3)cc2)S1]

18 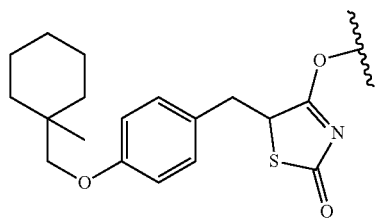 [SMILES: *OC1=NC(=O)SC1Cc1ccc(OCC2(C)CCCCC2)cc1]

19 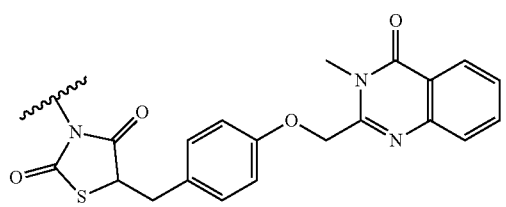 [SMILES: *N1C(=O)SC(Cc2ccc(OCc3nc4ccccc4c(=O)n3C)cc2)C1=O]

TABLE 5-continued

20 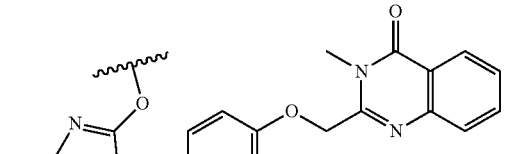

21 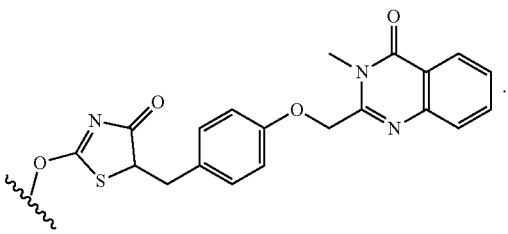

Barbiturates

In one embodiment, the compounds suitable for use in the methods of the invention are derivatives of barbiturates that are substituted at an amide nitrogen or oxygen atom with labile aldehyde-linked prodrug moieties.

In one embodiment, the parent drug moieties (APIs), are selected from Table 6. In one embodiment, the prodrug is a compound of Formula II wherein API-1 and API-2 are selected from Table-6. In one embodiment both API-1 and API-2 represent the same parent drug.

TABLE 6

1 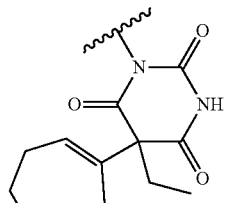

2 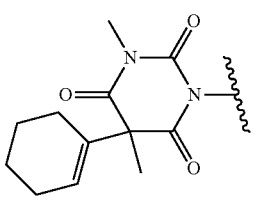 [SMILES: *N1C(=O)N(C)C(=O)C(C)(C2=CCCCC2)C1=O]

3 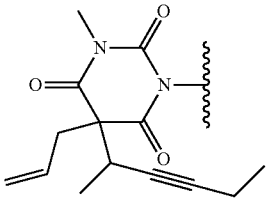 [SMILES: *N1C(=O)N(C)C(=O)C(CC=C)(C(C)C#CCC)C1=O]

4 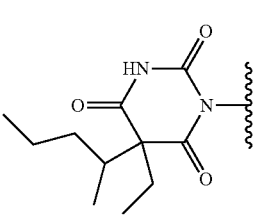 [SMILES: *N1C(=O)NC(=O)C(CC)(C(C)CCC)C1=O]

TABLE 6-continued

| | |
|---|---|
| 5 | 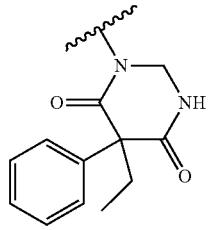 [SMILES: *N1CNC(=O)C(CC)(c2ccccc2)C1=O] |
| 6 | 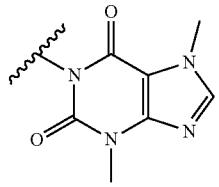 [SMILES: *n1c(=O)c2c(ncn2C)n(C)c1=O] |
| 7 | 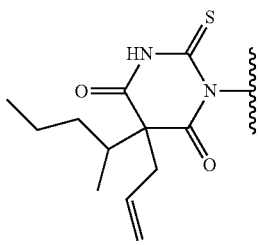 [SMILES: *N1C(=O)C(CC=C)(C(C)CCC)C(=O)NC1=S] |
| 8 | 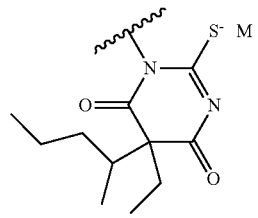 |
| 9 | 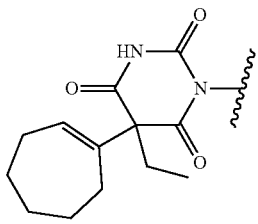 [SMILES: *N1C(=O)NC(=O)C(CC)(C2=CCCCCC2)C1=O] |
| 10 | 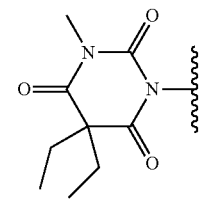 [SMILES: *N1C(=O)N(C)C(=O)C(CC)(CC)C1=O] |
| 11 | 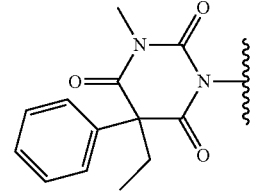 [SMILES: *N1C(=O)N(C)C(=O)C(CC)(c2ccccc2)C1=O] |

TABLE 6-continued

| | |
|---|---|
| 12 | 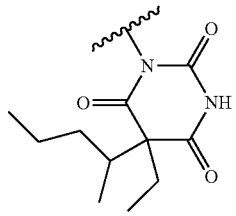 [SMILES: *N1C(=O)NC(=O)C(CC)(C(C)CCC)C1=O] |
| 13 | 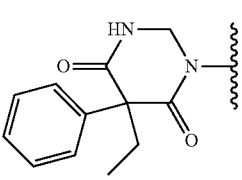 [SMILES: *N1CNC(=O)C(CC)(c2ccccc2)C1=O] |
| 14 | 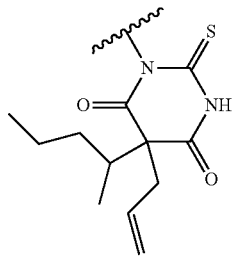 [SMILES: *N1C(=O)C(CC=C)(C(C)CCC)C(=O)NC1=S] |
| 15 | 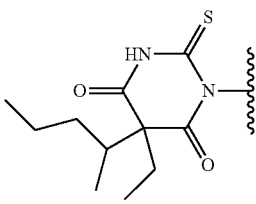 [SMILES: *N1C(=O)C(CC)(C(C)CCC)C(=O)NC1=S] |
| 16 | 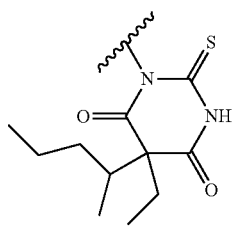 [SMILES: *N1C(=O)C(CC)(C(C)CCC)C(=O)NC1=S] | wherein M is a pharmaceutically acceptable cation.

Prodrugs of Pyridone and Pyrimidine Containing Parent Drugs

In one embodiment, the compounds suitable for use in the methods of the invention are derivatives of pyridine and pyrimidine containing parent drugs that are substituted at the amide nitrogen or oxygen atom with labile aldehyde-linked prodrug moieties.

In one embodiment, the parent drug moieties (APIs), are selected from Table 7. In one embodiment, the prodrug is a compound of Formula II wherein API-1 and API-2 are selected from Table-7. In one embodiment both API-1 and API-2 represent the same parent drug.

TABLE 7
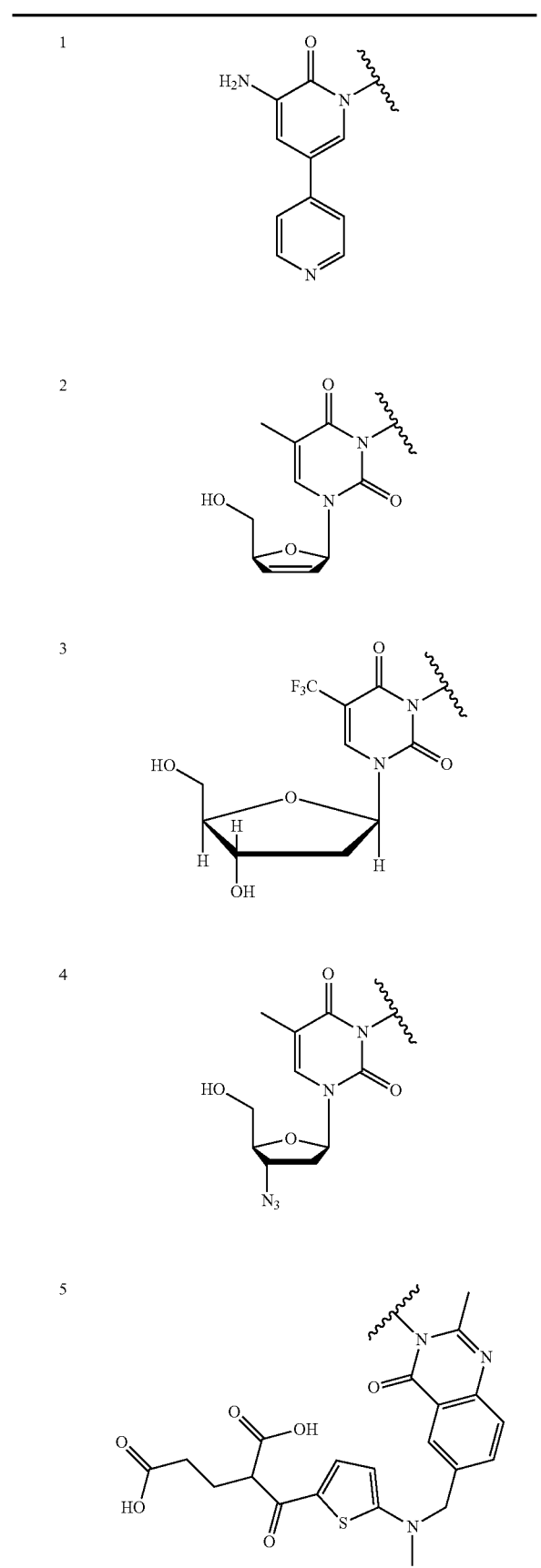
TABLE 7-continued
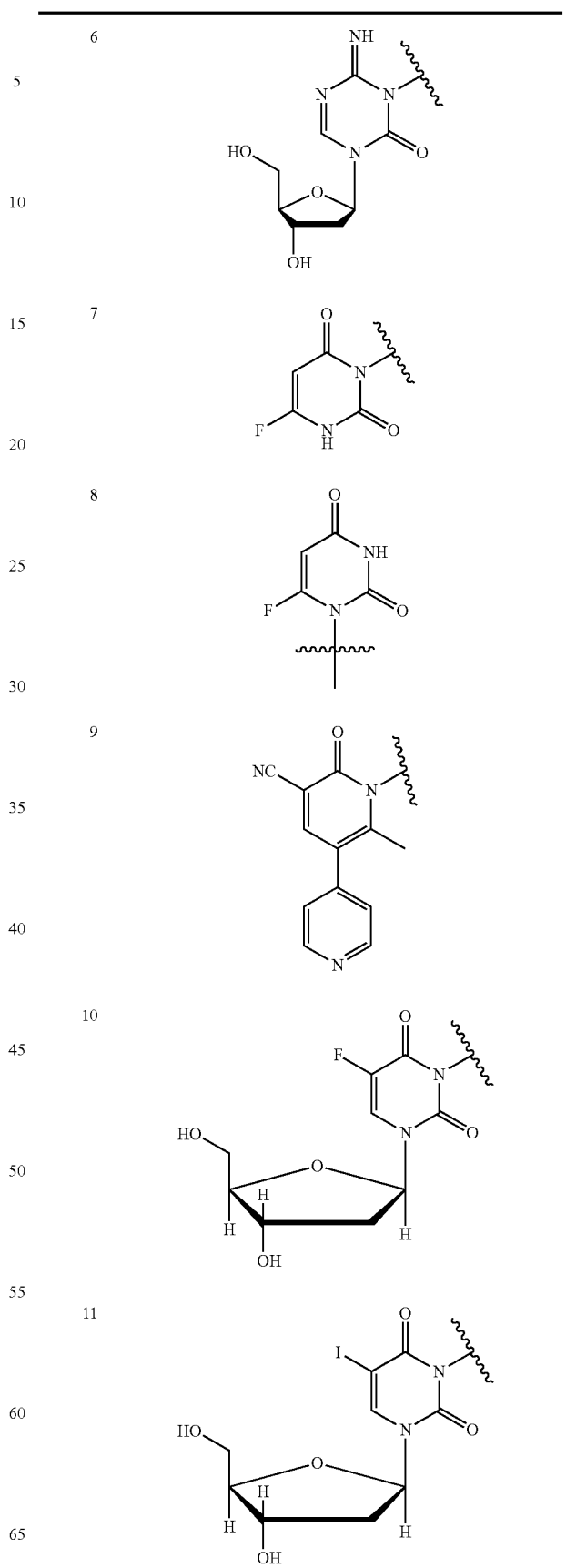

TABLE 7-continued

| | |
|---|---|
| 12 | 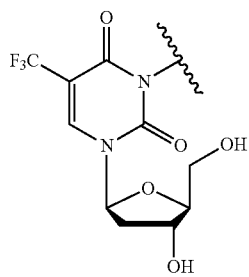 |
| 13 | 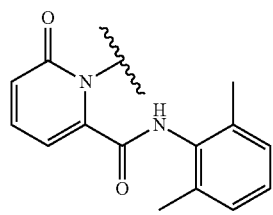 [SMILES: *n1c(C(=O)Nc2c(C)cccc2C)cccc1=O] |
| 14 | 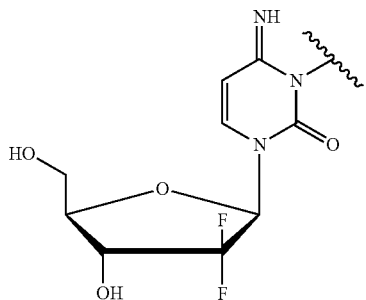 |
| 15 | 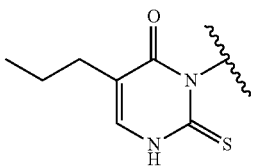 [SMILES: *n1c(=S)[nH]cc(CCC)c1=O] |
| 16 | 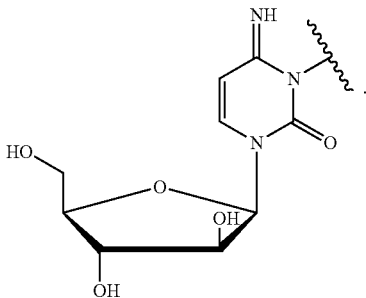 |

Prodrugs of Benzamide Parent Drugs

In one embodiment, the compounds suitable for use in the methods of the invention are derivatives of benzamide containing parent drugs that are substituted at the amide nitrogen or oxygen atom with labile aldehyde-linked prodrug moieties.

In one embodiment, the parent drug moieties (APIs) are independently selected from Table 8. In one embodiment, the prodrug is a compound of Formula II wherein API-1 and API-2 are selected from Table-8. In one embodiment both API-1 and API-2 represent the same parent drug.

TABLE 8

| | |
|---|---|
| 1 | 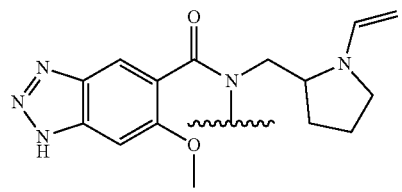 [SMILES: *N(CC1CCCN1C=C)C(=O)c1cc2nn[nH]c2cc1OC] |
| 2 | 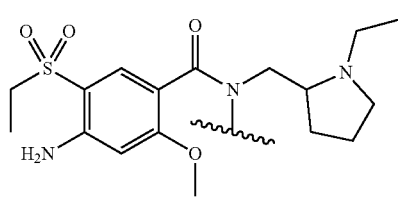 [SMILES: *N(CC1CCCN1CC)C(=O)c1cc(S(=O)(=O)CC)c(N)cc1OC] |
| 3 | 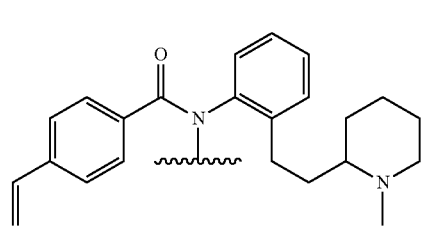 [SMILES: *N(C(=O)c1ccc(C=C)cc1)c1ccccc1CCC1CCCCN1C] |
| 4 | 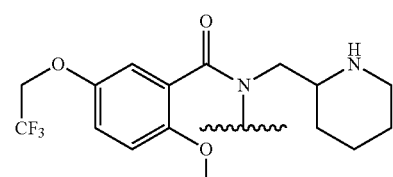 |
| 5 | 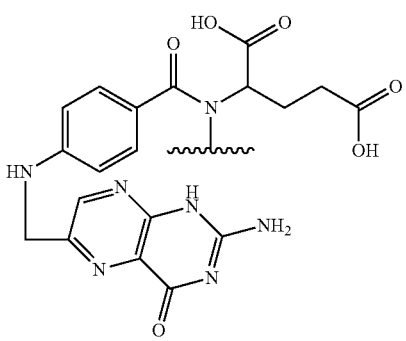 [SMILES: *N(C(=O)c1ccc(NCc2cnc3[nH]c(N)nc(=O)c3n2)cc1)C(CCC(=O)O)C(=O)O] |
| 6 | 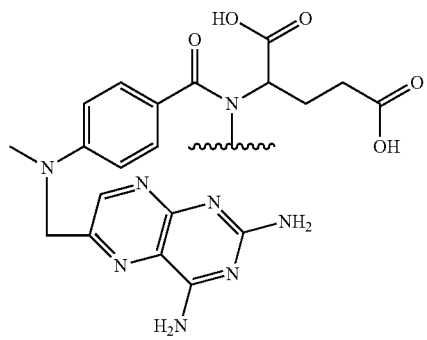 [SMILES: *N(C(=O)c1ccc(N(C)Cc2cnc3nc(N)nc(N)c3n2)cc1)C(CCC(=O)O)C(=O)O] |

TABLE 8-continued
| | |
|---|---|
| 7 | 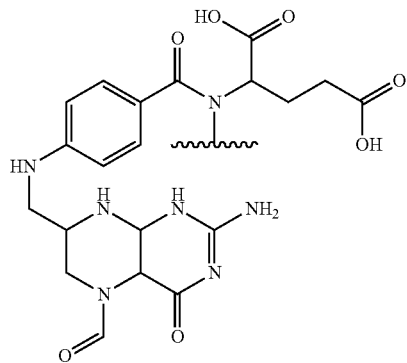 [SMILES: *N(C(=O)c1ccc(NCC2CN(C=O)C3C(=O)N=C(N)NC3N2)cc1)C(CCC(=O)O)C(=O)O] |
| 8 | 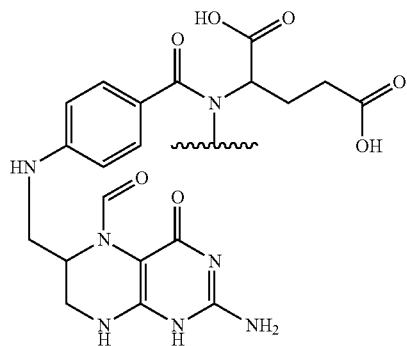 [SMILES: *N(C(=O)c1ccc(NCC2CNc3[nH]c(N)nc(=O)c3N2C=O)cc1)C(CCC(=O)O)C(=O)O] |
| 9 | 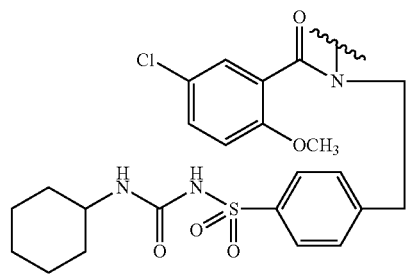 [SMILES: *N(CCc1ccc(S(=O)(=O)NC(=O)NC2CCCCC2)cc1)C(=O)c1cc(Cl)ccc1OC] |
| 10 | 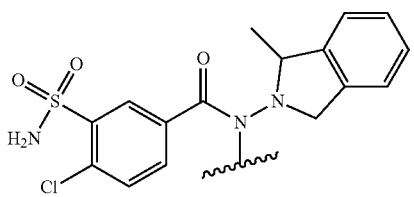 [SMILES: *N(C(=O)c1ccc(Cl)c(S(N)(=O)=O)c1)N1Cc2ccccc2C1C] |
| 11 | 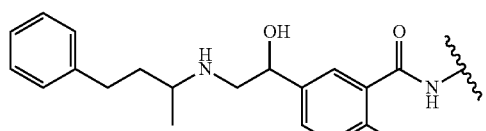 |
| 12 | 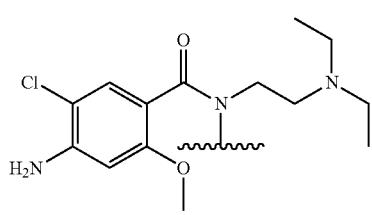 [SMILES: *N(CCN(CC)CC)C(=O)c1cc(Cl)c(N)cc1OC] |
TABLE 8-continued
| | |
|---|---|
| 13 | 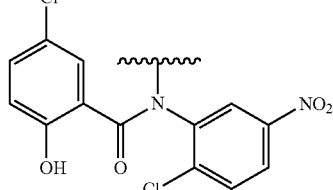 |
| 14 | 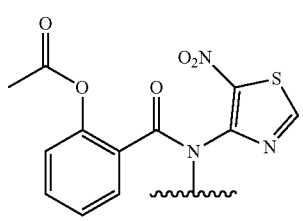 [SMILES: *N(C(=O)c1ccccc1OC(C)=O)c1ncsc1[N+](=O)[O-]] |
| 15 | 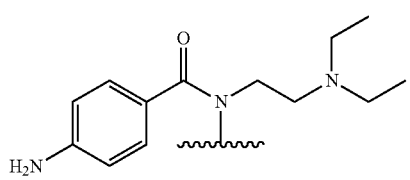 [SMILES: *N(CCN(CC)CC)C(=O)c1ccc(N)cc1] |
| 16 | 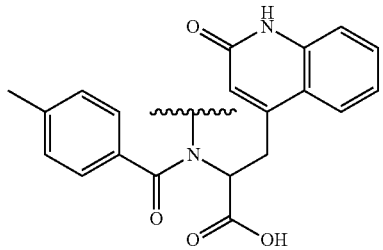 [SMILES: *N(C(=O)c1ccc(C)cc1)C(Cc1cc(=O)[nH]c2ccccc12)C(=O)O] |
| 17 | 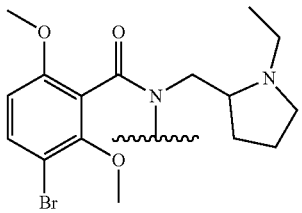 [SMILES: *N(CC1CCCN1CC)C(=O)c1c(OC)ccc(Br)c1OC] |
| 18 | 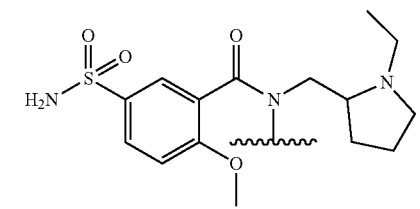 [SMILES: *N(CC1CCCN1CC)C(=O)c1cc(S(N)(=O)=O)ccc1OC] |
| 19 | 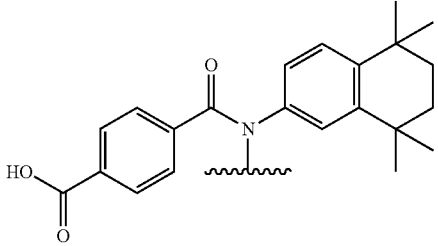 [SMILES: *N(C(=O)c1ccc(C(=O)O)cc1)c1ccc2c(c1)C(C)(C)CCC2(C)C] |

TABLE 8-continued
20 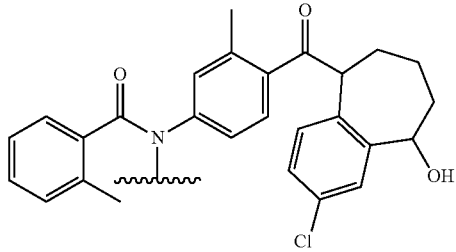 [SMILES: *N(C(=O)c1ccccc1C)c1ccc(C(=O)C2CCCC(O)c3cc(Cl)ccc32)c(C)c1]
21 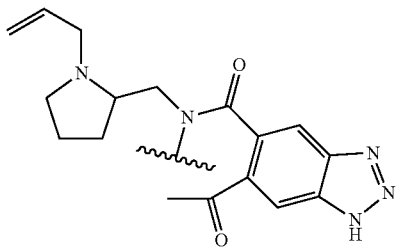 [SMILES: *N(CC1CCCN1CC=C)C(=O)c1cc2nn[nH]c2cc1C(C)=O]
22 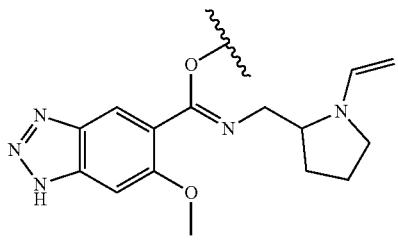 [SMILES: *O/C(=N\CC1CCCN1C=C)c1cc2nn[nH]c2cc1OC]
23 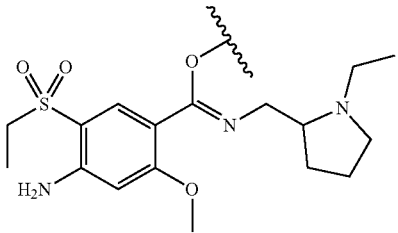 [SMILES: *O/C(=N\CC1CCCN1CC)c1cc(S(=O)(=O)CC)c(N)cc1OC]
24 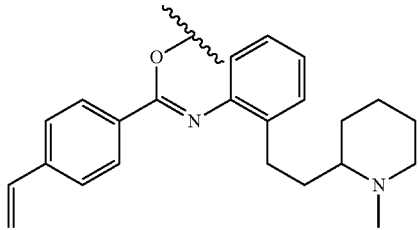 [SMILES: *O/C(=N\c1ccccc1CCC1CCCCN1C)c1ccc(C=C)cc1]
25 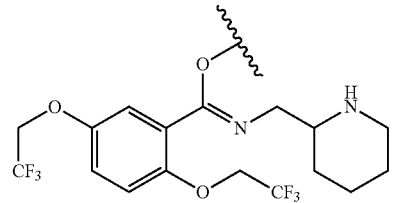 [SMILES: *O/C(=N\CC1CCCCN1)c1cc(OCC(F)(F)F)ccc1OCC(F)(F)F]
TABLE 8-continued
26 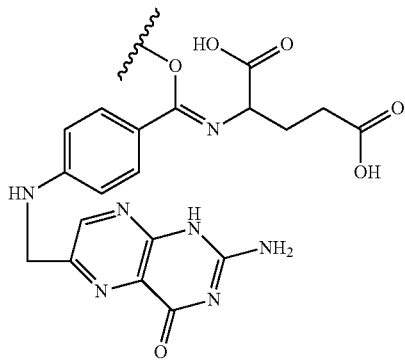 [SMILES: *O/C(=N\C(CCC(=O)O)C(=O)O)c1ccc(NCc2cnc3[nH]c(N)nc(=O)c3n2)cc1]
27 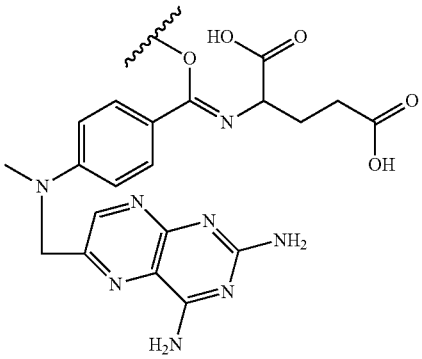 [SMILES: *O/C(=N\C(CCC(=O)O)C(=O)O)c1ccc(N(C)Cc2cnc3nc(N)nc(N)c3n2)cc1]
28 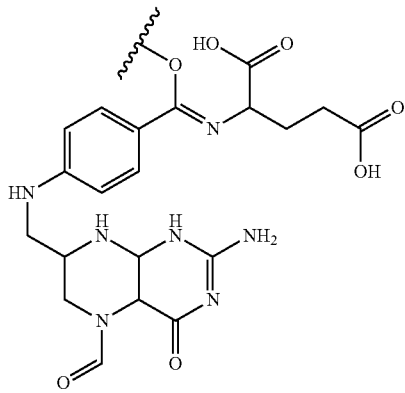 [SMILES: *O/C(=N\C(CCC(=O)O)C(=O)O)c1ccc(NCC2CN(C=O)C3C(=O)N=C(N)NC3N2)cc1]
29 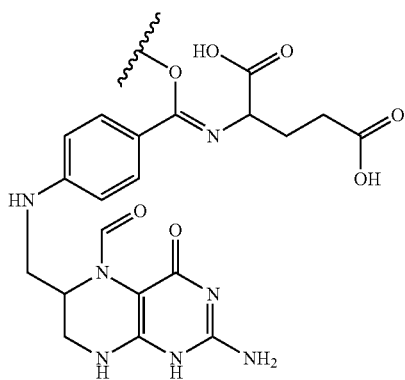 [SMILES: *O/C(=N\C(CCC(=O)O)C(=O)O)c1ccc(NCC2CNc3[nH]c(N)nc(=O)c3N2C=O)cc1]

TABLE 8-continued
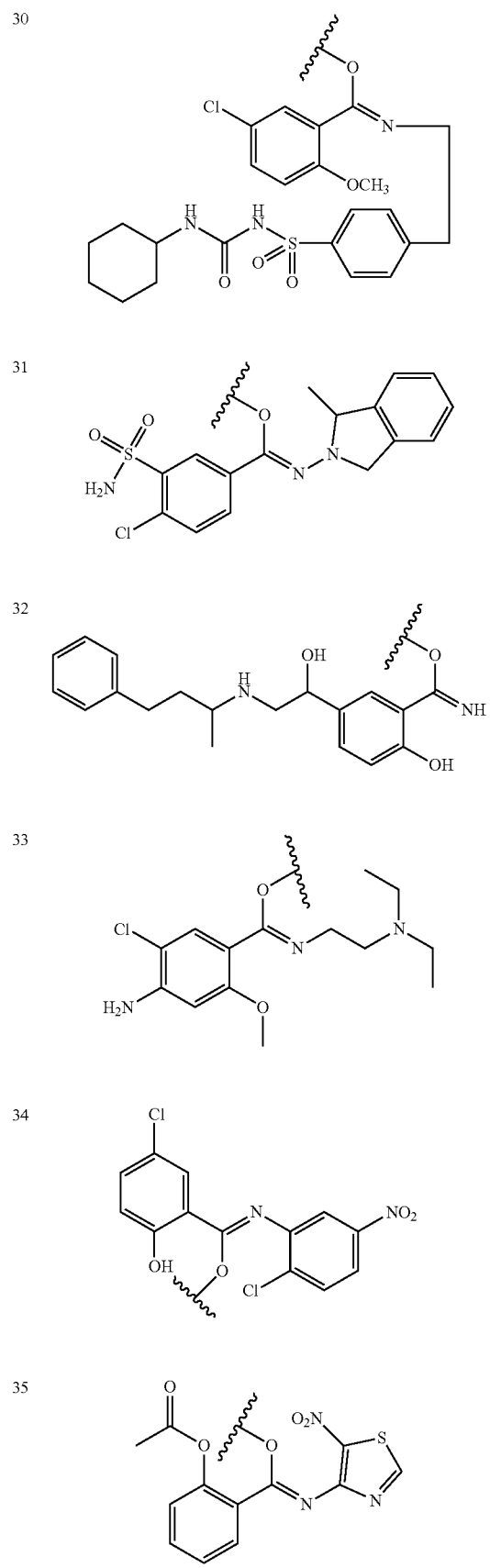
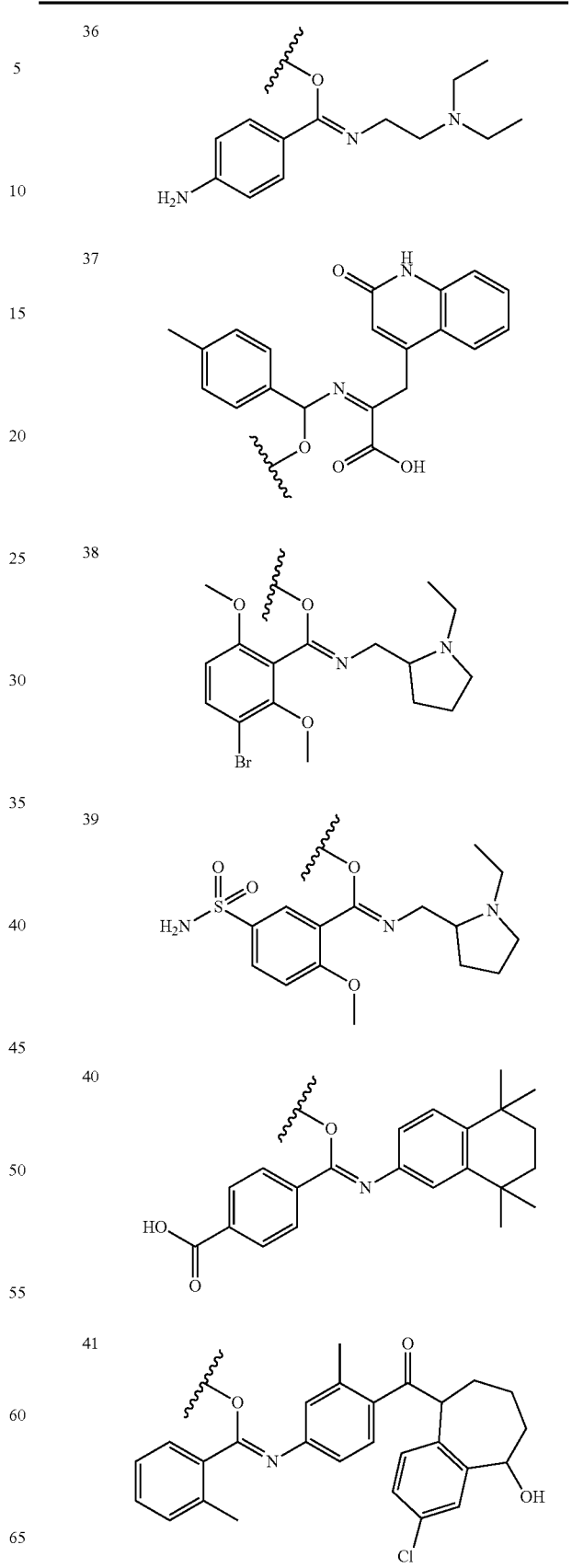

TABLE 8-continued

42 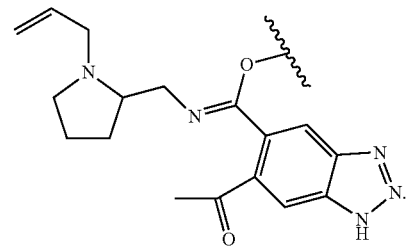 [SMILES: *O/C(=N\CC1CCCN1CC=C)c1cc2nn[nH]c2cc1C(C)=O]

Prodrugs of Imide Containing Parent Drugs

In one embodiment, the compounds suitable for use in the methods of the invention are derivatives of imide containing parent drugs that are substituted at the amide nitrogen or oxygen atom with labile aldehyde-linked prodrug moieties.

In one embodiment, the parent drug moieties (APIs) are independently selected from Table 9. In one embodiment, the prodrug is a compound of Formula II wherein API-1 and API-2 are selected from Table-9. In one embodiment both API-1 and API-2 represent the same parent drug.

TABLE 9

1. 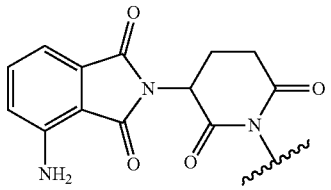 [SMILES: *N1C(=O)CCC(N2C(=O)c3cccc(N)c3C2=O)C1=O]

2. 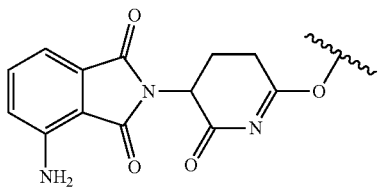 [SMILES: *OC1=NC(=O)C(N2C(=O)c3cccc(N)c3C2=O)CC1]

3. 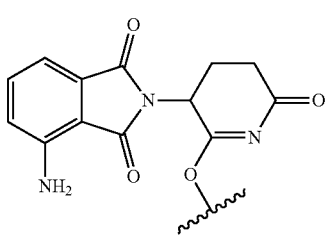 [SMILES: *OC1=NC(=O)CCC1N1C(=O)c2cccc(N)c2C1=O]

4. 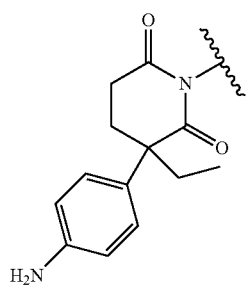 [SMILES: *N1C(=O)CCC(CC)(c2ccc(N)cc2)C1=O]

TABLE 9-continued

5. 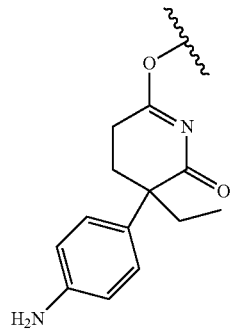 [SMILES: *OC1=NC(=O)C(CC)(c2ccc(N)cc2)CC1]

6. 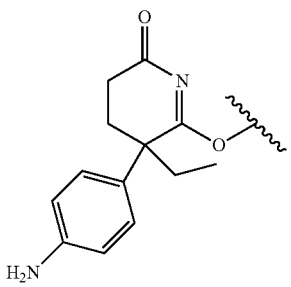 [SMILES: *OC1=NC(=O)CCC1(CC)c1ccc(N)cc1]

7. 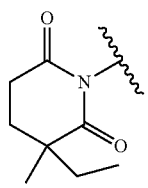 [SMILES: *N1C(=O)CCC(C)(CC)C1=O]

8. 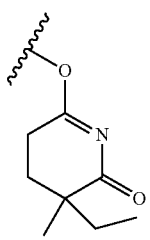 [SMILES: *OC1=NC(=O)C(C)(CC)CC1]

9. 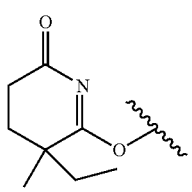 [SMILES: *OC1=NC(=O)CCC1(C)CC]

10. 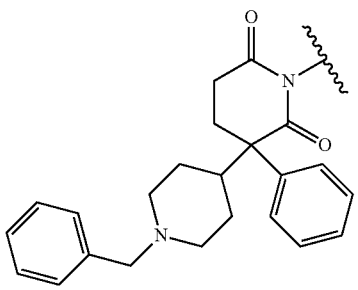 [SMILES: *N1C(=O)CCC(c2ccccc2)(C2CCN(Cc3ccccc3)CC2)C1=O]

TABLE 9-continued
| 11. | 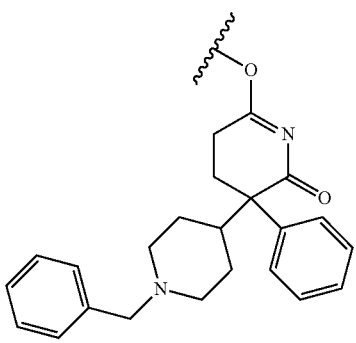 [SMILES: *OC1=NC(=O)C(c2ccccc2)(C2CCN(Cc3ccccc3)CC2)CC1] |
| 12. | 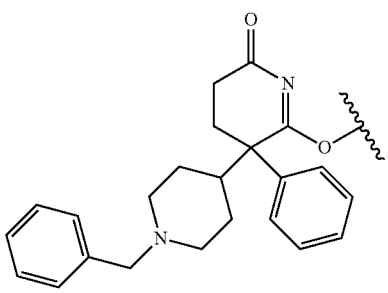 [SMILES: *OC1=NC(=O)CCC1(c1ccccc1)C1CCN(Cc2ccccc2)CC1] |
| 13. | 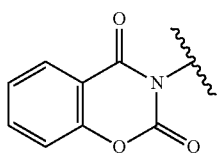 [SMILES: *n1c(=O)oc2ccccc2c1=O] |
| 14. | 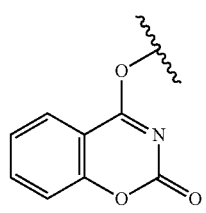 [SMILES: *Oc1nc(=O)oc2ccccc12] |
| 15. | 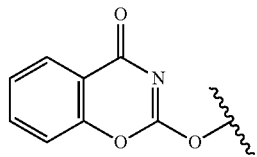 [SMILES: *Oc1nc(=O)c2ccccc2o1] |
| 16. | 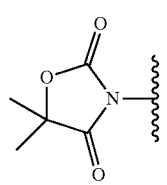 [SMILES: *N1C(=O)OC(C)(C)C1=O] |
| 17. | 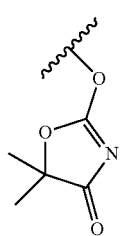 [SMILES: *OC1=NC(=O)C(C)(C)O1] |
TABLE 9-continued
| 18. | 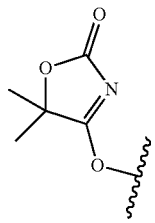 [SMILES: *OC1=NC(=O)OC1(C)C] |
| 19. | 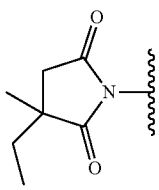 [SMILES: *N1C(=O)CC(C)(CC)C1=O] |
| 20. | 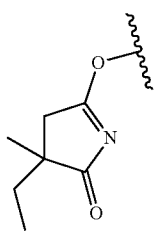 [SMILES: *OC1=NC(=O)C(C)(CC)C1] |
| 21. | 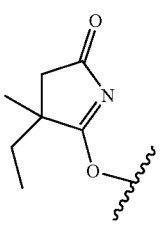 [SMILES: *OC1=NC(=O)CC1(C)CC] |
| 22. | 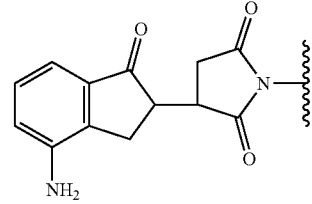 [SMILES: *N1C(=O)CC(C2Cc3c(N)cccc3C2=O)C1=O] |
| 23. | 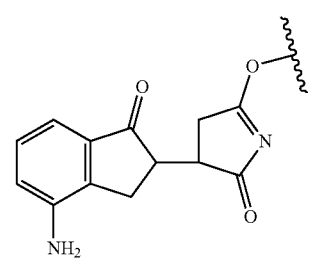 [SMILES: *OC1=NC(=O)C(C2Cc3c(N)cccc3C2=O)C1] |
| 24. | 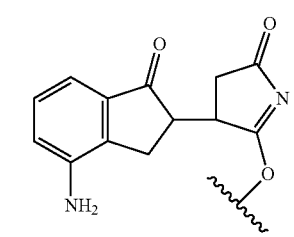 [SMILES: *OC1=NC(=O)CC1C1Cc2c(N)cccc2C1=O] |

TABLE 9-continued
| | |
|---|---|
| 25 | 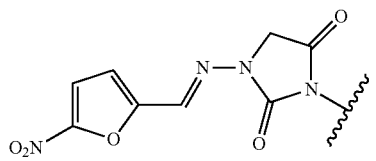 [SMILES: *N1C(=O)CN(/N=C/c2ccc([N+](=O)[O-])o2)C1=O] |
| 26. | 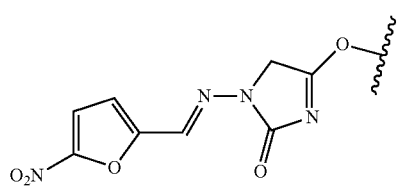 [SMILES: *OC1=NC(=O)N(/N=C/c2ccc([N+](=O)[O-])o2)C1] |
| 27. | 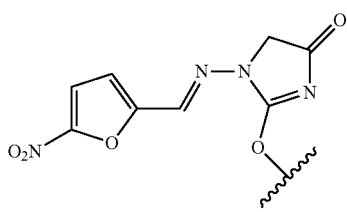 [SMILES: *OC1=NC(=O)CN1/N=C/c1ccc([N+](=O)[O-])o1] |
| 28 | 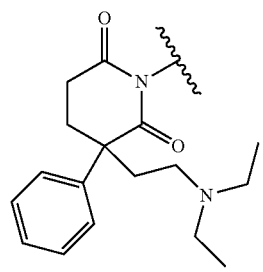 [SMILES: *N1C(=O)CCC(CCN(CC)CC)(c2ccccc2)C1=O] |
| 29. | 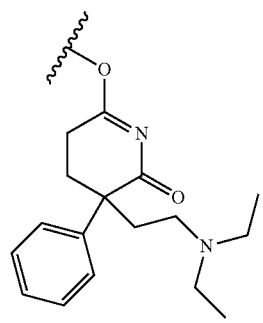 [SMILES: *OC1=NC(=O)C(CCN(CC)CC)(c2ccccc2)CC1] |
| 30. | 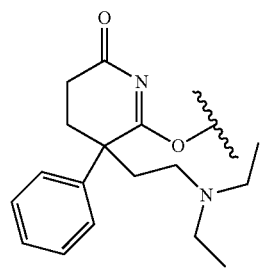 [SMILES: *OC1=NC(=O)CCC1(CCN(CC)CC)c1ccccc1] |
| 31 | 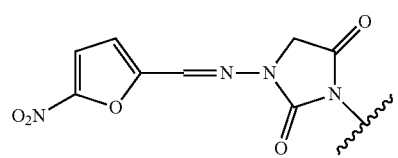 [SMILES: *N1C(=O)CN(N=Cc2ccc([N+](=O)[O-])o2)C1=O] |
TABLE 9-continued
| | |
|---|---|
| 32. | 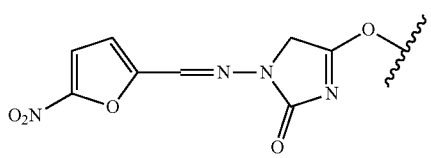 [SMILES: *OC1=NC(=O)N(N=Cc2ccc([N+](=O)[O-])o2)C1] |
| 33. | 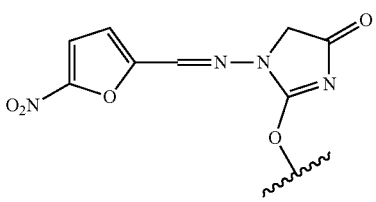 [SMILES: *OC1=NC(=O)CN1N=Cc1ccc([N+](=O)[O-])o1] |
| 34 | 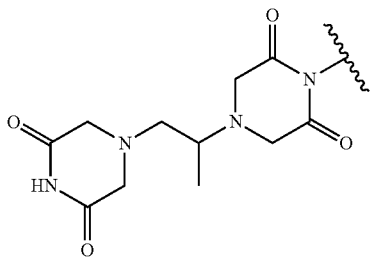 [SMILES: *N1C(=O)CN(C(C)CN2CC(=O)NC(=O)C2)CC1=O] |
| 35. | 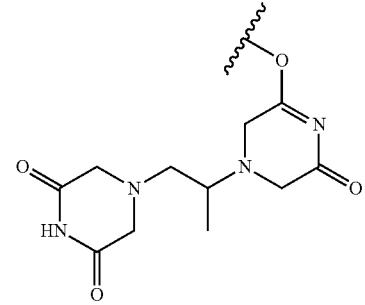 [SMILES: *OC1=NC(=O)CN(C(C)CN2CC(=O)NC(=O)C2)C1] |
| 36. | 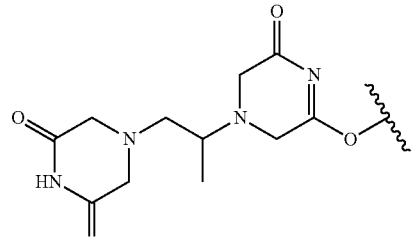 |
| 37 | 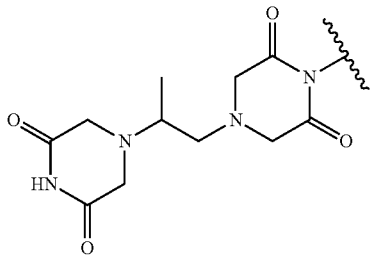 [SMILES: *N1C(=O)CN(CC(C)N2CC(=O)NC(=O)C2)CC1=O] |

TABLE 9-continued
| | |
|---|---|
| 38. 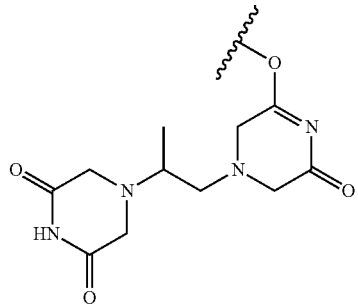 [SMILES: *OC1=NC(=O)CN(CC(C)N2CC(=O)NC(=O)C2)C1] | 42. 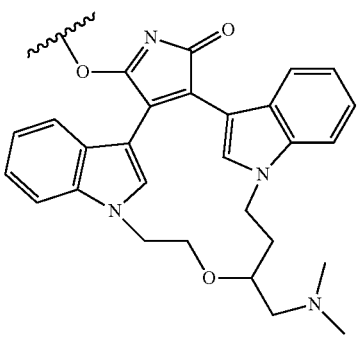 |
| 39. 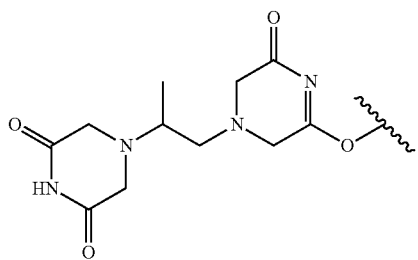 [SMILES: *OC1=NC(=O)CN(CC(C)N2CC(=O)NC(=O)C2)C1] | 43. 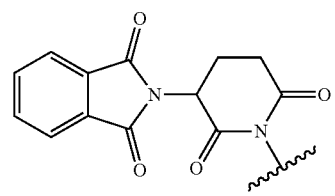 [SMILES: *N1C(=O)CCC(N2C(=O)c3ccccc3C2=O)C1=O] |
| | 44. 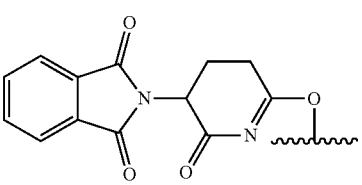 [SMILES: *OC1=NC(=O)C(N2C(=O)c3ccccc3C2=O)CC1] |
| 40. 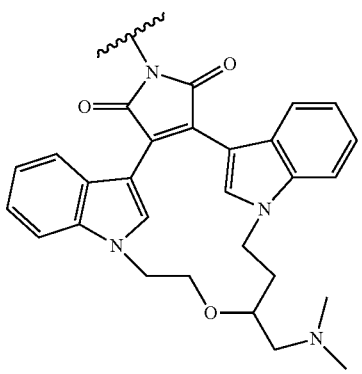 | 45. 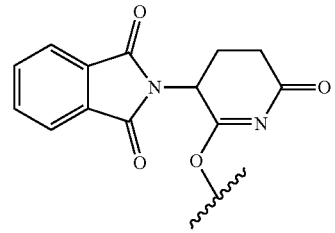 [SMILES: *OC1=NC(=O)CCC1N1C(=O)c2ccccc2C1=O] |
| | 46. 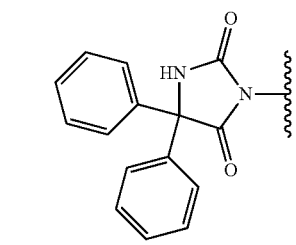 [SMILES: *N1C(=O)NC(c2ccccc2)(c2ccccc2)C1=O] |
| 41. 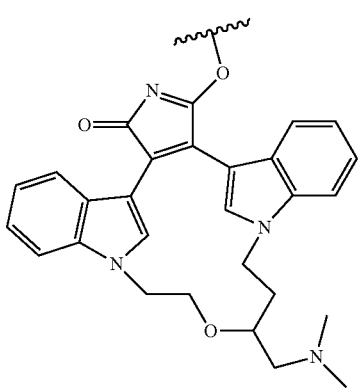 | 47. 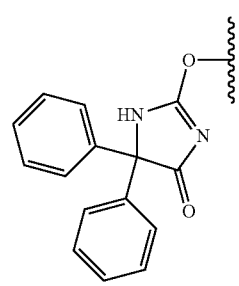 [SMILES: *OC1=NC(=O)C(c2ccccc2)(c2ccccc2)N1] |

TABLE 9-continued

48. 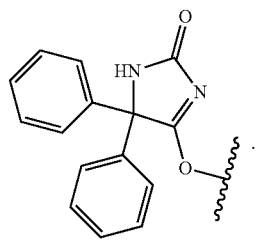 [SMILES: *OC1=NC(=O)NC1(c1ccccc1)c1ccccc1]

Prodrugs of Cyclic Ureas

In one embodiment, the compounds suitable for use in the methods of the invention are derivatives of cyclic urea-containing parent drugs that are substituted at either of the urea nitrogens or oxygen with labile aldehyde-linked prodrug moieties.

In one embodiment, the parent drug moieties (APIs), are independently selected from Table 10. In one embodiment, the prodrug is a compound of Formula II wherein API-1 and API-2 are selected from Table-10. In one embodiment both API-1 and API-2 represent the same parent drug.

TABLE 10

| No | Structure |
| --- | --- |
| 1 | 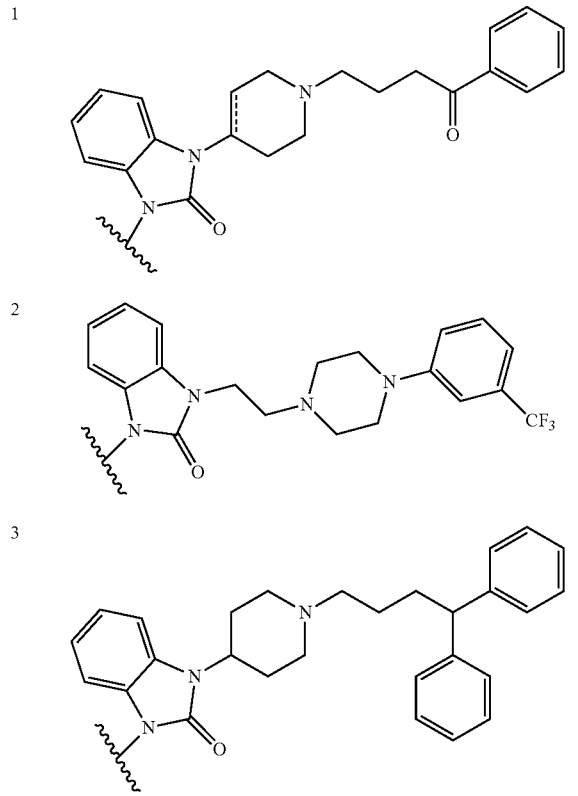 |

TABLE 10-continued

| No | Structure |
| --- | --- |
| 5 | 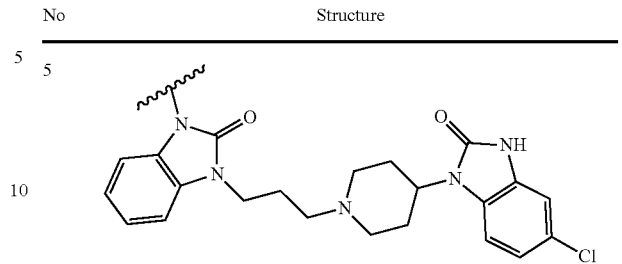 |
| 6 | 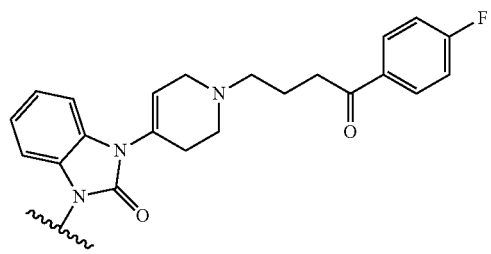 [SMILES: *n1c(=O)n(C2=CCN(CCCC(=O)c3ccc(F)cc3)CC2)c2ccccc21] |
| 7 | 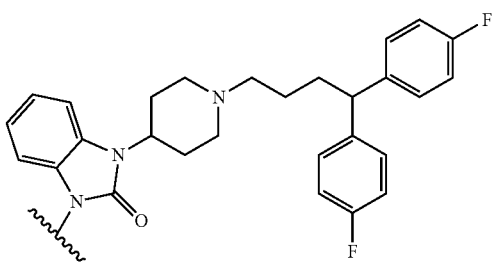 [SMILES: *n1c(=O)n(C2CCN(CCCC(c3ccc(F)cc3)c3ccc(F)cc3)CC2)c2ccccc21] |
| 8 | 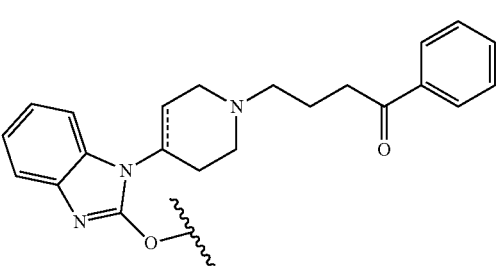 |
| 9 | 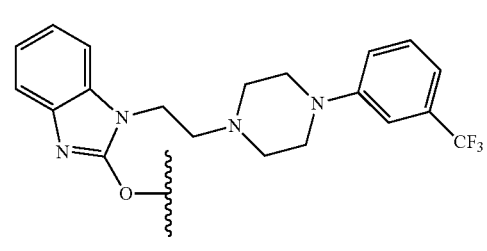 [SMILES: *Oc1nc2ccccc2n1CCN1CCN(c2cccc(C(F)(F)F)c2)CC1] |
| 10 | 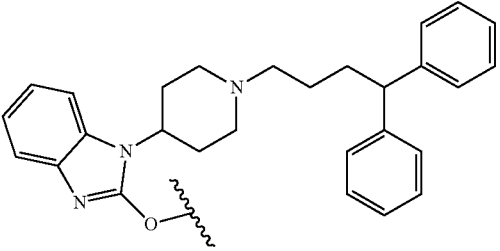 [SMILES: *Oc1nc2ccccc2n1C1CCN(CCCC(c2ccccc2)c2ccccc2)CC1] |

TABLE 10-continued

| No | Structure |
|----|-----------|
| 11 | 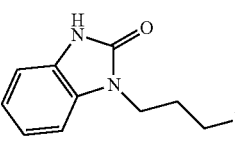 |
| 12 | 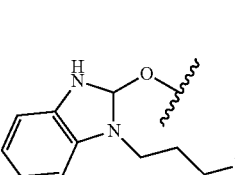 |
| 13 | 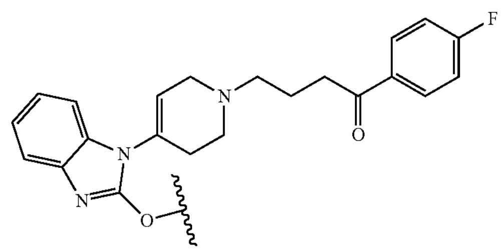 [SMILES: *Oc1nc2ccccc2n1C1=CCN(CCCC(=O)c2ccc(F)cc2)CC1] |
| 14 | 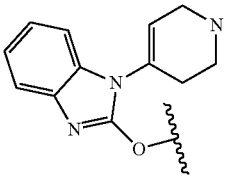 |

Prodrugs of Sulfonamide Parent Drugs

In one embodiment, the compounds suitable for use in the methods of the invention are derivatives of sulfonamide parent drugs that are substituted at the sulfonamide nitrogen or oxygen atom with labile aldehyde-linked prodrug moieties.

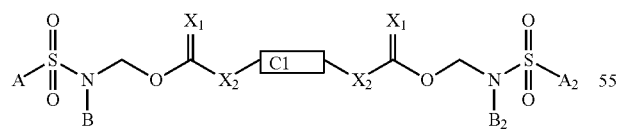

wherein A and B together with the sulfonamide group forms the parent drug; and, A2 and B2 together with the sulfonamide group form the parent drug.

In one embodiment, the parent drug moieties (APIs), are selected from Table 11. In one embodiment, the prodrug is a compound of Formula II wherein API-1 and API-2 are independently selected from Table-11. In one embodiment both API-1 and API-2 represent the same parent drug.

TABLE 11

| 1 | 2 | 3 | 4 | 5 | 6 | 7 |

TABLE 11-continued
8 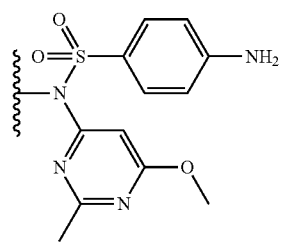 [SMILES: *N(c1cc(OC)nc(C)n1)S(=O)(=O)c1ccc(N)cc1]
9 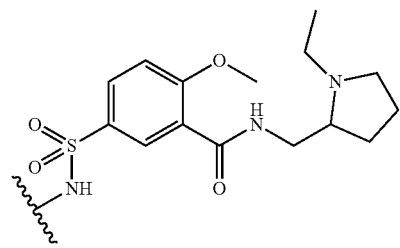 [SMILES: *NS(=O)(=O)c1ccc(OC)c(C(=O)NCC2CCCN2CC)c1]
10 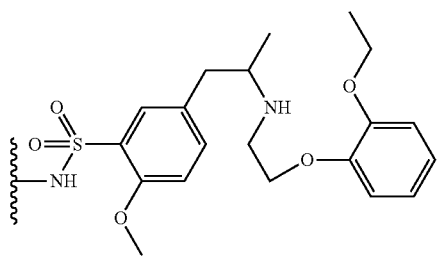 [SMILES: *NS(=O)(=O)c1cc(CC(C)NCCOc2ccccc2OCC)ccc1OC]
11 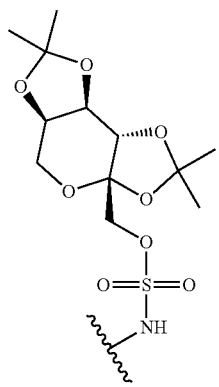
12 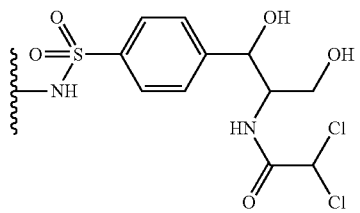 [SMILES: *NS(=O)(=O)c1ccc(C(O)C(CO)NC(=O)C(Cl)Cl)cc1]
13 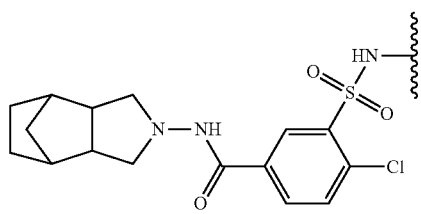 [SMILES: *NS(=O)(=O)c1cc(C(=O)NN2CC3C4CCC(C4)C3C2)ccc1Cl]
TABLE 11-continued
14 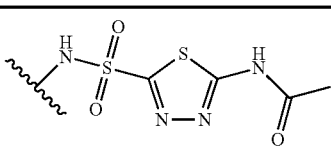
15 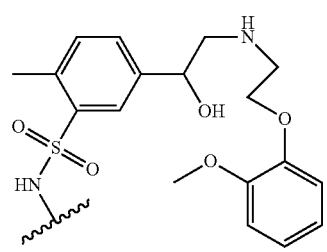 [SMILES: *NS(=O)(=O)c1cc(C(O)CNCCOc2ccccc2OC)ccc1C]
16 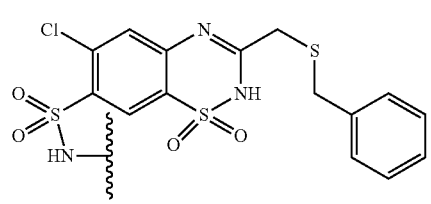 [SMILES: *NS(=O)(=O)c1cc2c(cc1Cl)N=C(CSCc1ccccc1)NS2(=O)=O]
17 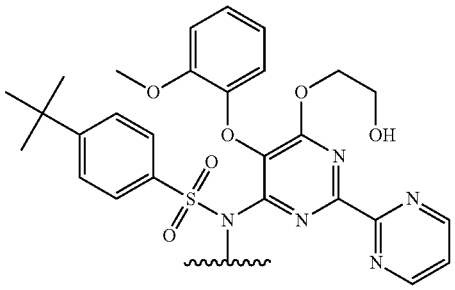 [SMILES: *N(c1nc(-c2ncccn2)nc(OCCO)c1Oc1ccccc1OC)S(=O)(=O)c1ccc(C(C)(C)C)cc1]
18 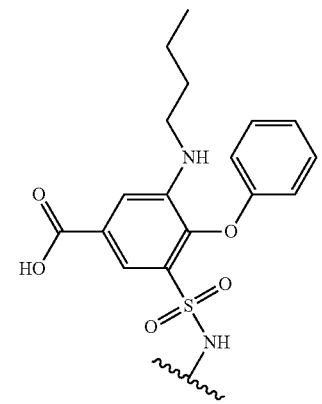 [SMILES: *NS(=O)(=O)c1cc(C(=O)O)cc(NCCCC)c1Oc1ccccc1]

TABLE 11-continued
| | |
|---|---|
| 19 | 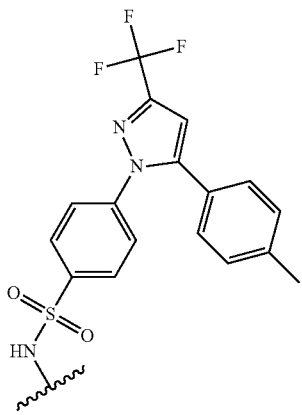 [SMILES: *NS(=O)(=O)c1ccc(-n2nc(C(F)(F)F)cc2-c2ccc(C)cc2)cc1] |
| 20 | 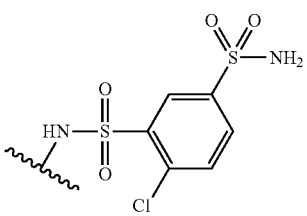 [SMILES: *NS(=O)(=O)c1cc(S(N)(=O)=O)ccc1Cl] |
| 21 | 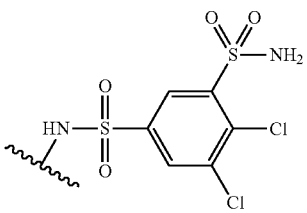 [SMILES: *NS(=O)(=O)c1cc(Cl)c(Cl)c(S(N)(=O)=O)c1] |
| 22 | 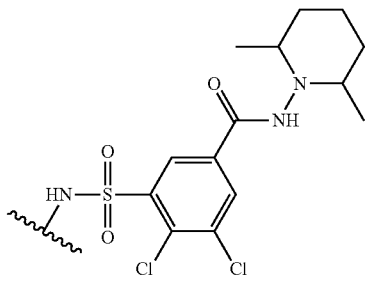 [SMILES: *NS(=O)(=O)c1cc(C(=O)NN2C(C)CCCC2C)cc(Cl)c1Cl] |
| 23 | 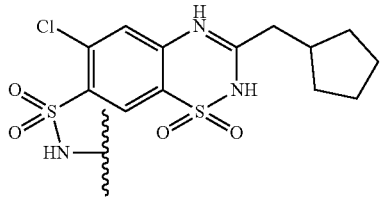 |
| 24 | 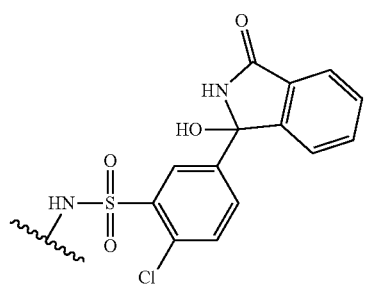 [SMILES: *NS(=O)(=O)c1cc(C2(O)NC(=O)c3ccccc32)ccc1Cl] |
| 25 | 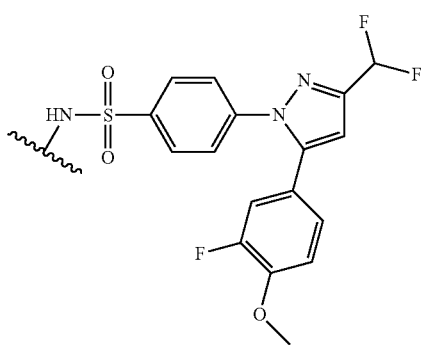 [SMILES: *NS(=O)(=O)c1ccc(-n2nc(C(F)F)cc2-c2ccc(OC)c(F)c2)cc1] |
| 26 | 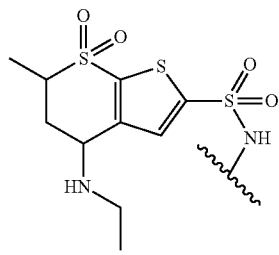 [SMILES: *NS(=O)(=O)c1cc2c(s1)S(=O)(=O)C(C)CC2NCC] |
| 27 | 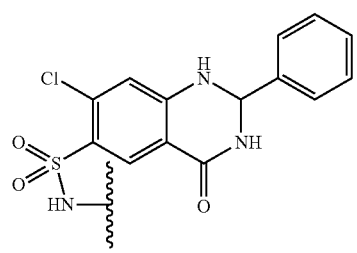 [SMILES: *NS(=O)(=O)c1cc2c(cc1Cl)NC(c1ccccc1)NC2=O] |
| 28 | 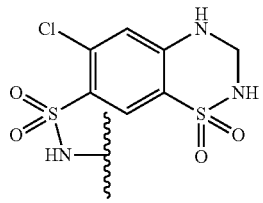 [SMILES: *NS(=O)(=O)c1cc2c(cc1Cl)NCNS2(=O)=O] |
| 29 | 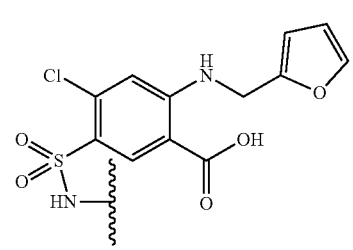 [SMILES: *NS(=O)(=O)c1cc(C(=O)O)c(NCc2ccco2)cc1Cl] |
| 30 | 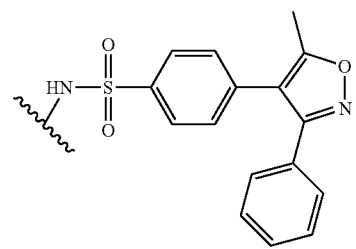 [SMILES: *NS(=O)(=O)c1ccc(-c2c(-c3ccccc3)noc2C)cc1] |

TABLE 11-continued
| | |
|---|---|
| 31 | 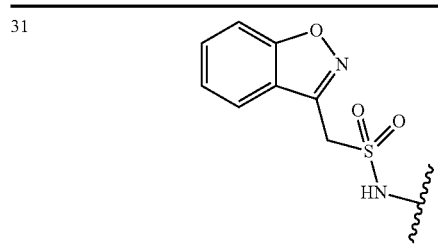 |
| 32 | |
| 33 | |
| 34 | |
| 35 | |
| 36 | 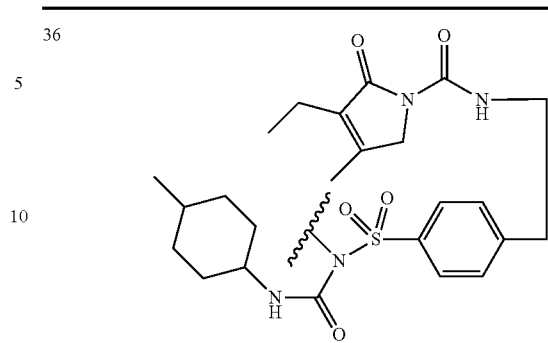 |
| 37 | |
| 38 | |
| 39 | |
| 40 | |
| 41 | |

TABLE 11-continued
| 42 | 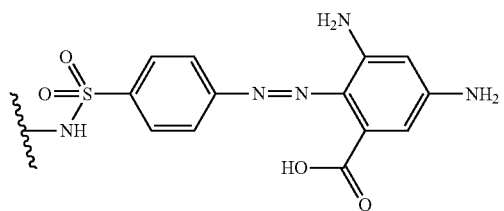 [SMILES: *NS(=O)(=O)c1ccc(N=Nc2c(N)cc(N)cc2C(=O)O)cc1] |
| 43 | 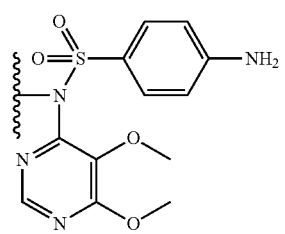 [SMILES: *N(c1ncnc(OC)c1OC)S(=O)(=O)c1ccc(N)cc1] |
| 44 | 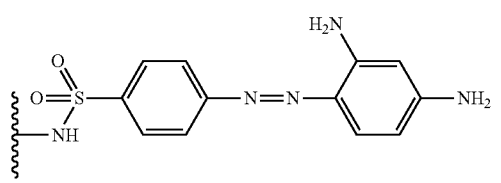 [SMILES: *NS(=O)(=O)c1ccc(N=Nc2ccc(N)cc2N)cc1] |
| 45 | 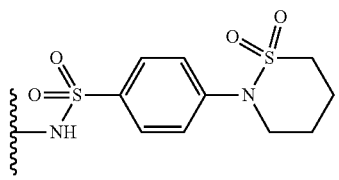 [SMILES: *NS(=O)(=O)c1ccc(N2CCCCS2(=O)=O)cc1] |
| 46 | 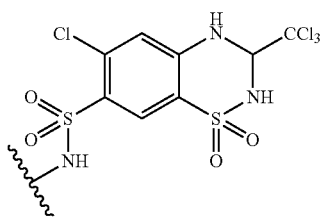 |
| 47 | 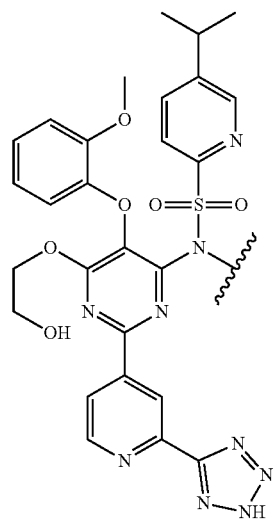 [SMILES: *N(c1nc(-c2ccnc(-c3nn[nH]n3)c2)nc(OCCO)c1Oc1ccccc1OC)S(=O)(=O)c1ccc(C(C)C)cn1] |
TABLE 11-continued
| 48 | 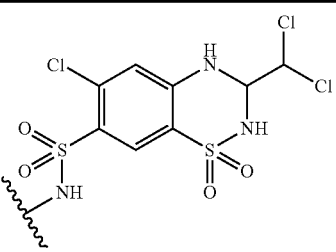 |
| 49 | 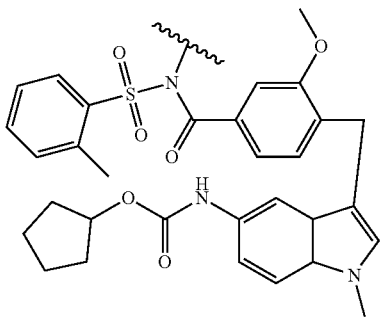 [SMILES: *N(C(=O)c1ccc(CC2=CN(C)C3C=CC(NC(=O)OC4CCCC4)=CC23)c(OC)c1)S(=O)(=O)c1ccccc1C] |
| 50 | 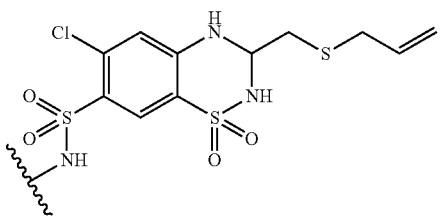 [SMILES: *NS(=O)(=O)c1cc2c(cc1Cl)NC(CSCC=C)NS2(=O)=O] |
| 51 | 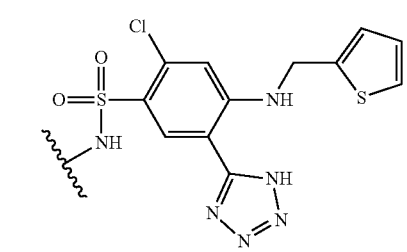 [SMILES: *NS(=O)(=O)c1cc(-c2nnn[nH]2)c(NCc2cccs2)cc1Cl] |
| 52 | 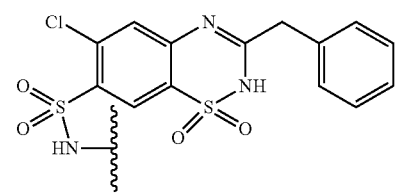 [SMILES: *NS(=O)(=O)c1cc2c(cc1Cl)N=C(Cc1ccccc1)NS2(=O)=O] |
| 53 | 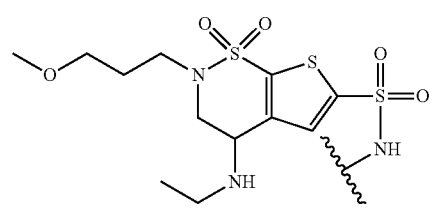 [SMILES: *NS(=O)(=O)c1cc2c(s1)S(=O)(=O)N(CCCOC)CC2NCC] |
| 54 | 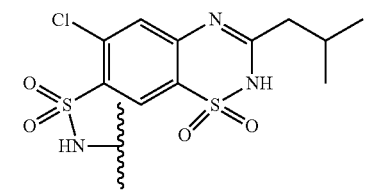 [SMILES: *NS(=O)(=O)c1cc2c(cc1Cl)N=C(CC(C)C)NS2(=O)=O] |

TABLE 11-continued
| | | | | |
|---|---|---|---|---|
| 55 | 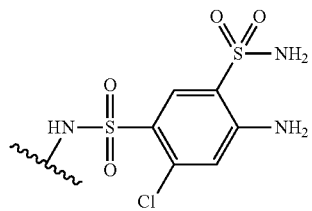 [SMILES: *NS(=O)(=O)c1cc(S(N)(=O)=O)c(N)cc1Cl] | | 63 | 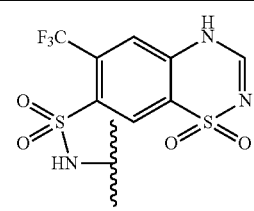 |
| 56 | 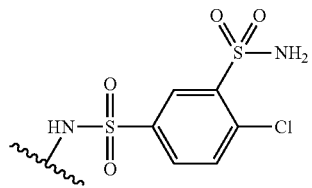 [SMILES: *NS(=O)(=O)c1ccc(Cl)c(S(N)(=O)=O)c1] | | 64 | 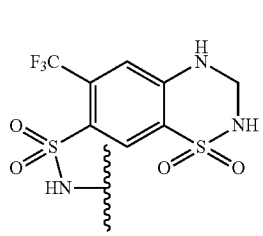 |
| 57 | 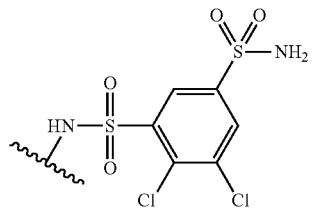 [SMILES: *NS(=O)(=O)c1cc(S(N)(=O)=O)cc(Cl)c1Cl] | | 65 | 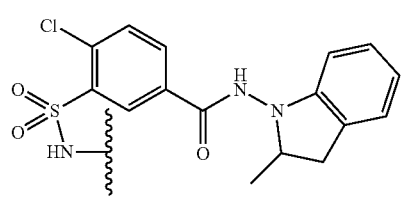 |
| 58 | 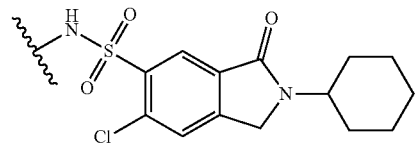 [SMILES: *NS(=O)(=O)c1cc2c(cc1Cl)CN(C1CCCCC1)C2=O] | | 66 | 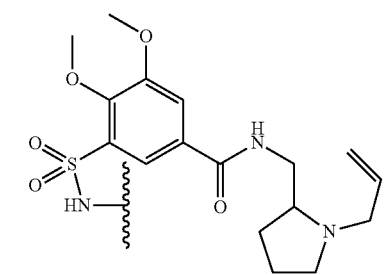 |
| 59 | 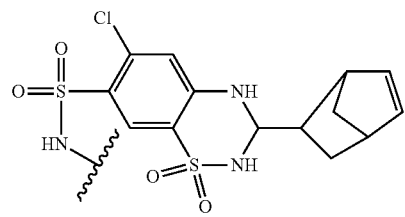 [SMILES: *NS(=O)(=O)c1cc2c(cc1Cl)NC(C1CC3C=CC1C3)NS2(=O)=O] | | 67 | 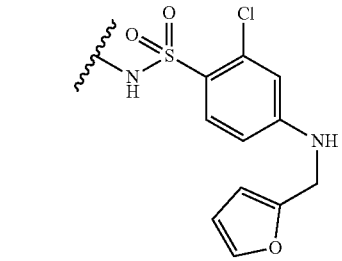 |
| 60 | 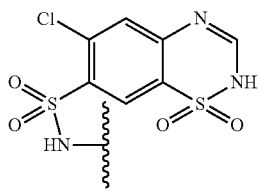 [SMILES: *NS(=O)(=O)c1cc2c(cc1Cl)N=CNS2(=O)=O] | | | |
| 61 | 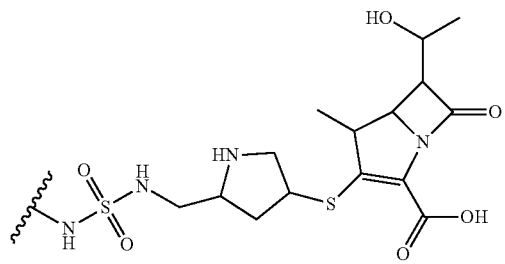 [SMILES: *NS(=O)(=O)NCC1CC(SC2=C(C(=O)O)N3C(=O)C(C(C)O)C3C2C)CN1] | | 68 | 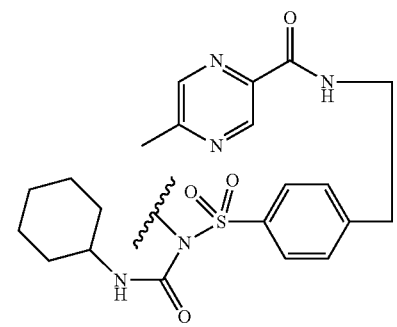 |
| 62 | 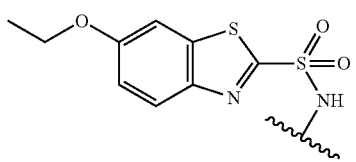 [SMILES: *NS(=O)(=O)c1nc2ccc(OCC)cc2s1] | | | |

TABLE 11-continued

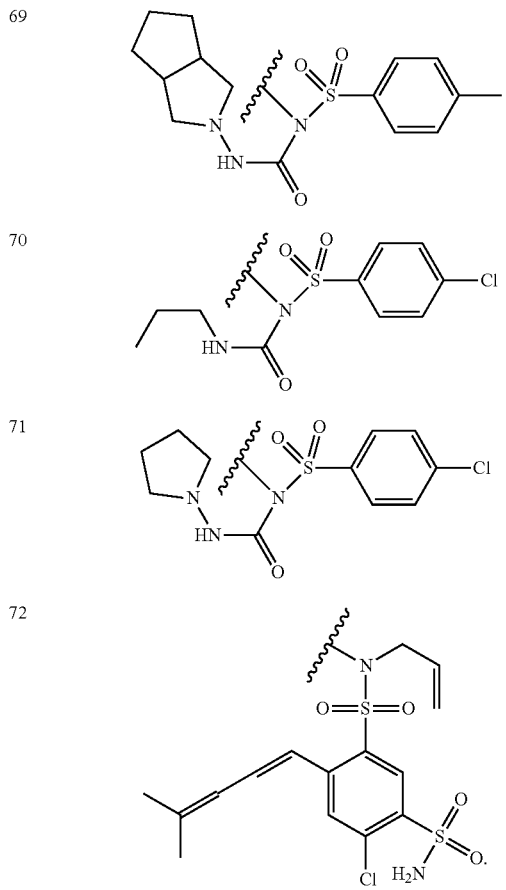

Prodrugs of Tertiary Amine Containing Parent Drugs

In some embodiments, the invention relates to a prodrug conjugates having the Formula V:

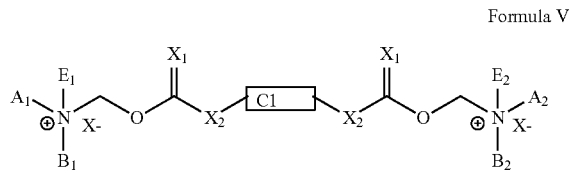

Formula V wherein $A_1$, $B_1$ and $E_1$ together with the nitrogen they are attached to form a tertiary amine containing first biologically active molecule;

$A_2$, $B_2$ and $E_2$ together with the nitrogen they are attached to form a tertiary amine containing second biologically active molecule;

$X_1$ is selected from O or S;

$X_2$ is selected from direct bond, O, S or $NR_{20}$ wherein $R_{20}$ is selected from hydrogen, halogen, aliphatic, substituted aliphatic, aryl or substituted aryl;

X— is a pharmaceutically acceptable counterion; and,

C1 represents a carrier moiety.

In some embodiments, the invention relates to a prodrug conjugates having the Formula VI:

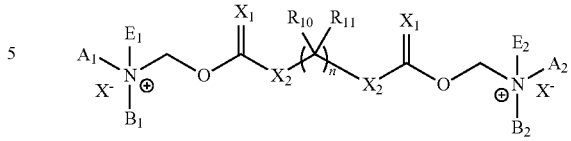

Formula VI wherein n is an integer between 1 and 50;

n, $A_1$, $E_1$, $B_1$, $A_2$, $E_2$, $B_2$, $X_1$, $X_2$, $R_{10}$, $R_{11}$ and X— are as defined above.

In some embodiments, n is selected from 4, 5, 6, 7, 8, 9, 10, 11, 12, 13, 14, 15, 16, 17, 18, 19, 20, 21, 22, 23, 24, 25, 26, 27, 28, 29 and 30.

In some embodiments, the invention relates to a prodrug conjugates having the Formula VII:

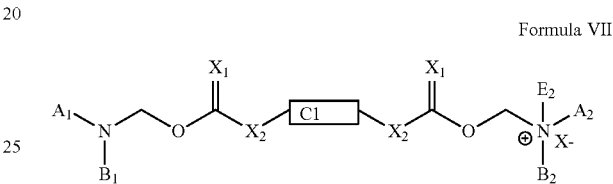

Formula VII n, $A_1$, $B_1$, $A_2$, $E_2$, $B_2$, $X_1$, $X_2$, and X— are as defined above.

The tertiary amine-containing parent drug may be any tertiary amine-containing drug that induces a desired local or systemic effect. Such drugs include broad classes of compounds. In general, this includes: analgesic agents; anesthetic agents; antiarthritic agents; respiratory drugs, including antiasthmatic agents; anticancer agents, including antineoplastic agents; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; gastrointestinal (GI) motility agents; herbal remedies; hormones; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids; sympathomimetics; tranquilizers; and vasodilators including general coronary, peripheral and cerebral.

Examples of tertiary amine-containing antibiotic parent drugs from which the prodrugs of the invention may be derived include: clindamycin, ofloxacin/levofloxacin, pefloxacin, quinupristine, rolitetracycline, and cefotiam.

Examples of tertiary amine-containing antifungal parent drugs from which the prodrugs of the invention may be derived include: butenafine, naftifine, and terbinafine.

Examples of tertiary amine-containing antimalarials and antiprotozoals parent drugs from which the prodrugs of the invention may be derived include: amodiaquine, quinacrine, sitamaquine, quinine.

Examples of tertiary amine-containing HIV protease inhibitor parent drugs from which the prodrugs of the invention may be derived include: saquinavir, indinavir, atazanavir and nelfinavir. Anti-HIV drugs also include maraviroc and aplaviroc for inhibition of HIV entry.

Examples of tertiary amine-containing anticonvulsants/antispasmodics parent drugs from which the prodrugs of the invention may be derived include: atropine, darifenancin; dicyclomine; hyoscayamine, tiagabine, flavoxate; and alverine.

Examples of tertiary-amine containing antidepressant parent drugs from which the prodrugs of the invention are derived include: amitriptyline, adinazolam, citalopram, cotinine, clomipramine, doxepin, escitalopram, femoxetine, imipramine, minaprine, moclobemide, mianserin, mirtazapine, nefazodone, nefopam, pipofenazine, promazine, ritanserin, trazodone, trimipramine and venlafaxine.

Examples of tertiary amine-containing antiemetic parent drugs from which the prodrugs of the invention are derived include: aprepitant, buclizine, cilansetron, cyclizine, dolasetron, granisetron, meclizine, ondansetron, palonosetron, ramosetron, thiethylperazine, trimethobenzamide, scopolamine, and prochlorperazine.

Examples of tertiary amine-containing antihistamine parent drugs from which the prodrugs of the invention are derived include: acetprometazine, azatadine, azelastine, brompheniramine, carbinoxamine, chlorpheniramine, clemastine, dexobrompheniramine, diphenhydramine, diphenylpyraline, doxepin, emadastine, loratadine, mequitazine, olopatadine, phenindamine, pheniramine, promethazine, tripelennamine, triprolidine, astemizole, cetirizine, fexofenadine, terfenadine, latrepirdine, ketotifen, cyproheptadine, hydroxyzine, clobenzepam doxylamine, cinnarizine, orphenadrine.

Examples of tertiary amine-containing antiparkinsonian parent drugs from which the prodrugs of the invention are derived include: cabergoline, ethopropazine, pergolide, selegiline, metixene, biperiden, cycrimine, procycladine and apomorphine.

Examples of tertiary amine-containing antipsychotic parent drugs from which the prodrugs of the invention are derived include: acetophenazine, amisulpride, aripiprazole, bifeprunox, blonanserin, cariprazine, carphenazine, clopenthixol, clozapine, dehydro aripiprazole, someperidone, droperidol, flupenthixol, fluphenazine, fluspirilene, haloperidol, iloperidone, lurasidone, mesoridazine, molindole, nemanopride, olanzapine, perospirone, perphenazine, PF-00217830 (Pfizer), pipotiazine, propericiazine, quetiapine, remoxipride, risperidone, sertindole, SLV-313 (Solvay/Wyeth), sulpiride, thioproperazine, thioridazine, thiothixene, trifluoperazine, ziprasidone, zotepine, pimozide, benzquinamide, triflupromazine, tetrabenazine, melperon, asenapine, chlorprothixene, spiperone and chlorpromazine.

Examples of tertiary amine-containing anxiolytic parent drugs from which prodrugs of the invention are derived include: buspirone, and loxapine.

Examples of tertiary amine-containing nootroopic (memory and cognitive enhancers) parent drugs from which prodrugs of the invention are derived include: donepezil, galantamine, latrepirdine, nicotine, TC-5616 (Targacept, Inc.) having the IUPAC name: N-[(2S,3S)-2-(pyridin-3-ylmethyl)-1-azabicyclo[2.2.2]oct-3-yl]-1-benzofuran-2-carboxamide.

Examples of tertiary amine-containing parent drugs for erectile dysfunction from which prodrugs of the invention are derived include: apomorphine and sildenafil.

Examples of tertiary amine-containing parent drugs for migraine headache from which prodrugs of the invention are derived include: almotriptan, naratriptan, rizatriptan, sumatriptan, zolmitriptan, dihydroergotamine, ergotamine, eletripan and lisuride.

Examples of tertiary amine-containing parent drugs for the treatment of alcoholism from which prodrugs of the invention are derived include: naloxone and naltrexone. Other narcotic antagonist amine containing parent drugs for treatment of substance abuse from which prodrugs of the invention are derived include: levallorphan, nalbuphine, nalorphine and nalmefene.

Examples of a tertiary amine-containing parent drug for the treatment of addiction from which a prodrug of the invention is derived include: buprenorphine, isomethadone, levomethadyl acetate, methadyl acetate, nor-acetyl levomethadol, and normethadone.

Examples of tertiary amine-containing muscle relaxant parent drugs from which prodrugs are derived include: cyclobenzaprine, nefopam, tolperisone, orphenadrine, and quinine.

Examples of tertiary amine-containing nonsteroidal antiinflammatory parent drugs from which prodrugs of the invention are derived include: etodolac, meloxicam, ketorolac, lornoxicam and tenoxicam. Examples of tertiary amine-containing opioid parent drugs from which prodrugs of the invention are derived include alfentanil, anileridine, buprenorphine, butorphanol, clonitazene, codeine, dihydrocodeine, dihydromorphin, fentanyl, hydromorphone, meperidine, metazocine, methadone, morphine, oxycodone, hyrdocodone, oxymorphone, pentazocine, remifentanil, and sufentanil.

Examples of other tertiary amine-containing analgesic parent drugs from which prodrugs of the invention are derived include: methotrimeprazine, tramadol, nefopam, phenazocine, propiram, quinupramine, thebaine and propoxyphene.

Examples of tertiary amine-containing sedatives/hypnotics from which the prodrugs of the invention may be derived include: eszopiclone, flurazepam, propiomazine, and zopiclone.

Examples of tertiary amine-containing local analgesic parent drugs from which prodrugs of the invention are derived include: bupivacaine, dexmedetomidine, dibucaine, dyclonine, lodicaine, mepivacaine, procaine, and tapentadol and ropivacaine.

Examples of tertiary amine-containing antianginals from which the prodrugs of the invention may be derived include: ranozaline, bepridil.

Examples of tertiary amine-containing antiarrhythmics from which the prodrugs of the invention may be derived include: amiodarone, aprindine, encainide, moricizine, procainamide, diltiazem, verapamil, bepridil.

Examples of tertiary amine-containing antihypertensives from which the prodrugs of the invention may be derived include: azelnidipine, deserpidine, ketanserin, reserpine, and sildenafil.

Examples of tertiary amine-containing antithrombotics from which the prodrugs of the invention may be derived include: clopidogrel and ticlopidine.

Examples of tertiary amine-containing antineoplastic parent drugs from which prodrugs of the invention are derived include: dasatinib, flavopiridol, gefitinib, imatinib, sunitinib, topotecan, vinblastine, vincristine, fincesine, vinorelbine, vinorelbine, tamoxifen, tremifene, and tesmilifene.

Examples of tertiary amine-containing drugs parent drugs for use in treating irritable bowel syndrome (IBS) from which the prodrugs of the invention are derived include asimadoline.

Examples of other tertiary amine-containing parent drugs from which the prodrugs of the invention are derived include: antimuscarinics and anticholinergics such as benzotropine, procyclidine and trihexylphanidyl; alpha andrenergic blockers such as dapiprazole, dexmedetomidine and nicergoline; anorexics such as diethylpropian, benzapehtamine, phendimetrazine, and sibutramine; antidiarrhels such as diphenoxylate and loperamide, antikinetic and antihypertensives such as clonidine; antiosteoporotics such as raloxifene; antipruritics such as methyldilazine; antitussives such as dextromethorphan; antiulceratives such as pirenzepine; cholinesterase inhibitors such as galantamine; gastroprokinetics such as alvimopan, cisapride, and piboserod; miglustat for treating glycosphingolipid lysosomal storage disorder; clomifene as gonad stimulating prinicipal; neuromuscular blockers such as dihydro-beta-erythrodoidine, niotropics such as rivastigmine, oxytocics such as methylergonovine; antiametics such as chloroquine; respiratory stimulants such as doxapram; muscarinic receptor antagonists for treating urinary incontinence such as oxybutynin and solifenacin; calcium channel blockers such as flunarizine; anthelmintics such as diethylcarbamazine and quinacrine; miotics such as physostigmine; neuroprotectives such as lubeluzole; immunosuppressants such as mycophenolate mofetil; and stimulants such as nicotine.

Preferred tertiary amine-containing parent drugs from which prodrugs of the invention are derived include: amisulpride, aripiprazole, asenapine, cariprazine, citalopram, dehydroaripiprazole, escitalopram, galantamine, iloperidone, latrepirdine, olanzapine, paliperidone, perospirone, risperidone, and ziprasidone.

The present invention is intended to encompass any parent drug compound or any substituted parent drug compound which contains a tertiary amine group and which is biologically active and can be derivatized according to the present invention to afford the corresponding prodrugs. While the tertiary amine-containing parent drugs from which the prodrugs of the invention may be derived are numerous, many of the chemical structures of the prodrugs of the invention can be characterized by certain general structure types. One type includes those wherein the tertiary amine nitrogen is part of a cyclic (including bicyclic or tricyclic) aliphatic group such as piperidine, piperazine, morpholine, pyrrolidine, azapine, and diazapine. Another type includes those wherein the tertiary amine nitrogen is part of an alkyl amine group such as a diethyl and/or dimethyl amine.

In some embodiments, the invention relates to a prodrug conjugates having the Formula VIII:

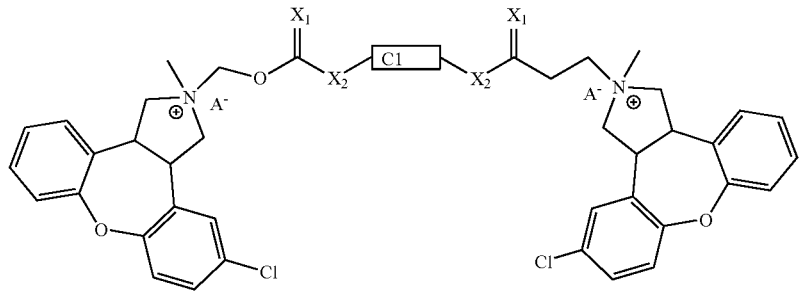

Formula VIII wherein A- is a pharmaceutically acceptable counterion; and $X_1$, and $X_2$, are as defined above.

In one embodiment, the parent drug moieties (APIs) are independently selected from Table 12. In one embodiment, the prodrug is a compound of Formula II wherein API-1 and API-2 are selected from Table-12. In one embodiment both API-1 and API-2 represent the same parent drug.

TABLE 12

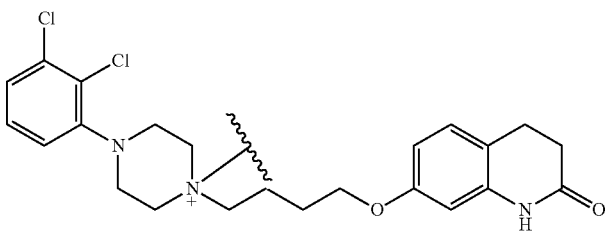 [SMILES: *[N+]1(CCCCOc2ccc3c(c2)NC(=O)CC3)CCN(c2cccc(Cl)c2Cl)CC1]

TABLE 12-continued
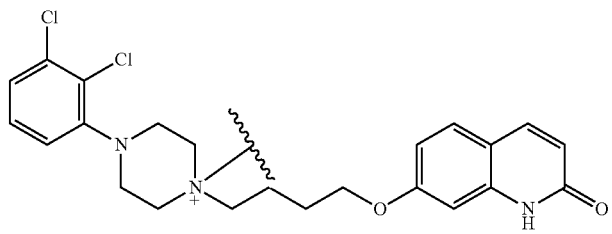 [SMILES: *[N+]1(CCCCOc2ccc3ccc(=O)[nH]c3c2)CCN(c2cccc(Cl)c2Cl)CC1]
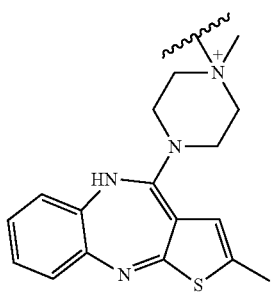
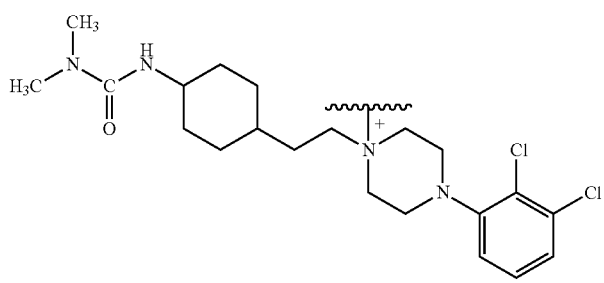
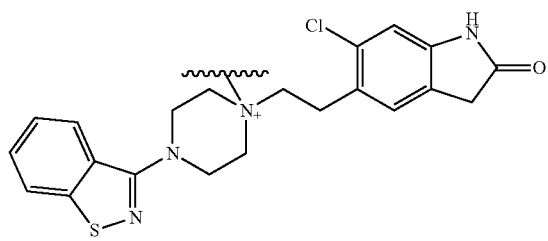 [SMILES: *[N+]1(CCc2cc3c(cc2Cl)NC(=O)C3)CCN(c2nsc3ccccc23)CC1]
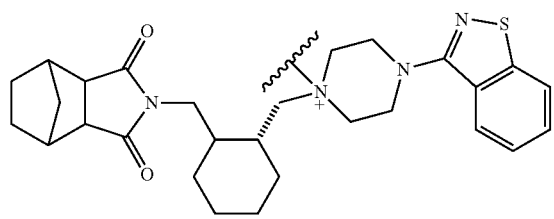 [SMILES: *[N+]1(C[C@@H]2CCCCC2CN2C(=O)C3C4CCC(C4)C3C2=O)CCN(c2nsc3ccccc23)CC1]
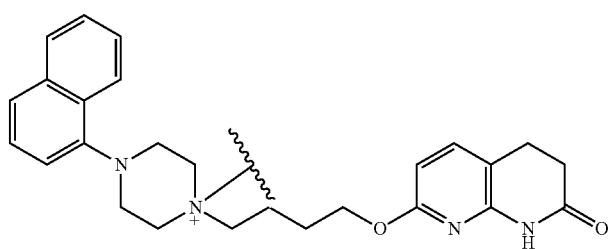 [SMILES: *[N+]1(CCCCOc2ccc3c(n2)NC(=O)CC3)CCN(c2cccc3ccccc23)CC1]

TABLE 12-continued
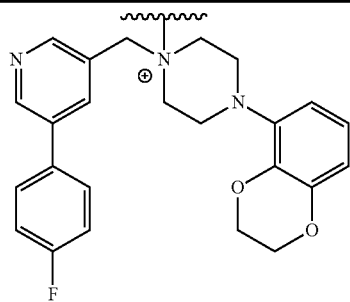
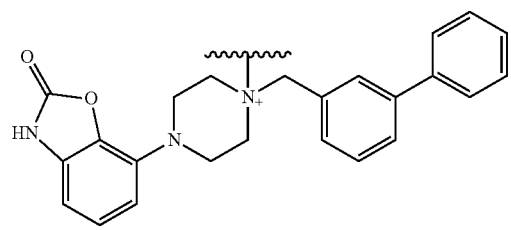 [SMILES: *[N+]1(Cc2cccc(-c3ccccc3)c2)CCN(c2cccc3[nH]c(=O)oc23)CC1]
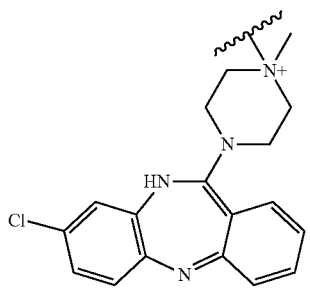 [SMILES: *[N+]1(C)CCN(C2=c3ccccc3=Nc3ccc(Cl)cc3N2)CC1]
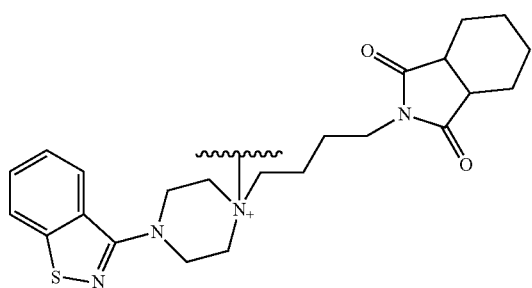 [SMILES: *[N+]1(CCCCN2C(=O)C3CCCCC3C2=O)CCN(c2nsc3ccccc23)CC1]
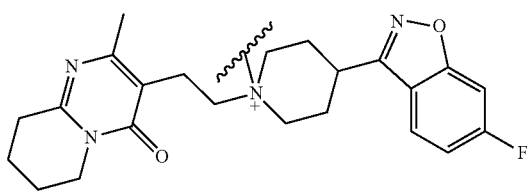 [SMILES: *[N+]1(CCc2c(C)nc3n(c2=O)CCCC3)CCC(c2noc3cc(F)ccc23)CC1]
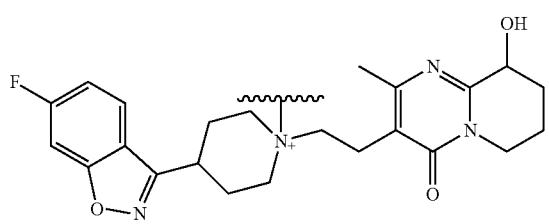 [SMILES: *[N+]1(CCc2c(C)nc3n(c2=O)CCCC3O)CCC(c2noc3cc(F)ccc23)CC1]

TABLE 12-continued
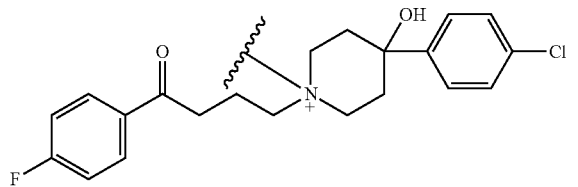 [SMILES: *[N+]1(CCCC(=O)c2ccc(F)cc2)CCC(O)(c2ccc(Cl)cc2)CC1]
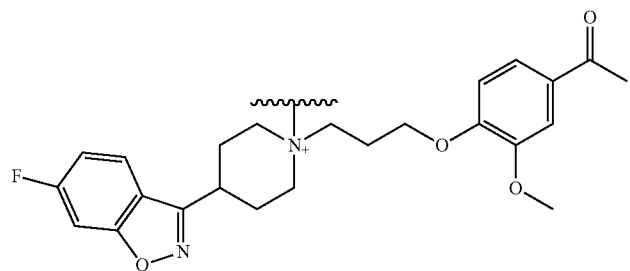 [SMILES: *[N+]1(CCCOc2ccc(C(C)=O)cc2OC)CCC(c2noc3cc(F)ccc23)CC1]
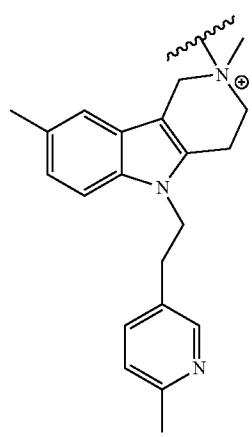 [SMILES: *[N+]1(C)CCc2c(c3cc(C)ccc3n2CCc2ccc(C)nc2)C1]
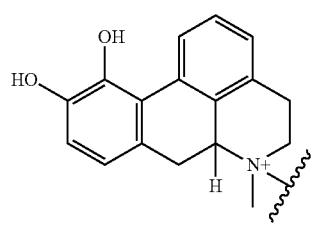 [SMILES: *[N+]1(C)CCc2cccc3c2C1Cc1ccc(O)c(O)c1-3]
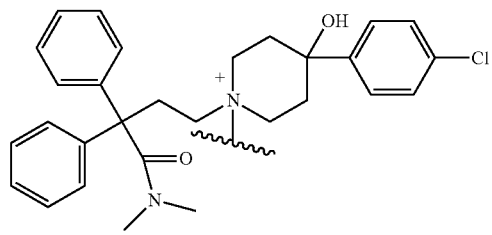
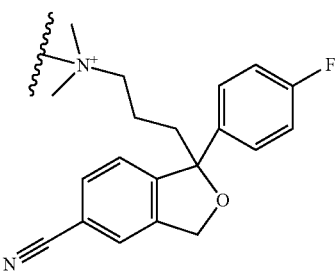 [SMILES: *[N+](C)(C)CCCC1(c2ccc(F)cc2)OCc2cc(C#N)ccc21]

TABLE 12-continued
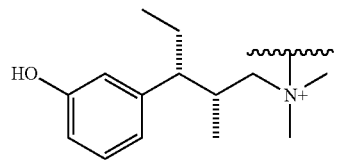 [SMILES: *[N+](C)(C)C[C@H](C)[C@@H](CC)c1cccc(O)c1]
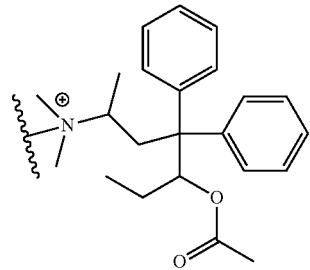 [SMILES: *[N+](C)(C)C(C)CC(c1ccccc1)(c1ccccc1)C(CC)OC(C)=O]
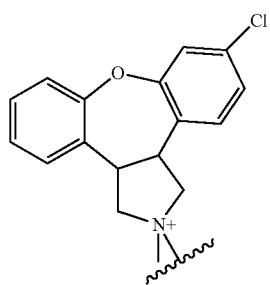 [SMILES: *[N+]1(C)CC2c3ccccc3Oc3cc(Cl)ccc3C2C1]
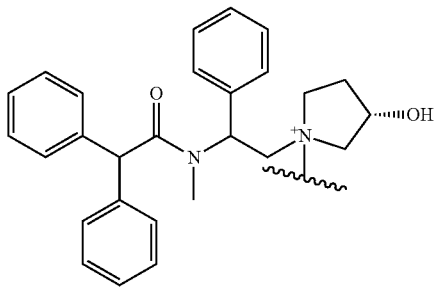 [SMILES: *[N+]1(CC(c2ccccc2)N(C)C(=O)C(c2ccccc2)c2ccccc2)CC[C@H](O)C1]
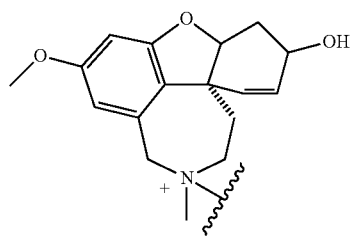
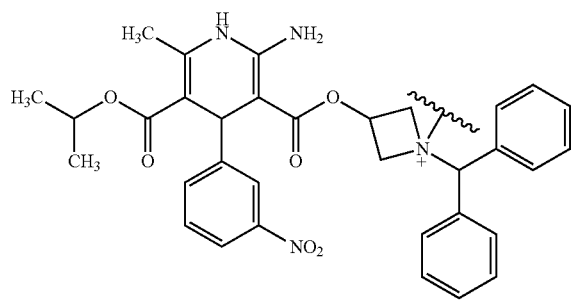 [SMILES: *[N+]1(C(c2ccccc2)c2ccccc2)CC(OC(=O)C2=C(N)NC(C)=C(C(=O)OC(C)C)C2c2cccc([N+](=O)[O-])c2)C1]

Prodrugs of Heteroaryl Parent Drugs

In one embodiment, the compounds suitable for use in the methods of the invention are derivatives of heteroaryl NH-containing parent drugs that are substituted at the NH nitrogen atom with labile prodrug moieties. Preferably, the prodrug moieties are hydrophobic and reduce the solubility at physiological pH (pH 7.0), as well as modulate polarity and lipophilicity parameters of the prodrug as compared to the parent drug.

In one embodiment, the invention provides a prodrug compound of Formula IX:

Formula IX

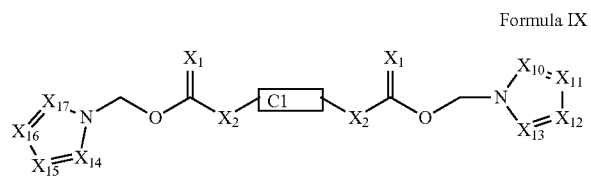

or a pharmaceutically acceptable salt thereof, wherein each of $X_{10}$ to $X_{17}$ is independently N or CR, provided that at least one of $X_{10}$-$X_{17}$ is CR. The R groups combine to form the portion of the prodrug compound in addition to the five-membered heteroaromatic ring. For example, the R groups can be independently hydrogen, optionally substituted aliphatic, aromatic, heteroaromatic or a combination thereof. The R groups can also be taken together with the carbon atoms to which they are attached to form one or more optionally substituted fused ring systems.

In a preferred embodiment, the invention relates to a prodrug conjugate of Formula X:

Formula X

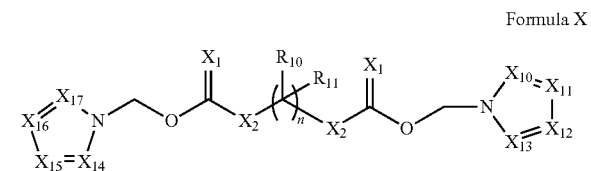

wherein, n, $X_{10}$-$X_{17}$, $X_1$, $X_2$, $R_{10}$, and $R_{11}$ are as defined above.

Heteroaromatic NH-containing parent drugs include broad classes of compounds. In general, this includes: analgesic agents; anesthetic agents; antiarthritic agents; respiratory drugs, including antiasthmatic agents; anticancer agents, including antineoplastic agents; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; nootropics; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; opioid agonists; nicotine; nutritional agents, such as vitamins, essential amino acids and fatty acids; ophthalmic drugs such as antiglaucoma agents; parasympatholytics; peptide drugs; psychostimulants; sedatives; steroids; sympathomimetics; tranquilizers; and vasodilators including general coronary, peripheral and cerebral.

Specific heteroaromatic NH-containing parent drugs represent a variety of drug classes. Such drugs include tranquilizers and sedatives, such as mepiprazole and dexmedetomidine; anthelmintic agents, such as albendazole, carbendazole, cyclobendazole, mebendazole and thiabendazole; antimigraine agents, such as almotriptan, dolasetron, eletriptan, lisuride, naratriptan, rizatriptan, sumatriptan, frovatriptan, zolmitriptan and ergotamine; treatments for irritable bowel syndrome, such as alosetron; antiviral agents, such as delavirdine and atevirdine; antihypertensive agents, such as bopindolol, bucindolol, candesartan, deserpidine, mibefradil, ergoloid mesylate, indoramin, irbesartan, mepindolol, olmesartan, reserpine, rescinnamine, losartan, tasosartan, valsartan, raubasine, syrosingopine, carmoxirole and rescimetol; anti-Parkinson agents, such as cabergoline, pergolide, bromocriptine and terguride; bronchodilators, such as ambuphylline; antiulcerative agents, such as cimetidine, lansoprazole, omeprazole, pantaprozole and rabeprazole; antibacterial agents, such as cefatrizine and daptomycin; oxytocic agents, such as ergonovine and methylergonovine; analgesics, such as etodolac; antineoplastic agents, such as liarozole, pemetrexed, thiamiprine, vinblastine, vincristine, vindesine, vinorelbine, voacamine and venflunine; antidepressants, such as oxypertine, indalpine and roxindole; antiallergic agents, such as pemirolast, tazanolast and traxanox; cardiotonic agents, such as pimobendan and sulmazole; antiasthmatics, such as pranlukast; antiemetics, such as ramosetron, tropisetron and alizapride; vasodilators, such as bendazole and tadalafil; anti-gout agents, such as allopurinol; antirheumatic agents, such as azathioprine; mydriatics, such as yohimbine; therapies for congestive heart failure, such as conivaptan; and hormonal agents, such as adrenoglomerulotropin, octreotide, somatostatin, exenatide, teriparatide, leuprorelin and goserelin.

In one embodiment, the parent drug is a peptide comprising at least one heteroaromatic NH group. Such peptides include peptides comprising from 2 to about 50, from 2 to about 40, from 2 to about 20 or from 2 to about 12 amino acid residues, including at least one residue selected from tryptophan and histidine. Suitable peptides include, but are not limited to, thyrotropin releasing hormone (TRH), exenatide, daptomycin, octreotide, somatostatin, teriparatide, leuprorelin and goserelin.

While the heteroaromatic NH-containing parent drugs from which the prodrugs of the invention may be derived are numerous, many of the chemical structures of the prodrugs of the invention can be characterized by certain general structure types. One type includes compounds wherein the heteroaromatic group is a pyrrole group. Another type includes compounds wherein the heteroaromatic group is an imidazole group. Another type includes compounds wherein the heteroaromatic group is a 1,2,3- or 1,2,4-triazole group. Another type includes compounds wherein the heteroaromatic group is a tetrazole group. Another type includes compounds wherein the heteroaromatic group is a benzimidazole group. Another type includes compounds wherein the heteroaromatic group is an indole group. Another type includes compounds wherein the heteroaromatic group is a pyrazole group.

Benzimidazole-containing parent drugs which can be modified to produce prodrugs of the invention include albenazole, carbendazole, cyclobendazole, lansoprazole, liarozole, mebendazole, mizolastine, omeprazole, pantaprazole, pimobendan, rabeprazole, thiabendazole, bendazol and mibepradil. Preferred benzimidazole-containing drugs include lansoprazole, mibefradil and pimobendan.

Imidazole-containing parent drugs which can be modified to produce prodrugs of the invention include alosetron, ambuphylline, cimetidine, conivaptan, dexmedetomidine, ramosetron, thiamiprine, sulmazole, azathioprine, exenatide, teriparatide, thyrotropin releasing hormone (TRH), goserelin and leuprorelin. Preferred imidazole-containing drugs include conivaptan, sulmazole and azathioprine.

Indole-containing parent drugs which can be modified to produce prodrugs of the invention include almotriptan, atevirdine, bopindolol, bromocriptine, bucindolol, cabergoline, delavirdine, deserpidine, dolasetron, eletriptan, ergoloid mesylate, ergonovine, etodolac, frovatriptan, indoramin, lisuride, mepidolol, methylergonovine, naratriptan, oxypertine, pemetrexed, pergolide, rescinnamine, reserpine, rizatriptan, sumatriptan, tadalafil, tropisetron, adrenoglomerulotriptan, bromocriptine, ergotamine, indalpine, raubasine, reserpiline, roxindole, syrosingopine, terguride, vinblastine, vincristine, vindesine, vinorelbine, voacamine, vinflunineatevirdine, carmoxirole, rescimetol, yohimbine, zolmitriptan, octreotide, somatostatin, exenatide, teriparatide, daptomycin, leuprorelin and goserelin. Preferred indole-containing drugs include bopindolol, bucindolol, cabergoline, dolasetron, indoramin, oxypertine, pergolide, rescinnamine, reserpine, atevirdine, carmoxirole and rescimetol.

Pyrazole-containing parent drugs which can be modified to produce prodrugs of the invention include mepiprazole and allopurinlol.

Tetrazole-containing parent drugs which can be modified to produce prodrugs of the invention include candesartan, irbesartan, losartan, olmesartan, pemirolast, pranlukast, tasosartan, traxanox and valsartan.

Triazole-containing parent drugs which can be modified to produce prodrugs of the invention include cefatrizine and alizapride.

Particularly preferred parent drugs which can be modified according to the invention include bopindolol, bucindolol, cabergoline, candesartan, cefatrizine, conivaptan, indoramin, irbesartan, lansoprazole, mibefradil, olmesartan, oxypertine, pemirolast, pergolide, pimobendan, rescinnamine, reserpine, valsartan, sulmazole, azathioprine, atevirdine, carmoxirole and rescimetol.

In one embodiment, the parent drug moieties (APIs) are selected from Table 13. In one embodiment, the prodrug is a compound of Formula II wherein API-1 and API-2 are selected from Table 13. In one embodiment both API-1 and API-2 represent the same parent drug.

TABLE 13

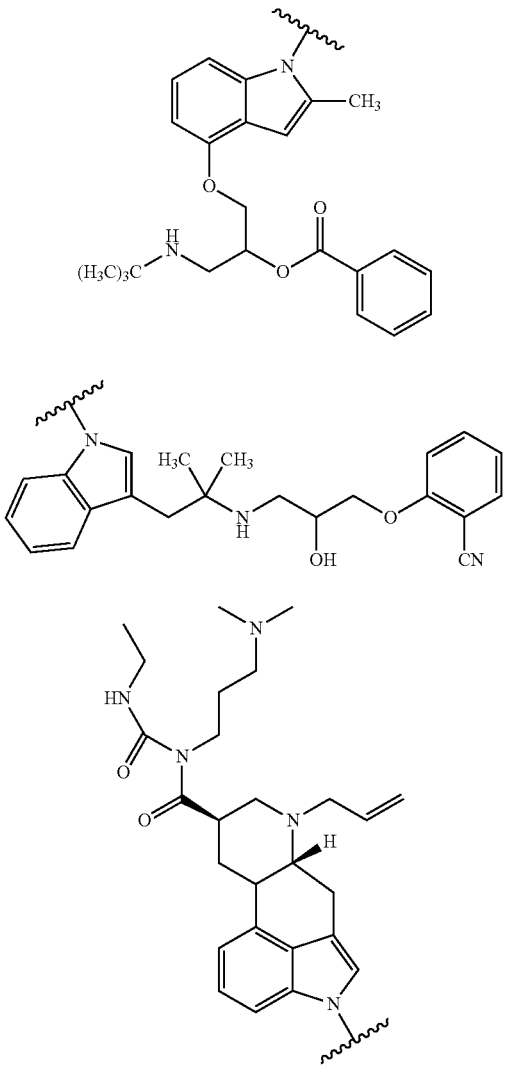

TABLE 13-continued
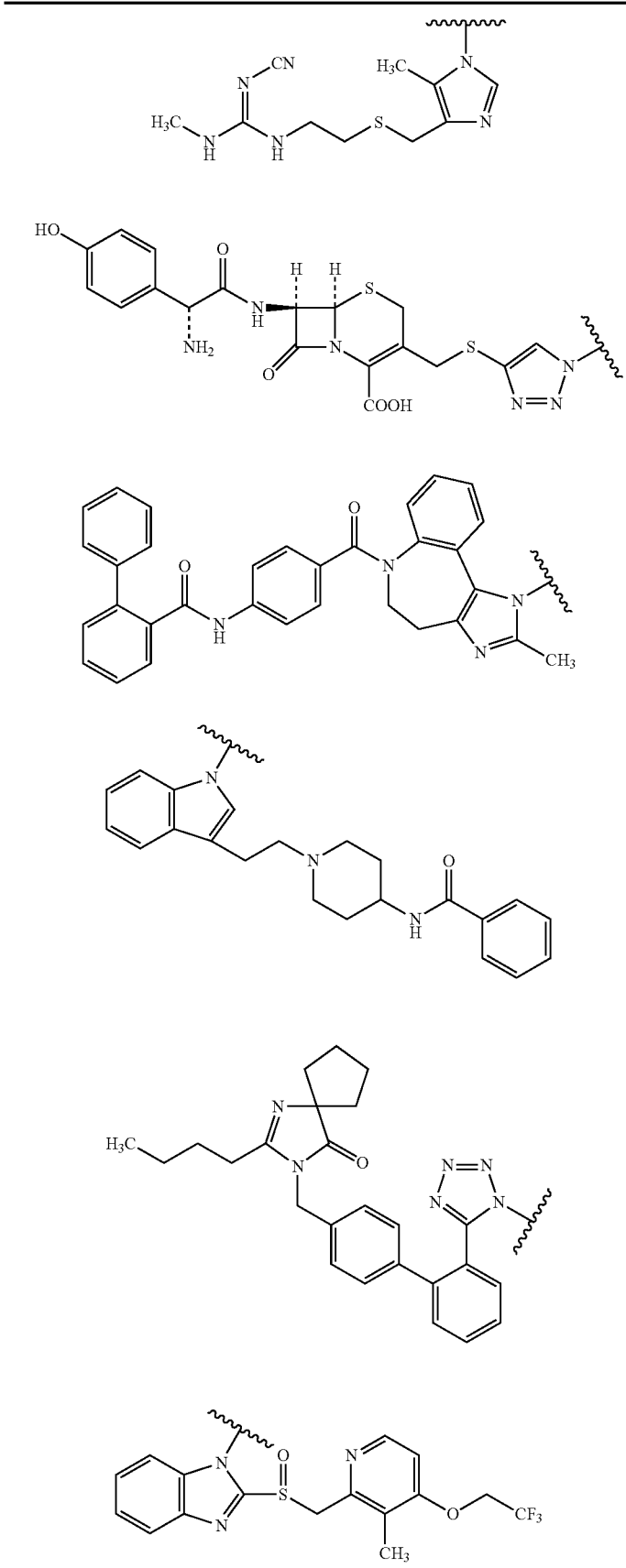

TABLE 13-continued
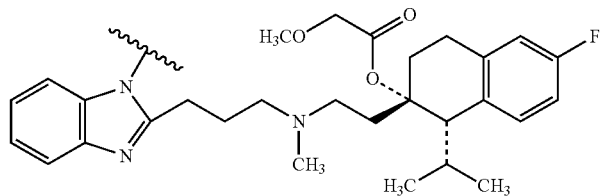 [SMILES: *n1c(CCCN(C)CC[C@@]2(OC(=O)COC)CCc3cc(F)ccc3[C@@H]2C(C)C)nc2ccccc21]
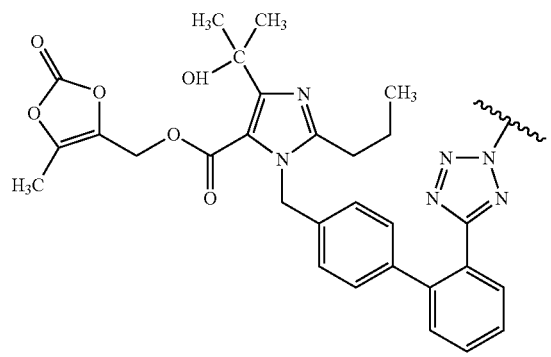 [SMILES: *n1nnc(-c2ccccc2-c2ccc(Cn3c(CCC)nc(C(C)(C)O)c3C(=O)OCc3oc(=O)oc3C)cc2)n1]
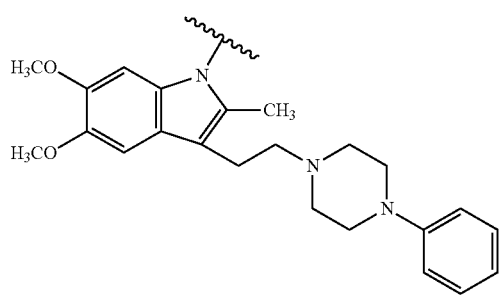 [SMILES: *n1c(C)c(CCN2CCN(c3ccccc3)CC2)c2cc(OC)c(OC)cc21]
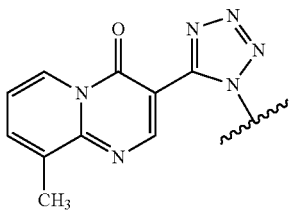 [SMILES: *n1nnnc1-c1cnc2c(C)cccn2c1=O]
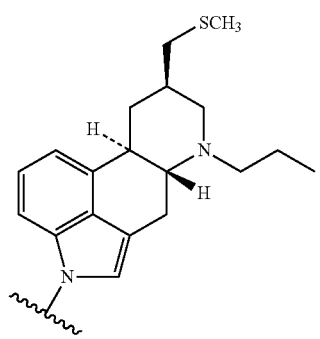 [SMILES: *n1cc2c3c(cccc31)[C@H]1C[C@@H](CSC)CN(CCC)[C@@H]1C2]
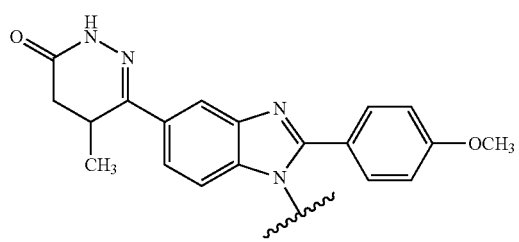 [SMILES: *n1c(-c2ccc(OC)cc2)nc2cc(C3=NNC(=O)CC3C)ccc21]

TABLE 13-continued
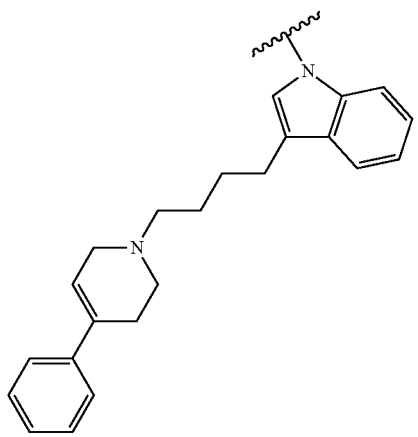 [SMILES: *n1cc(CCCCN2CC=C(c3ccccc3)CC2)c2ccccc21]
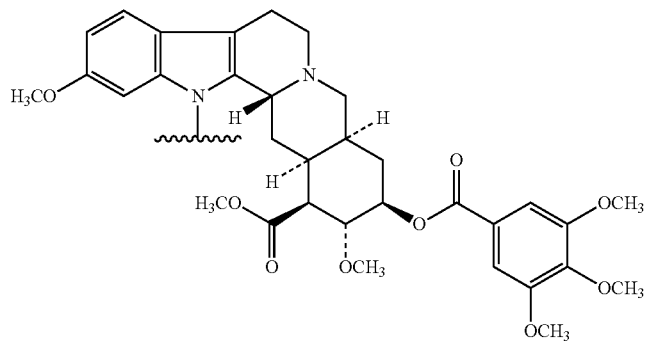 [SMILES: *n1c2c(c3ccc(OC)cc31)CCN1C[C@H]3C[C@@H](OC(=O)c4cc(OC)c(OC)c(OC)c4)[C@H](OC)[C@@H](C(=O)OC)[C@H]3C[C@H]21]
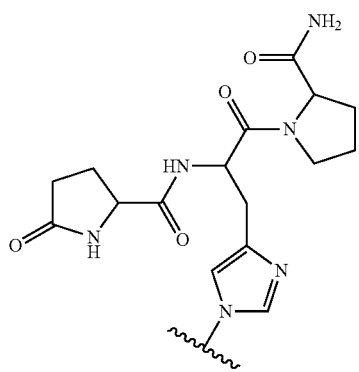 [SMILES: *n1cnc(CC(NC(=O)C2CCC(=O)N2)C(=O)N2CCCC2C(N)=O)c1]
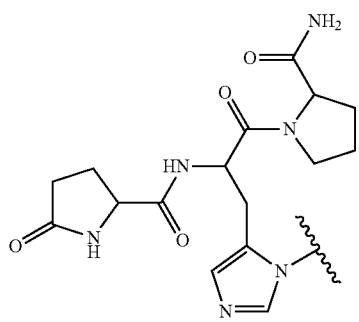 [SMILES: *n1cncc1CC(NC(=O)C1CCC(=O)N1)C(=O)N1CCCC1C(N)=O]

TABLE 13-continued
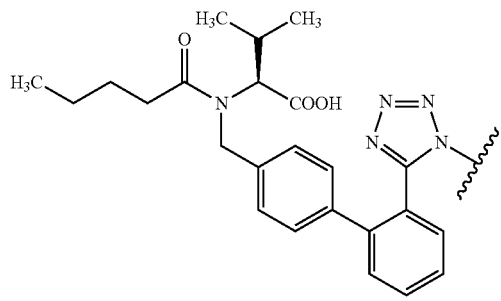 [SMILES: *n1nnnc1-c1ccccc1-c1ccc(CN(C(=O)CCCC)[C@H](C(=O)O)C(C)C)cc1]
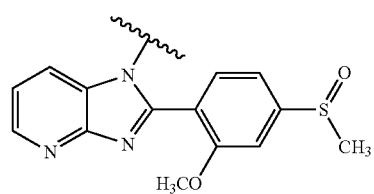 [SMILES: *n1c(-c2ccc(S(C)=O)cc2OC)nc2ncccc21]
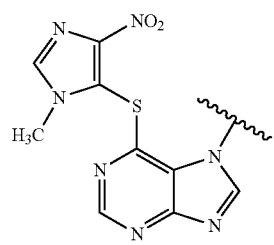 [SMILES: *n1cnc2ncnc(Sc3c([N+](=O)[O-])ncn3C)c21]
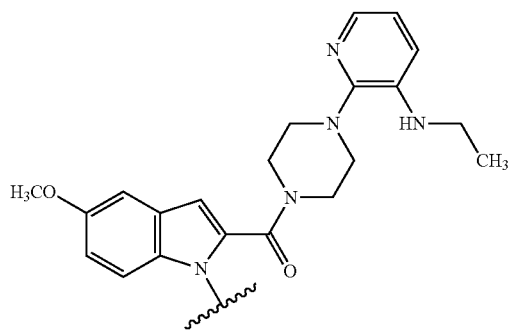 [SMILES: *n1c(C(=O)N2CCN(c3ncccc3NCC)CC2)cc2cc(OC)ccc21]
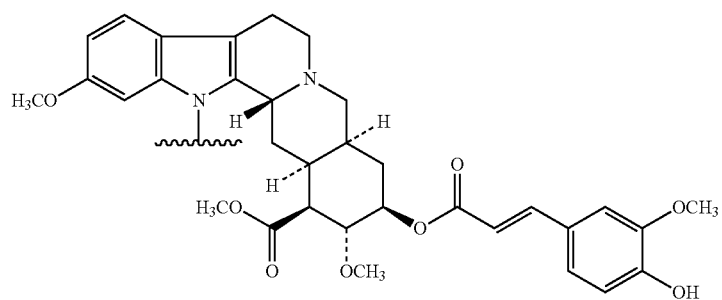 [SMILES: *n1c2c(c3ccc(OC)cc31)CCN1C[C@H]3C[C@@H](OC(=O)/C=C/c4ccc(O)c(OC)c4)[C@H](OC)[C@@H](C(=O)OC)[C@H]3C[C@H]21]

TABLE 13-continued

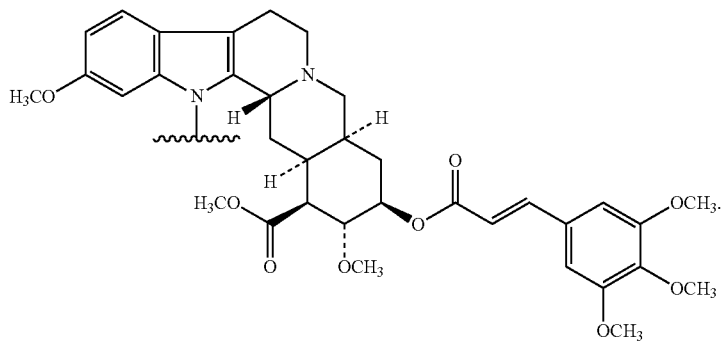 [SMILES: *n1c2c(c3ccc(OC)cc31)CCN1C[C@H]3C[C@@H](OC(=O)/C=C/c4cc(OC)c(OC)c(OC)c4)[C@H](OC)[C@@H](C(=O)OC)[C@H]3C[C@H]21]

In another aspect of the invention a general method to synthesize prodrugs that can be linked to multiple drug molecules is provided (Scheme 1).

In another aspect of the invention a general method to synthesize prodrugs that can be linked to two parent drug molecules through alkyl group is provided (Scheme 2). The

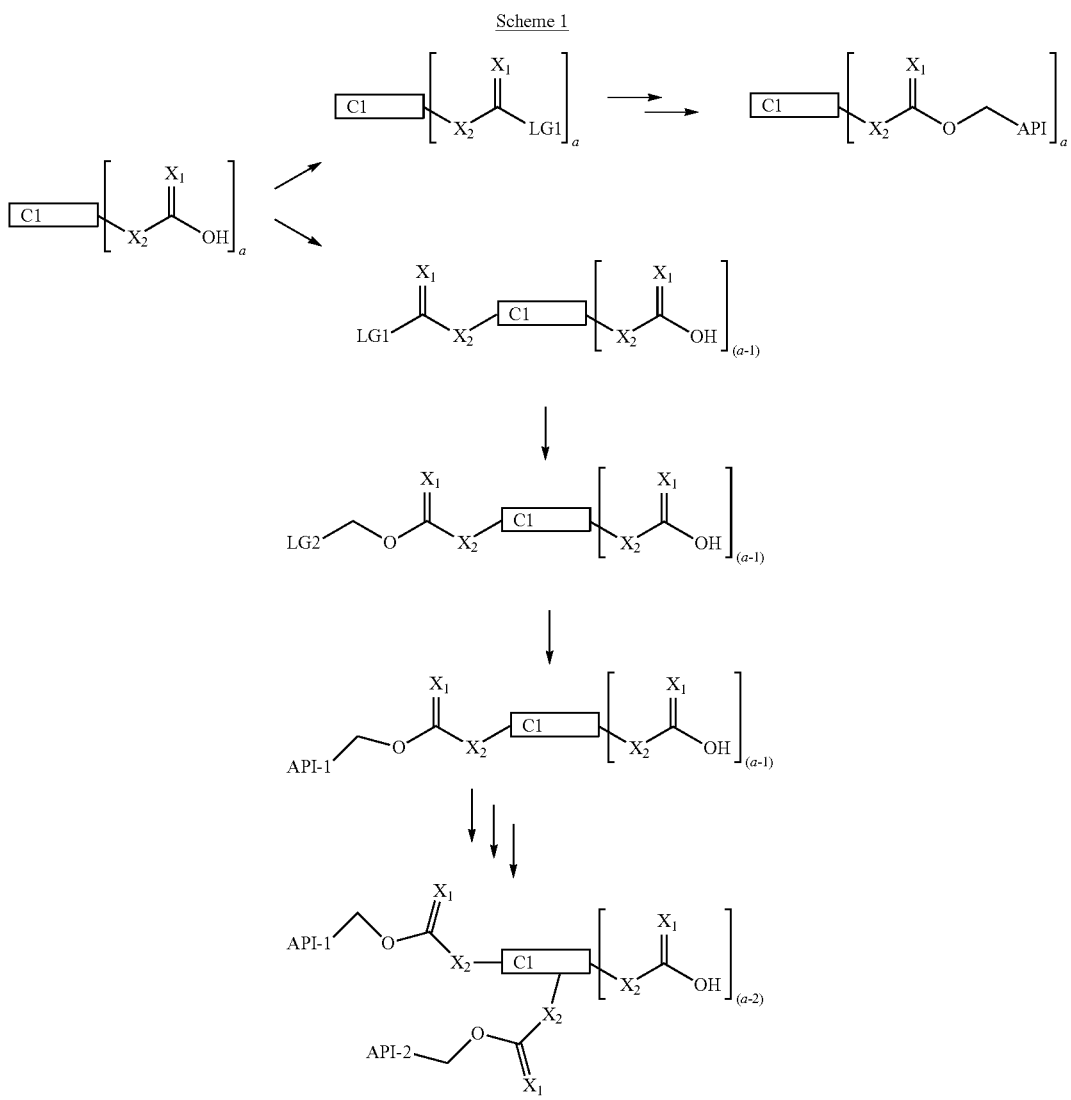

wherein each LG-1 and LG-2 is independently a leaving group, preferably a chloride, bromide or iodide.

same methodology can be used to synthesize prodrugs with branched and substituted alkyl groups.

Scheme 2

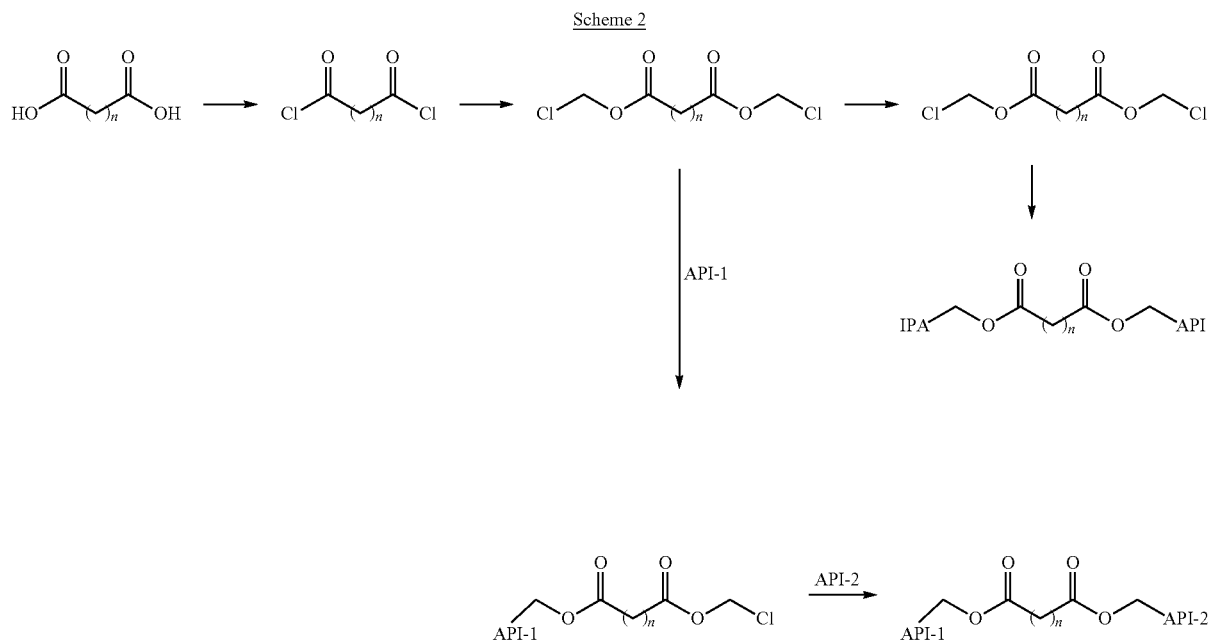

wherein n is an integer between about 1 and about 50, preferably between about 4 and about 26.

In one embodiment, the dicarboxylic acid from Scheme 2 is selected from oxalic acid, malonic acid, succinic acid, glutaric acid, adipic acid, pimelic acid, suberic acid, azelaic acid, sebacic acid, undecanedioic acid, dodecanedioic acid, ortho-, para- or meta-phthalic acid, maleic acid, fumaric acid, glutaconic acid, traumatic acid or muconic acid. In one embodiment, the dicarboxylic acid is reacted with one mole equivalent or less of thionyl chloride to give a mixture of mono and disubstituted acid chloride. In another embodiment, the dicarobxylic acid is reacted with two or more mole equivalents of thionyl chloride. The acid chlorides can be converted to chloromethyl esters by reacting with trioxane or paraformaldehyde using zirconium tetrachloride as the Lewis acid. (Mudryk, B. et. al., *Tetrahedron Letters* 43(36), 2002, 6317-6318). The chloromethyl esters can be reacted with reactive APIs, such as amine containing pharmacophores to give the final conjugates. Methods for attaching biologically active agents containing amine groups through labile groups are disclosed in U.S. application Ser. No. 12/823,102. The methods described therein can be adapted to convert dicarboxylic acid containing carrier groups herein.

In another aspect of the invention a general method to synthesize prodrugs of aripiprazole that can be linked to two aripiprazole molecules through alkyl group is provided (Scheme 3). The invention further provides a prodrug of aripiprazole selected from Table 14.

Scheme 3

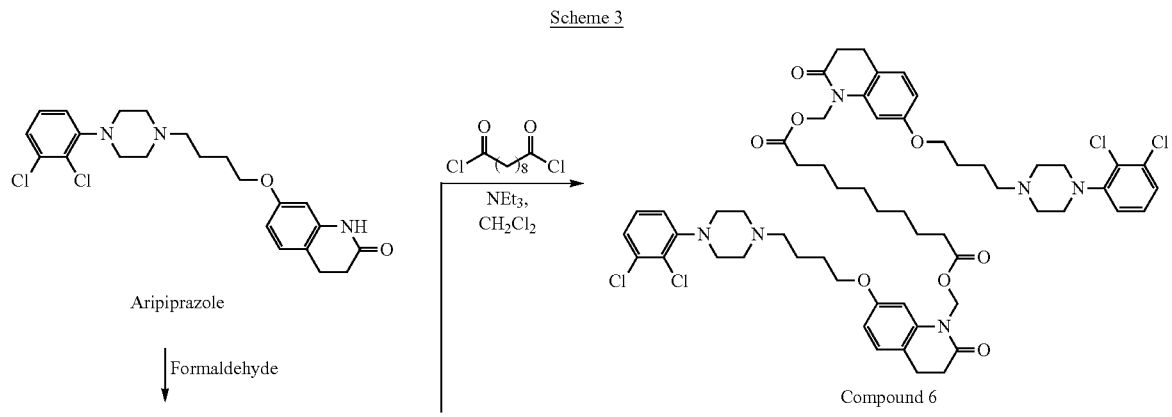

-continued
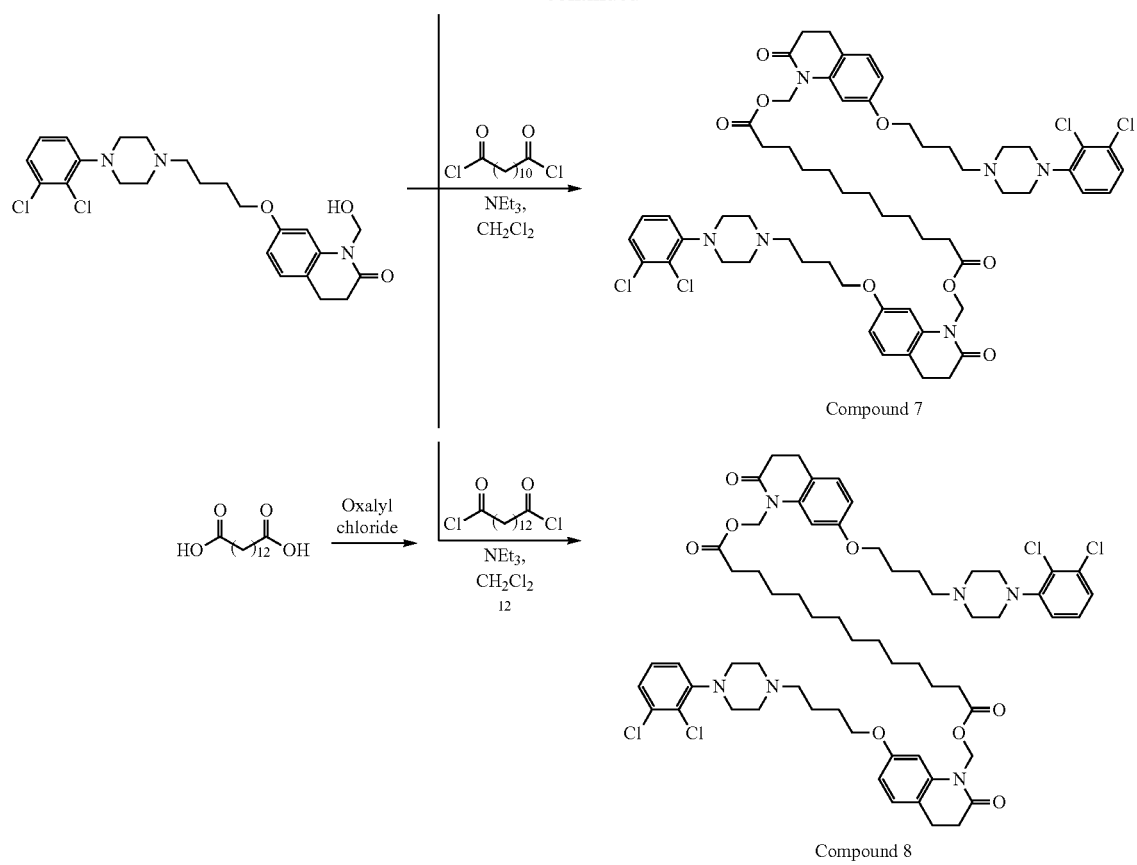
Compound 7
Compound 8
TABLE A
| Compound No. | Structure |
|---|---|
| 1 | 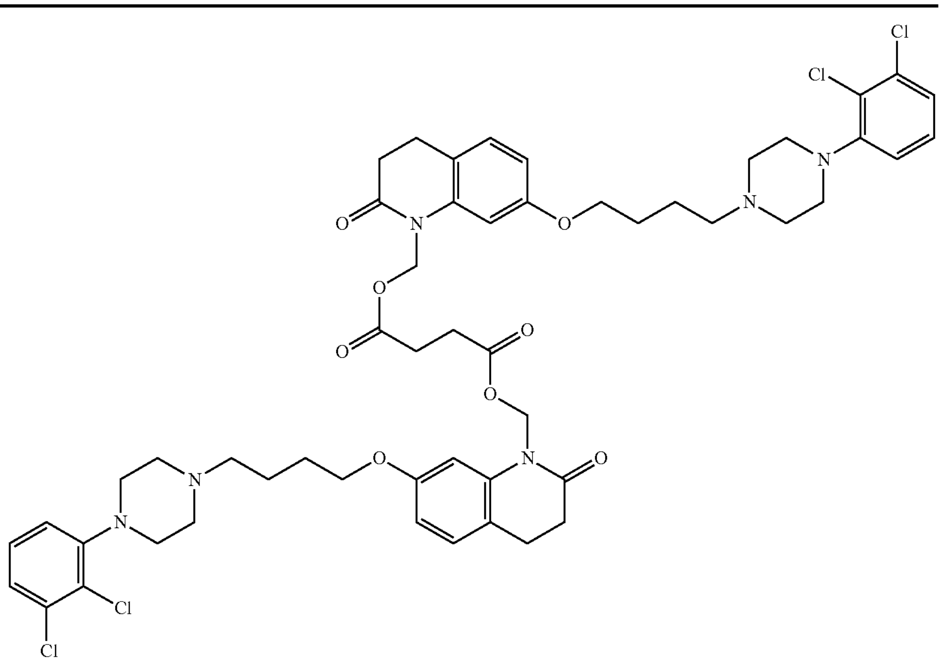 |

TABLE A-continued
| Compound No. | Structure |
|---|---|
| 2 | 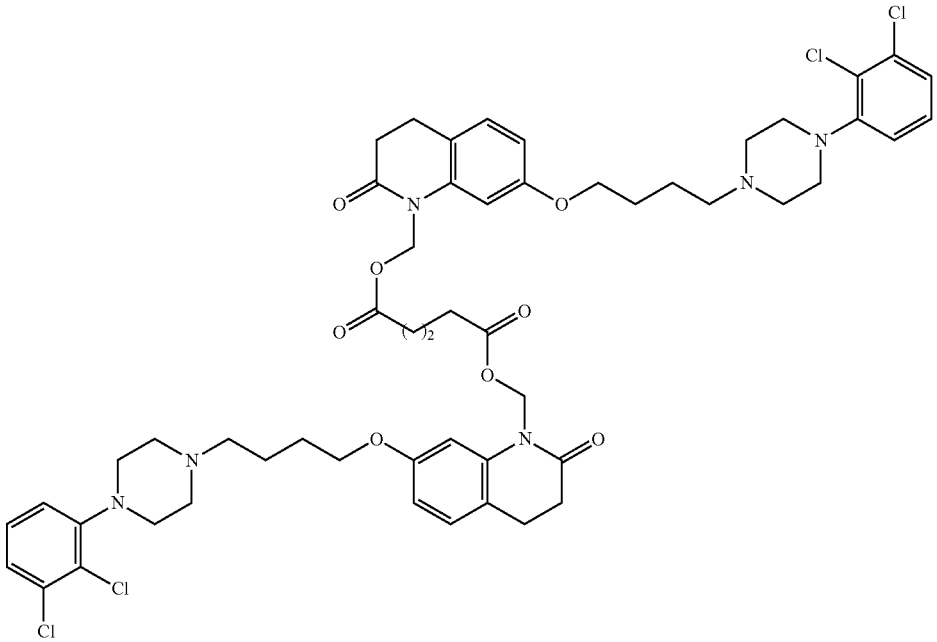 |
| 3 | 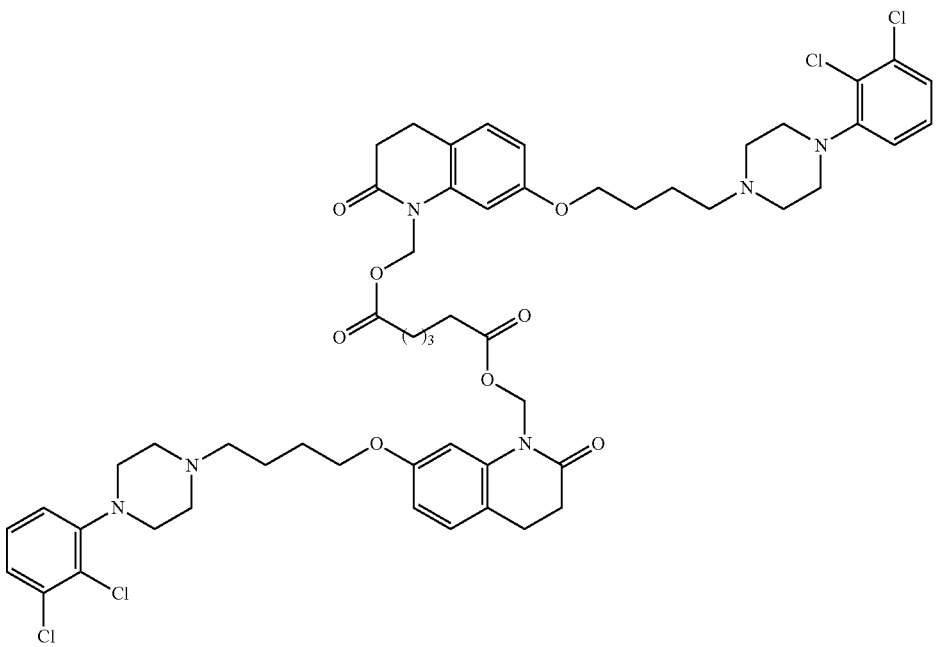 |

TABLE A-continued
| Compound No. | Structure |
|---|---|
| 4 | 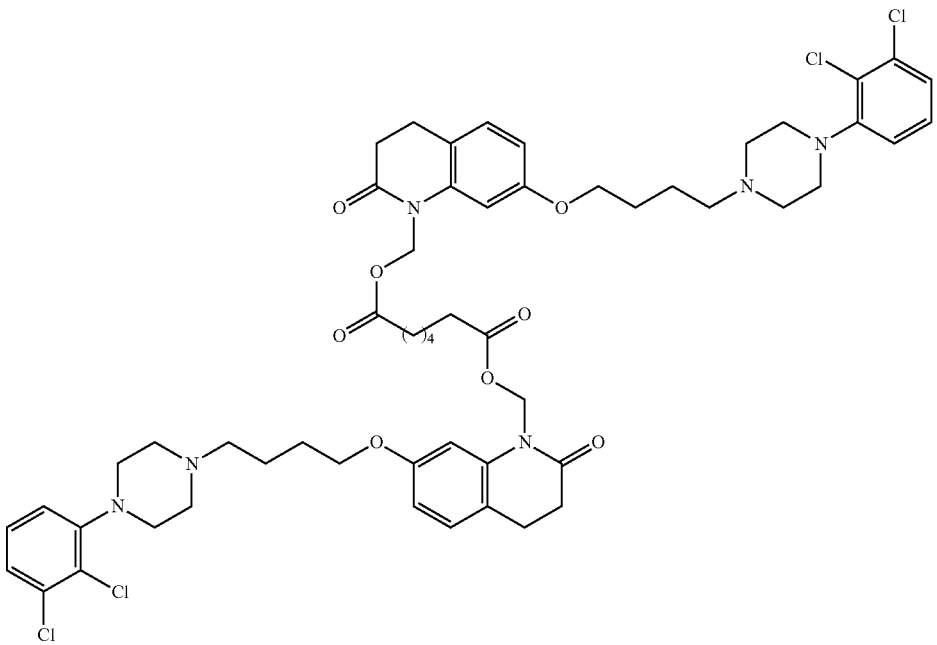 |
| 5 | 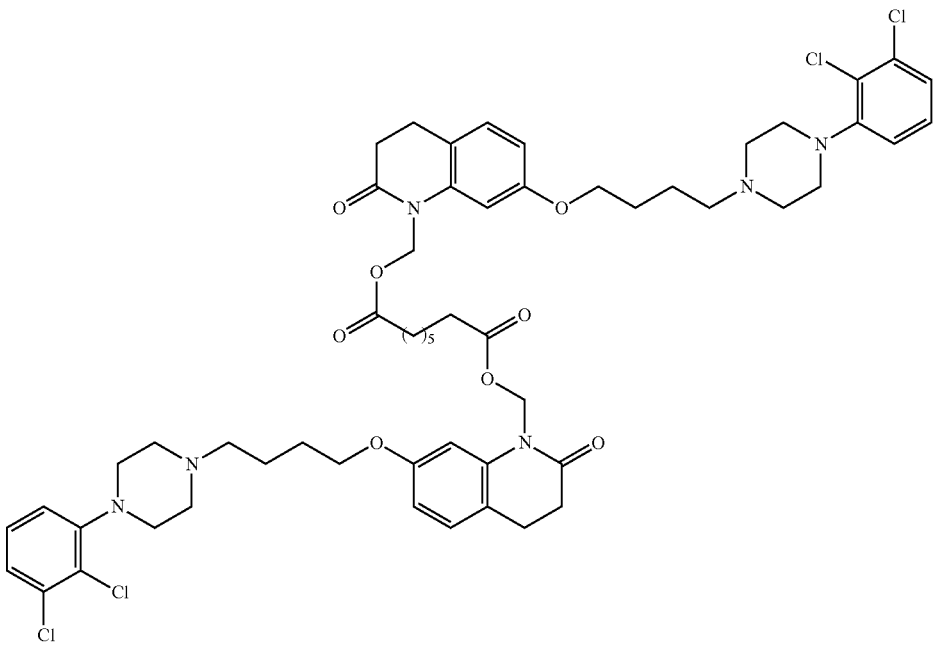 |

TABLE A-continued
| Compound No. | Structure |
|---|---|
| 6 | 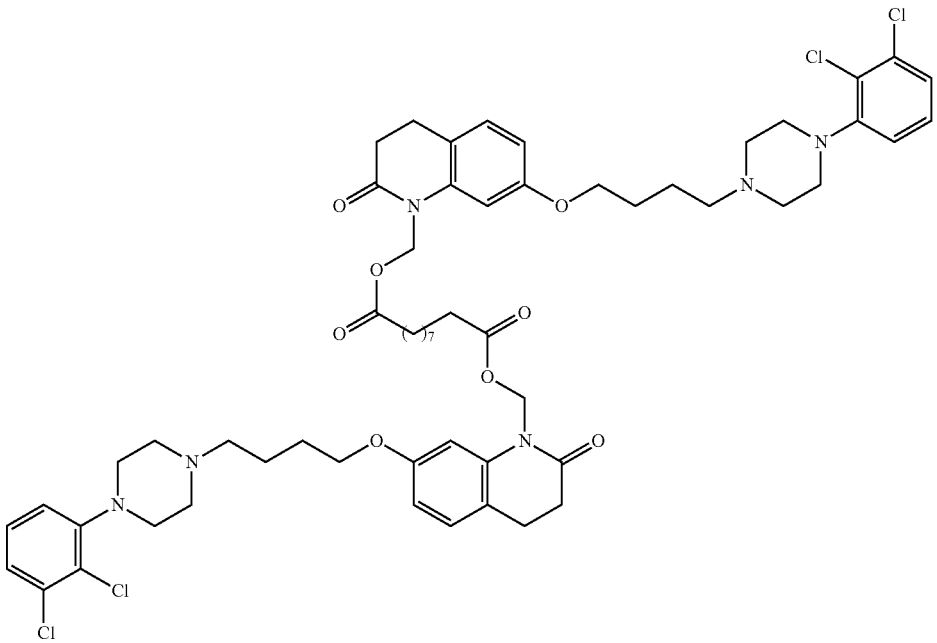 |
| 7 | 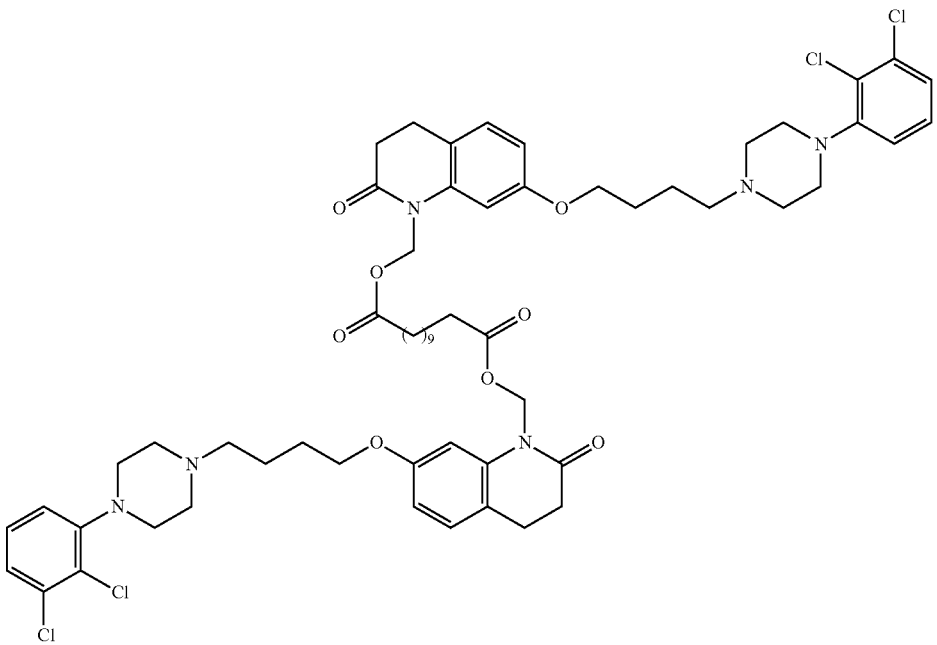 |

TABLE A-continued
| Compound No. | Structure |
|---|---|
| 8 | 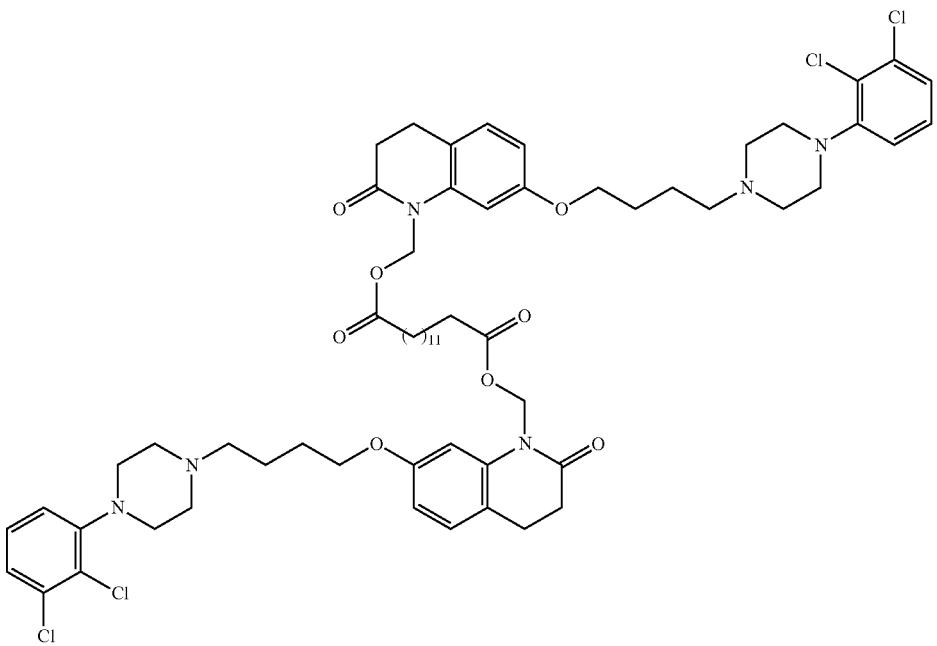 |
| 9 | 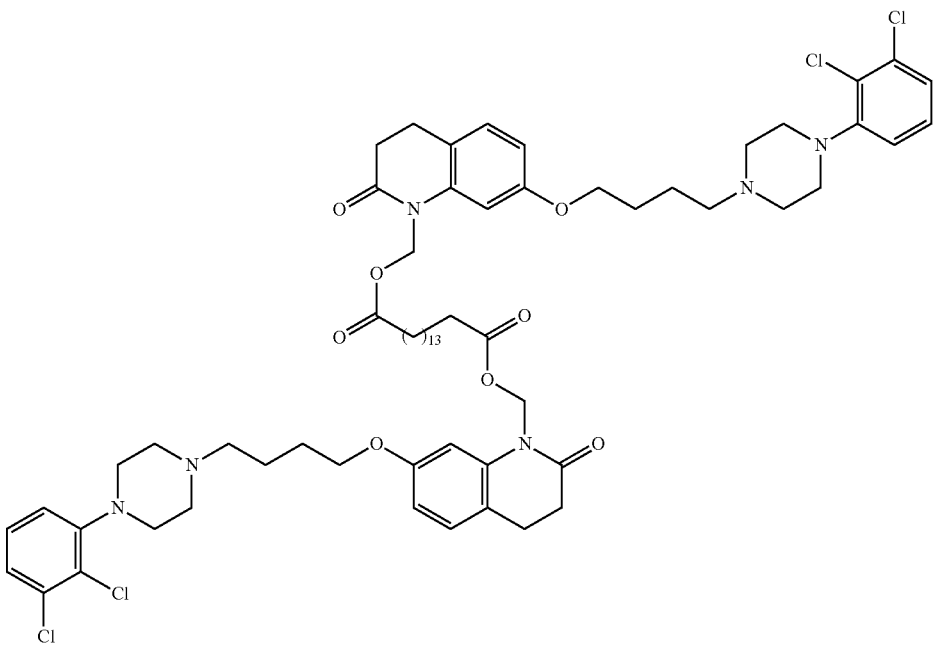 |

US 10,584,099 B2
121
122
TABLE A-continued
| Compound No. | Structure |
|---|---|
| 10 | 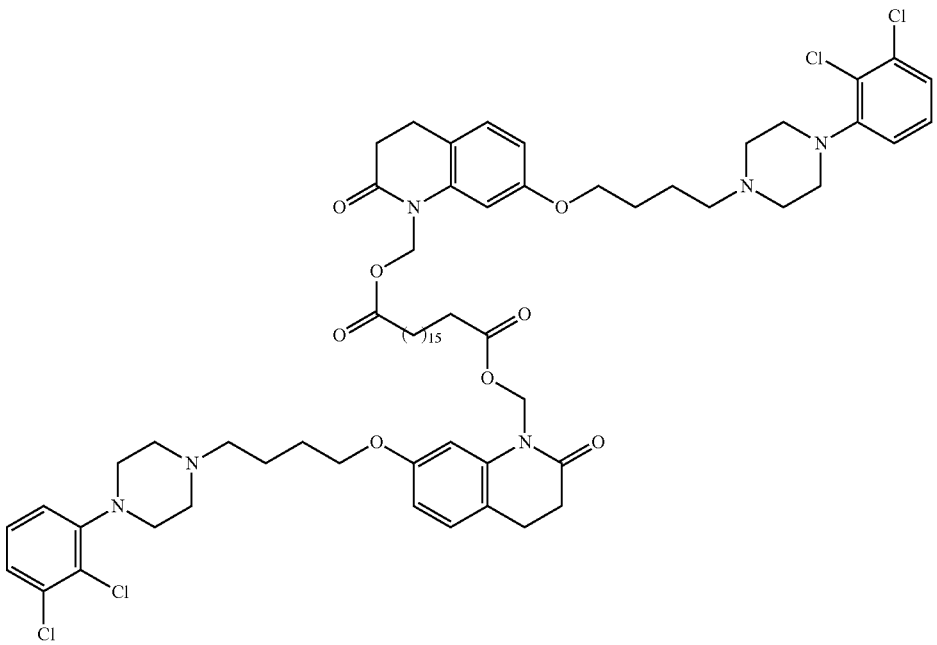 |
| 11 | 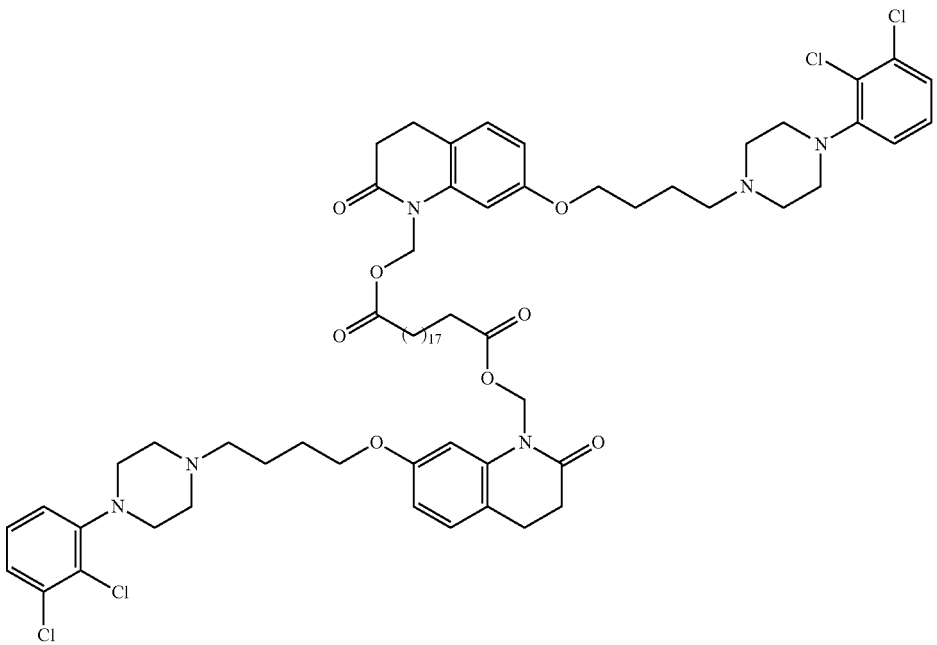 |

TABLE A-continued

| Compound No. | Structure |
|---|---|
| 12 | 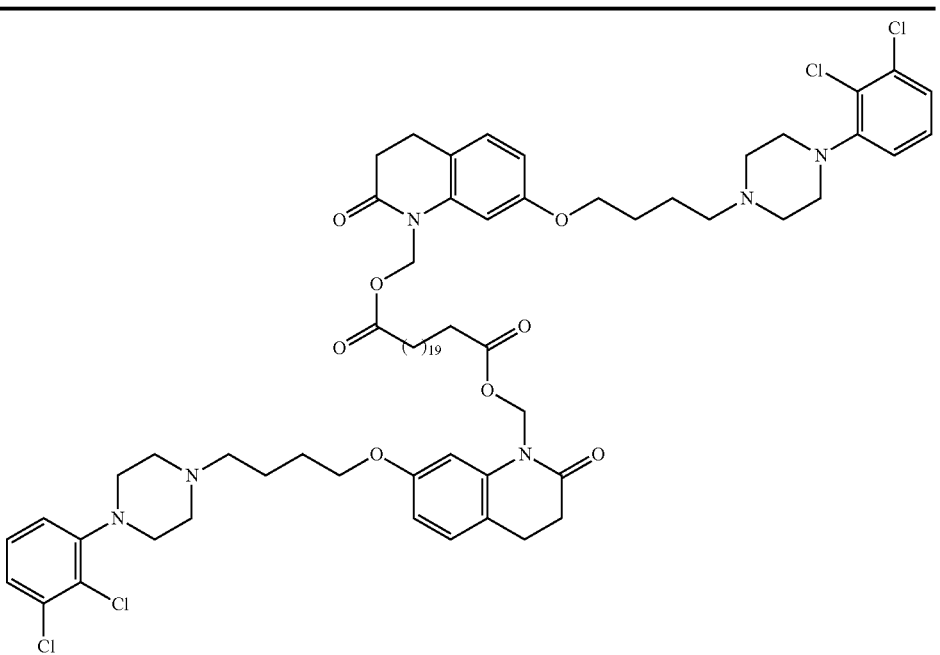 |

In one embodiment, the compounds of Formula I, IA or IB are less soluble, and are preferably at least an order of magnitude less soluble, as compared to the parent drug from which they were derived. In one embodiment, the prodrugs of Formula I, IA or IB have an aqueous solubility of less than about 0.5 mg/ml, preferably less than about 0.1 mg/mL, preferably less than about 0.01 mg/mL, preferably less than about 0.001 mg/mL, preferably less than about 0.0001 mg/mL and even more preferably less than about 0.00001 mg/ml when solubility is measured in a phosphate buffer (pH 7.4) at room temperature.

In a preferred embodiment, a compound of the invention provides sustained delivery of the parent drug over hours, days, weeks or months when administered, for example, orally or parenterally, to a subject. For example, the compounds can provide sustained delivery of the parent drug for at least 8, 12, 24, 36 or 48 hours or at least 4, 7, 15, 30, 60, 75 or 90 days or longer. Without being bound by a theory, it is believed that the compounds of the invention form an insoluble depot upon parenteral administration, for example subcutaneous, intramuscular or intraperitoneal injection. In one embodiment a prodrug of the invention may further comprise a sustained release delivery system for providing additional protection of the prodrug from enzymatic or chemical degradation.

In another embodiment, the invention provides a method for sustained delivery of a parent lactam, amide, imide, sulfonamide, carbamate, urea, benzamide, or acylaniline containing drug to a subject in need thereof. Each of these groups comprises an amidic N—H group. The method comprises administering to the subject an effective amount of a prodrug formed by substituting on the NH group a labile, hydrophobic aldehyde-linked prodrug moiety wherein the prodrug has reduced solubility under physiological conditions compared to the parent drug and provides for longer sustained therapeutic levels of the parent drug following administration than observed levels following administration of the parent drug. In a preferred embodiment, the amidic N—H group has a pKa of about 5 to about 22, preferably about 5 to about 21, and preferably about 5 to about 20.

Prodrugs of Secondary Amine Drugs

The invention further relates to prodrugs of secondary amine containing drugs of Formula LI:

Formula LI

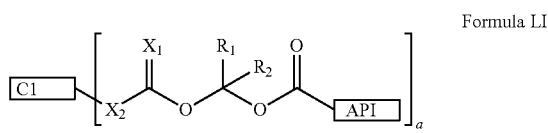

In some embodiments, the invention relates to a prodrug conjugate having the formula:

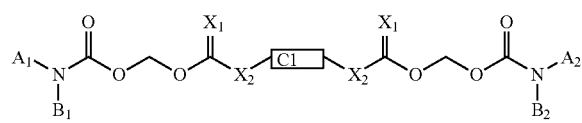

wherein $A_1$ and $B_1$ together with the nitrogen they are attached to form a first biologically active molecule; and, $A_2$ and $B_2$ together with the nitrogen they are attached to form a second biologically active molecule.

In some embodiments, the invention relates to a prodrug of a secondary amine containing parent drug having the Formula LI-A:

Formula LI-A

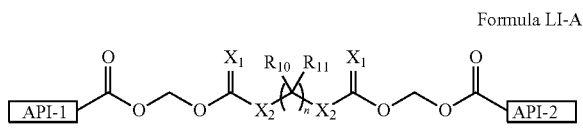

wherein n is an integer between about 1 and about 50;
$X_1$ is S or O;
$X_2$ is selected from direct bond, O, S or $NR_{20}$;
each $R_{10}$ and $R_{11}$ is independently selected from absent, hydrogen, halogen, —$OR_{20}$, —$SR_{20}$, —$NR_{20}R_{21}$, —C(O)$R_{20}$, —C(O)$OR_{20}$, —C(O)$NR_{20}R_{21}$, —N($R_{20}$)C(O)$R_{21}$, —$CF_3$, —CN, —$NO_2$, —$N_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl; wherein each $R_{20}$ and $R_{21}$ is selected from hydrogen, halogen, aliphatic, substituted aliphatic, aryl or substituted aryl;
alternatively two $R_{10}$ and $R_{11}$ together with the atoms to which they are attached may form an optionally substituted 3, 4, 5, 6 or 7 membered carbocyclic or heterocyclyl ring.

In a preferred embodiment, n is selected from 4, 5, 6, 7, 8, 9, 10, 11, 12, 13, 14, 15, 16, 17, 18, 19, 20, 21, 22, 23, 24, 25, 26, 27, 28, 29 and 30.

The secondary amine-containing parent drugs (designated in Formula LI as API-1 and API-2) can be any secondary amine-containing parent drug that induces a desired local or systemic effect. Such parent drugs include broad classes of compounds. Several examples include: respiratory drugs, including antiasthmatic agents; analgesic agents; antidepressants; antianginal agents; antiarrhythmic agents; antihypertensive agents; antidiabetic agents; antihistamines; anti-infective agents such as antibiotics; antiinflammatory agents; antiparkinsonism drugs; antipsychotics; antipyretic agents; antiulcer agents; attention deficit hyperactivity disorder (ADHD) drugs; central nervous system stimulants; cough and cold preparations, including decongestants; and psychostimulants.

Examples of secondary-amine containing parent drugs from which prodrugs of the invention may be derived include: alprenolol, acebutolol, amidephrine, amineptine, amosulalol, amoxapine, amphetaminil, atenolol, atomoxetine, balofloxacin, bamethan, befunolol, benazepril, benfluorex, benzoctamine, betahistine, betaxolol, bevantolol, bifemelane, bisoprolol, brinzolamide, bufeniode, butethamine, camylofine, carazolol, carticaine, carvedilol, cephaeline, ciprofloxacin, clozapine, clobenzorex, clorprenaline, cyclopentamine, delapril, demexiptiline, denopamine, desipramine, desloratadine (clarinex), diclofenac, dimetofrine, dioxadrol, dobutamine, dopexamine, doripenem, dorzolamide, droprenilamine, duloxetine, eltoprazine, enalapril, enoxacin, epinephrine, ertapenem, esaprazole, esmolol, etoxadrol, fasudil, fendiline, fenethylline, fenfluramine, fenoldopam, fenoterol, fenproporex, flecainide, fluoxetine, formoterol, frovatriptan, gaboxadol, garenoxacin, gatifloxacin, grepafloxacin, hexoprenaline, imidapril, indalpine, indecainide, indeloxazine hydrochloride, isoxsuprine, ispronicline, labetalol, landiolol, lapatinib, levophacetoperane, lisinopril, lomefloxacin, lotrafiban, maprotiline, mecamylamine, mefloquine, mepindolol, meropenem, metapramine, metaproterenol, methoxyphenamine, dtmp (dextrorotary methylphenidate), methylphenidate, metipranolol, metoprolol, mitoxantrone, mivazerol, moexipril, moprolol, moxifloxacin, nebivolol, nifenalol, nipradilol, norfloxacin, nortriptyline, nylidrin, olanzapine, oxamniquine, oxprenolol, oxyfedrine, paroxetine, perhexiline, phenmetrazine, phenylephrine, phenylpropylmethylamine, pholedrine, picilorex, pimefylline, pindolol, pipemidic acid, piridocaine, practolol, pradofloxacin, pramipexole, pramiverin, prenalterol, prenylamine, prilocaine, procaterol, pronethalol, propafenone, propranolol, propylhexedrine, protokylol, protriptyline, pseudoephedrine, reboxetine, rasagiline, (r)-rasagiline, repinotan, reproterol, rimiterol, ritodrine, safinamide, salbutamol/albuterol, salmeterol, sarizotan, sertraline, silodosin, sotalol, soterenol, sparfloxacin, spirapril, sulfinalol, synephrine, tamsulosin, tebanicline, tianeptine, tirofiban, tretoquinol, trimetazidine, troxipide, varenicline (champix), vildagliptin, viloxazine, viquidil and xamoterol.

Preferred secondary amine-containing parent drugs from which prodrugs of the invention are derived include atenolol, atomoxetine, clozapine, desipramine, desloratadine (clarinex), diclofenac, doripenem, duloxetine, enalapril, ertapenem, fluoxetine, metoprolol, mecamylamine, meropenem, methylphenidate, dtmp (dextrorotary methylphenidate), olanzapine, paroxetine, pramipexole, rasagiline, ®-RASAGILINE, salbutamol/albuterol, tamsulosin, varenicline (hantix), and vildagliptin. In a more preferred embodiment, the secondary amine-containing parent drug is selected from clozapine, duloxetine, mecamylamine, pramipexole, rasagiline, ®-RASAGILINE, and olanzapine.

In one embodiment, the parent drug moieties (APIs) are selected from Table 14. In one embodiment, the prodrug is a compound of Formula LI or LI-A wherein API-1 and API-2 are selected from Table 14. In one embodiment both API-1 and API-2 represent the same parent drug.

TABLE 14

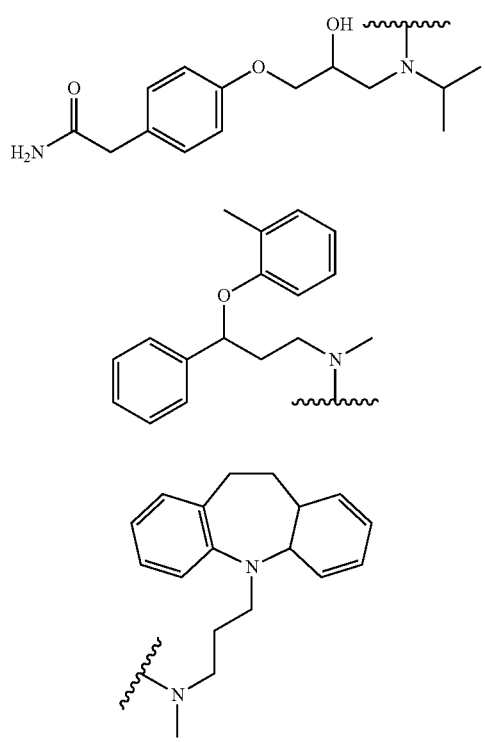

TABLE 14-continued
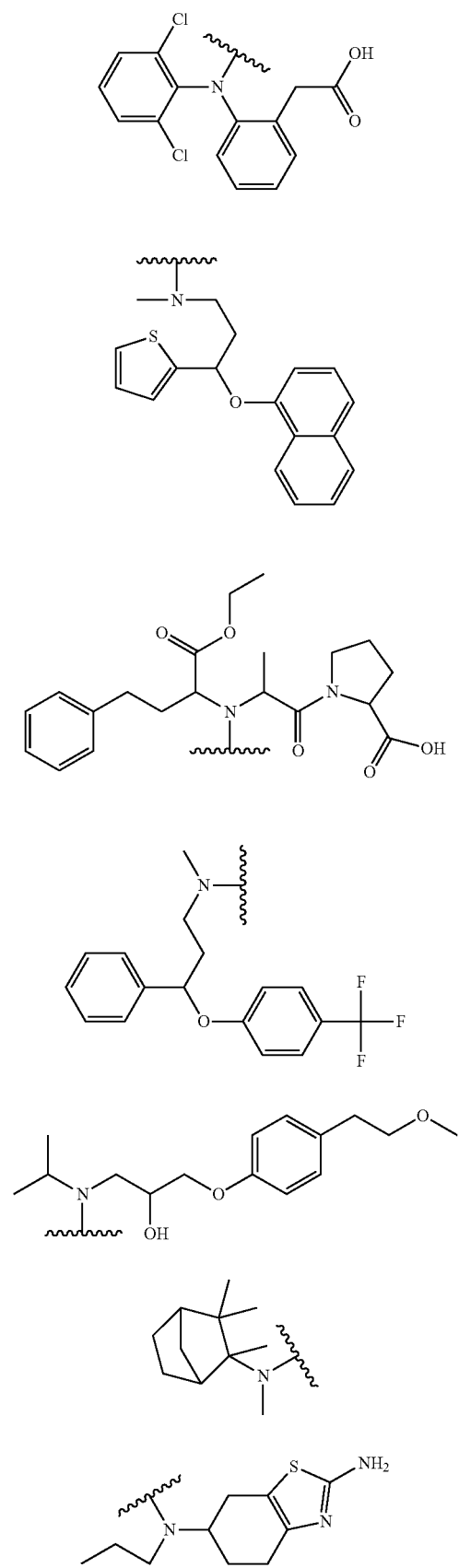
TABLE 14-continued
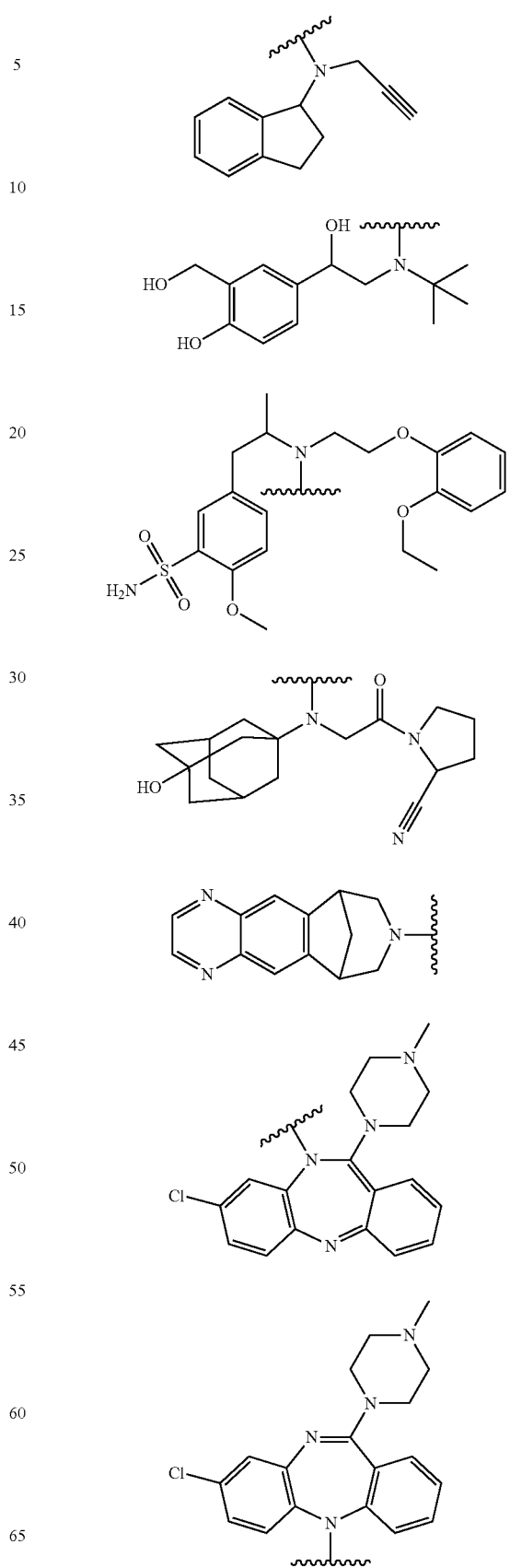

TABLE 14-continued
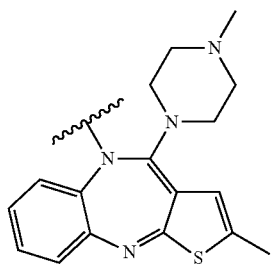 [SMILES: *N1C(N2CCN(C)CC2)=c2cc(C)sc2=Nc2ccccc21]
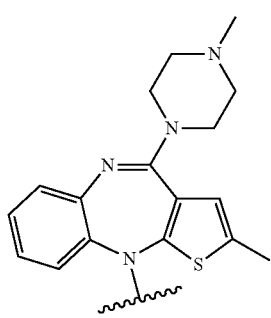 [SMILES: *N1c2ccccc2N=C(N2CCN(C)CC2)c2cc(C)sc21]
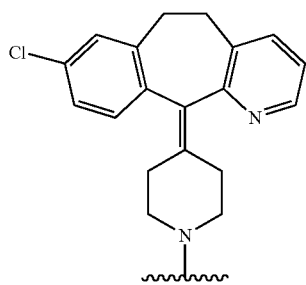 [SMILES: *N1CCC(=C2c3ccc(Cl)cc3CCc3cccnc32)CC1]
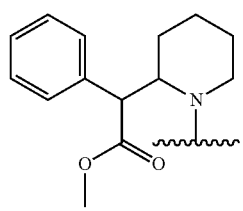 [SMILES: *N1CCCCC1C(C(=O)OC)c1ccccc1]
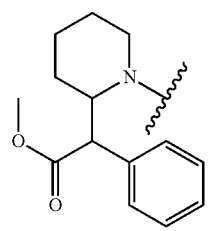 [SMILES: *N1CCCCC1C(C(=O)OC)c1ccccc1]
TABLE 14-continued
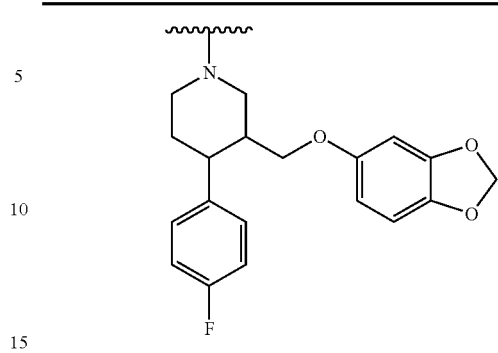
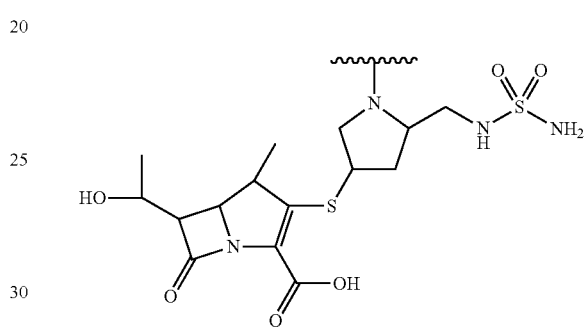
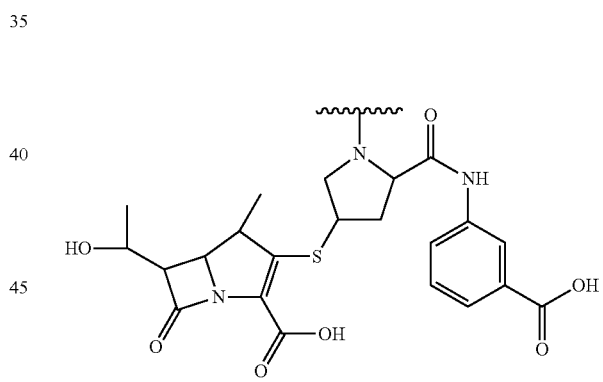
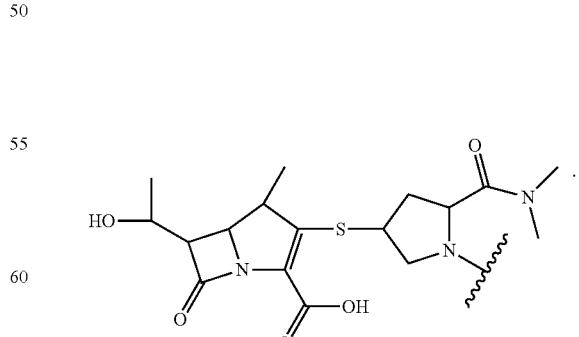
In a more preferred embodiment, the invention relates to a prodrug of olanzapine represented by formula:

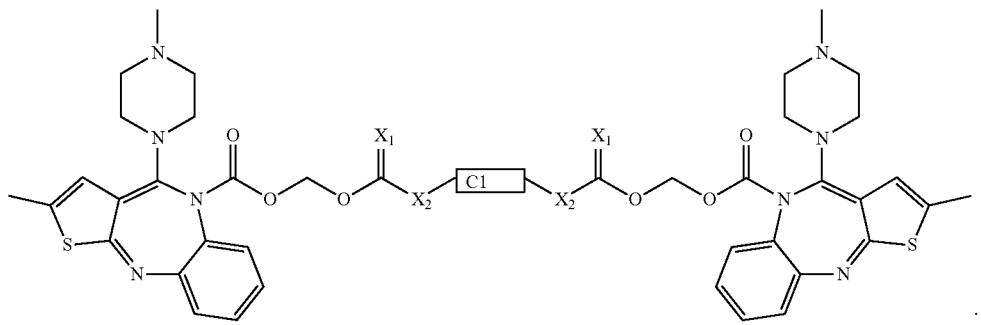
In a more preferred embodiment, the invention relates to a prodrug of olanzapine represented by formula:
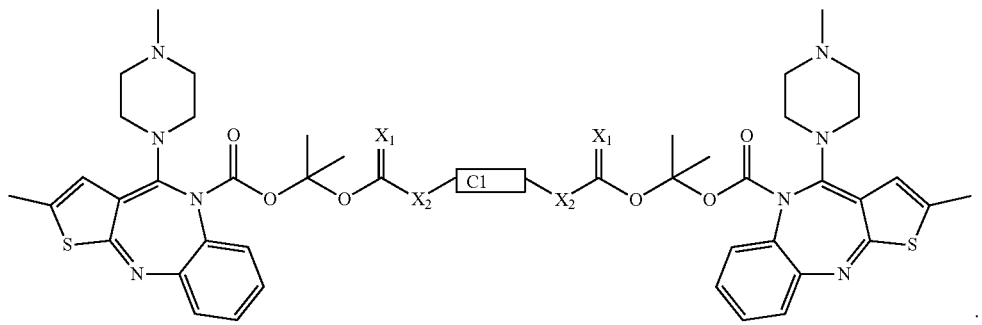
In a preferred embodiment, the invention relates to a prodrug of olanzapine represented by formula:
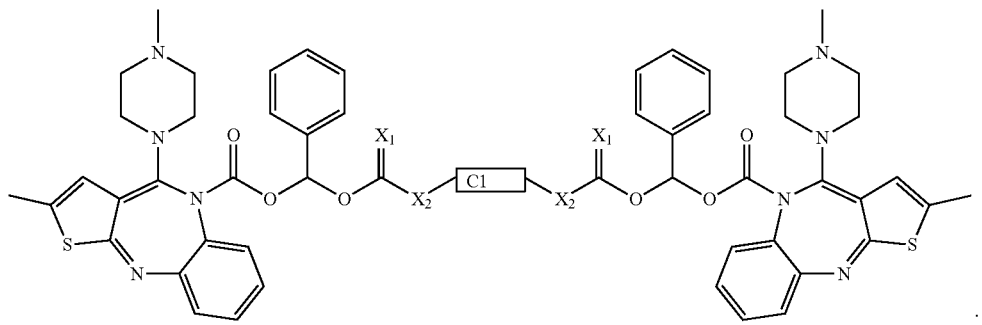
In a more preferred embodiment, the invention relates to a prodrug of olanzapine represented by formula:
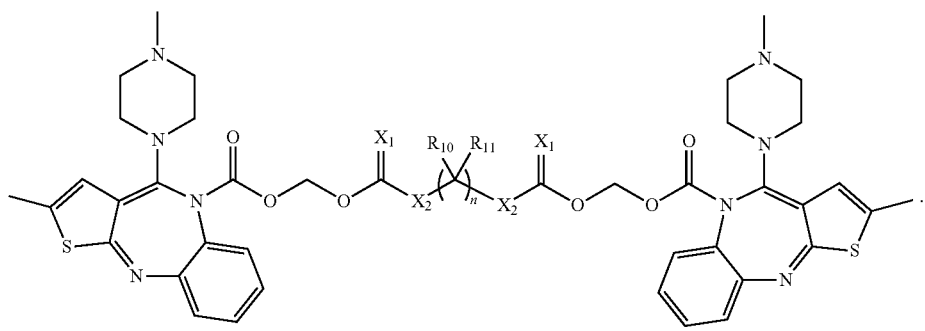

In a more preferred embodiment, the invention relates to a prodrug of olanzapine represented by formula:

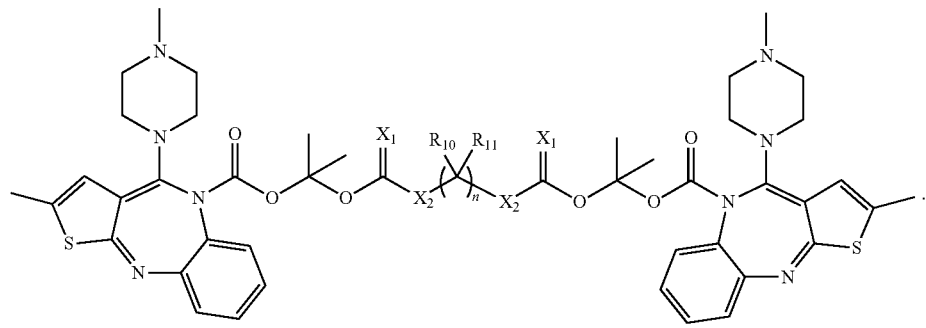

In a more preferred embodiment, the invention relates to a prodrug of olanzapine represented by formula:

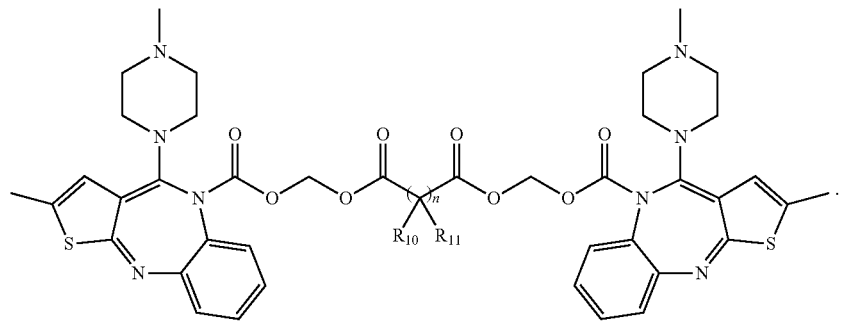

In a more preferred embodiment, the invention relates to a prodrug of olanzapine represented by formula:

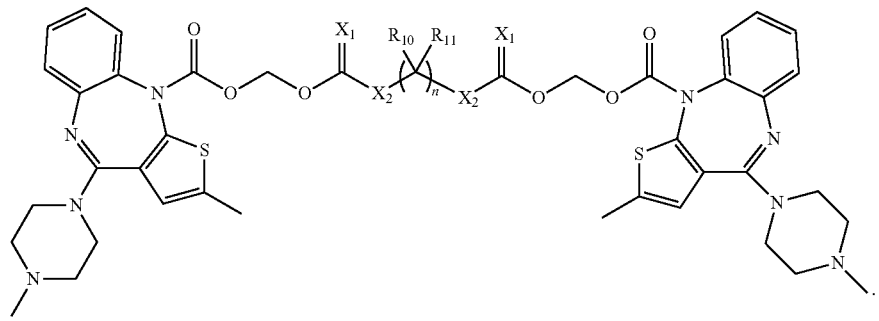

In a more preferred embodiment, the invention relates to a prodrug of olanzapine represented by formula:

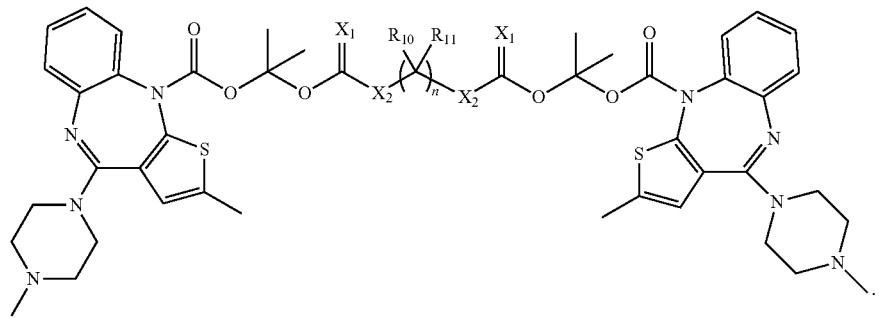

In a more preferred embodiment, the invention relates to a prodrug of olanzapine represented by formula:

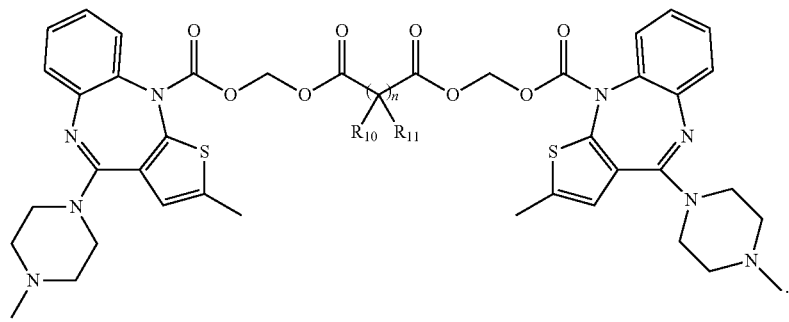

In a preferred embodiment, the invention relates to a prodrug of olanzapine represented by formula:

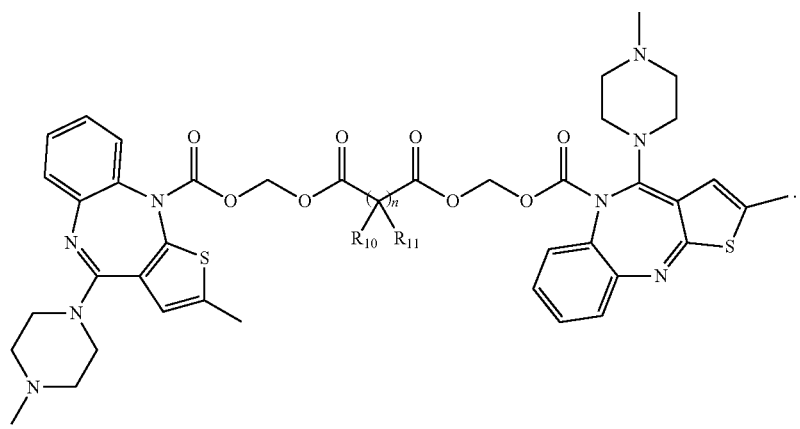

Synthesis of Compounds

Generally, the compounds of the invention can be synthesized by the method set forth in Schemes 3A and 3B where derivatization of olanzapine is illustrated.

Scheme 3A

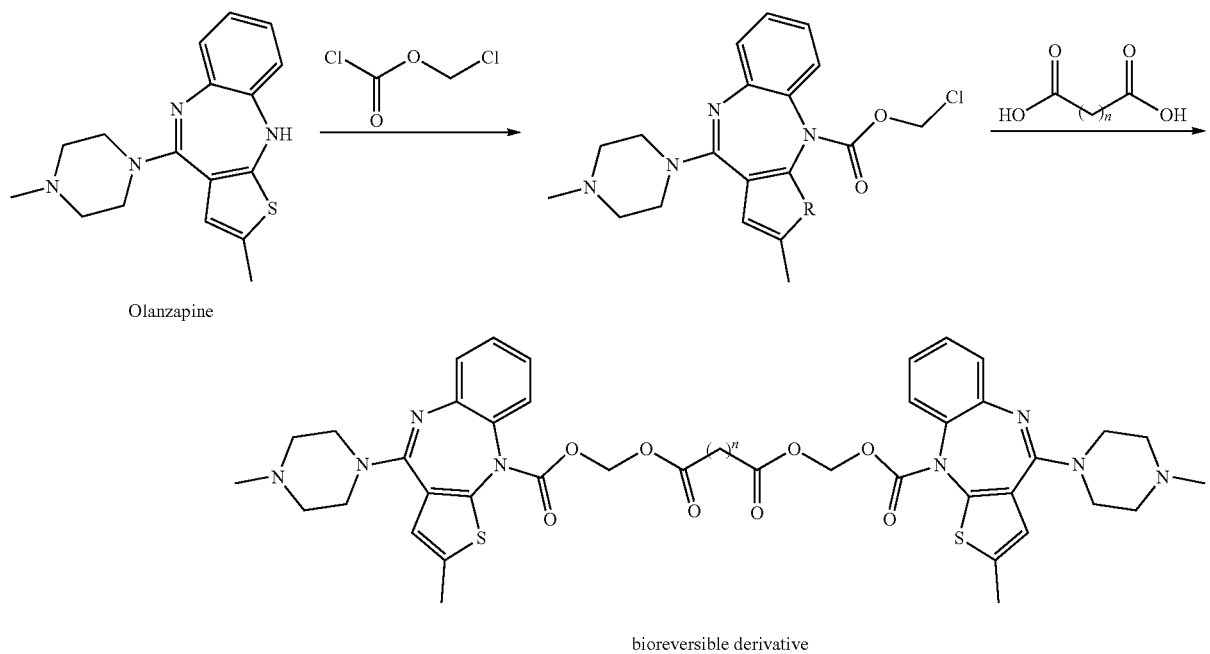

bioreversible derivative

Scheme 3B

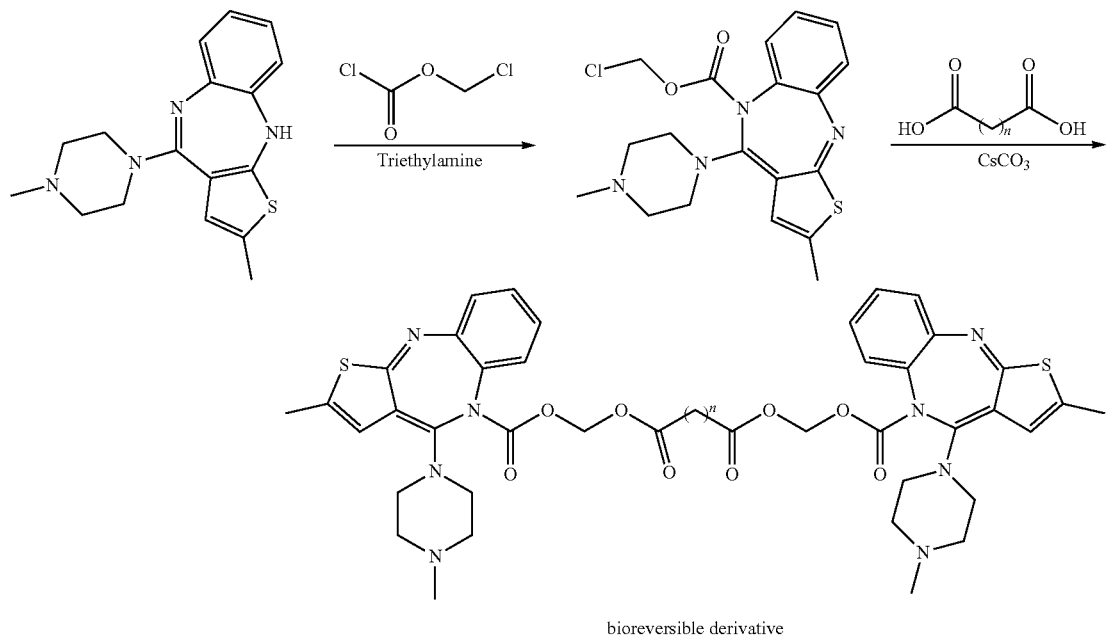

bioreversible derivative

Schemes 3A and 3B illustrate the synthesis of a compound of Formula LI by condensation of the parent drug, olanzapine, with chloromethyl chloroformate, followed by condensation with a carboxylic acid.

Definitions

Listed below are definitions of various terms used to describe this invention. These definitions apply to the terms as they are used throughout this specification and claims, unless otherwise limited in specific instances, either individually or as part of a larger group.

The terms "API", "biologically active moiety", "drug moiety" and "parent drug moiety" are used interchangeably to refer to the structure of a parent drug molecule which is present in a prodrug conjugate of the invention. As will be understood by one of skill in the art, in certain embodiments, linking the drug molecule to a carrier moiety proceeds via substitution at an oxygen or nitrogen atom of the parent drug molecule with loss of a hydrogen atom. In these embodiments, the parent drug moiety is the radical resulting from removal of the O—H or N—H hydrogen atom from the parent drug molecule. In certain embodiments, the carrier moiety is linked to the parent drug molecule without any loss of atoms from the parent drug molecule. In these embodiments, the parent drug moiety includes the entire structure of the parent drug compound. For example, in case of a tertiary amine parent drug that is converted to a quaternary prodrug conjugate a loss of hydrogen from the parent drug doesn't occur.

The term "aliphatic group" or "aliphatic" refers to a non-aromatic moiety that may be saturated (e.g., single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g., pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g., morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g., 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g., benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

The term "labile" as used herein refers to the capacity of the prodrug of the invention to undergo enzymatic and/or chemical cleavage in vivo thereby forming the parent drug. As used herein the term "prodrug" means a compounds as disclosed herein which is a labile derivative compound of a parent drug which when administered to a patient in vivo becomes cleaved by chemical and/or enzymatic hydrolysis thereby forming the parent drug such that a sufficient amount of the compound intended to be delivered to the patient is available for its intended therapeutic use in a sustained release manner.

The term "dendrimer" refers to a class of highly branched, often spherical, macromolecular polymers that exhibit greater monodispersity (i.e., a smaller range of molecular weights, sizes, and shapes) than linear polymers of similar size. These three-dimensional oligomeric structures are prepared by reiterative reaction sequences starting from a core molecule (such as diaminobutane or ethylenediamine) that has multiple reactive groups. When monomer units, also having multiple reactive groups, are reacted with the core, the number of reactive groups comprising the outer bounds of the dendrimer increases. Successive layers of monomer molecules may be added to the surface of the dendrimer, with the number of branches and reactive groups on the surface increasing geometrically each time a layer is added. The number of layers of monomer molecules in a dendrimer may be referred to as the "generation" of the dendrimer. The total number of reactive functional groups on a dendrimer's outer surface ultimately depends on the number of reactive groups possessed by the core, the number of reactive groups possessed by the monomers that are used to grow the dendrimer, and the generation of the dendrimer.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Additional sustained release in accordance with the invention may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

In one preferred embodiment, the formulation provides a sustained release delivery system that is capable of minimizing the exposure of the prodrug to water. This can be accomplished by formulating the prodrug with a sustained release delivery system that is a polymeric matrix capable of minimizing the diffusion of water into the matrix. Suitable polymers comprising the matrix include polylactide (PLA) polymers and the lactide/glycolide (PLGA) co-polymers.

Alternatively, the sustained release delivery system may comprise poly-anionic molecules or resins that are suitable for injection or oral delivery. Suitable polyanionic molecules include cyclodextrins and polysulfonates formulated to form a poorly soluble mass that minimizes exposure of the prodrug to water and from which the prodrug slowly leaves.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a prodrug compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect).

In accordance with the invention, the therapeutically effective amount of a prodrug of the invention is typically based on the target therapeutic amount of the parent drug. Information regarding dosing and frequency of dosing is readily available for many parent drugs from which the prodrugs of the invention are derived and the target therapeutic amount can be calculated for each prodrug of the invention. In accordance with the invention, the same dose of a prodrug of the invention provides a longer duration of therapeutic effect as compared to the parent drug. Thus if a single dose of the parent drug provides 12 hours of therapeutic effectiveness, a prodrug of that same parent drug in accordance with the invention that provides therapeutic effectiveness for greater than 12 hours will be considered to achieve a "sustained release".

The precise dose of a prodrug of the invention depends upon several factors including the nature and dose of the parent drug and the chemical characteristics of the prodrug moiety linked to the parent drug. Ultimately, the effective dose and dose frequency of a prodrug of the invention will be decided by the attending physician within the scope of sound medical judgment. The specific therapeutically effective dose level and dose frequency for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

EXAMPLES

STEP 1: Synthesis of 7-(4-(4-(2,3-dichlorophenyl)piperazin-1-yl)butoxy)-1-(hydroxymethyl)-3,4-dihydroquinolin-2(1H)-one

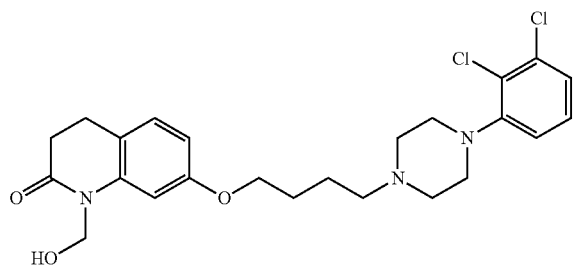 [SMILES: O=C1CCc2ccc(OCCCCN3CCN(c4cccc(Cl)c4Cl)CC3)cc2N1CO]

Procedure:

A mixture of Aripiprazole (5.2 g, 0.012 mol), triethylamine (0.25 mL, 0.0018 mol), 37% aqueous formaldehyde solution (18.5 mL) and dimethylformamide (50 mL) was heated at 80° C. for 48 hours. After 48 hours the reaction mixture was cooled to ambient temperature, diluted with ethyl acetate (200 mL) and washed with water (2×200 mL) and brine (2×200 mL). The organic phase was dried with sodium sulphate, filtered and concentrated in vacuo to give hemi-aminal as a white solid [5.6 g, containing 43% Aripiprazole and 56% hemi-aminal (as per LCMS analysis)].

Synthesis of Bis((7-(4-(4-(2,3-dichlorophenyl) piperazin-1-yl) butoxy)-2oxo-3,4-dihydroquinolin-1(2H)-yl) methyl) decanedioate

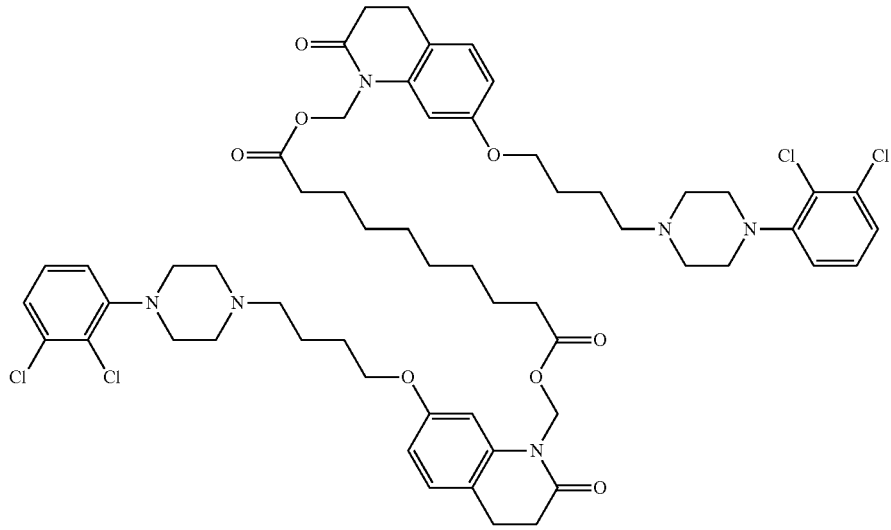 [SMILES: O=C(CCCCCCCCC(=O)OCN1C(=O)CCc2ccc(OCCCCN3CCN(c4cccc(Cl)c4Cl)CC3)cc21)OCN1C(=O)CCc2ccc(OCCCCN3CCN(c4cccc(Cl)c4Cl)CC3)cc21]

Procedure:

A solution of Step-1 reaction mixture (1.0 g, 0.0021 mol) in dichloromethane (20 mL) was stirred at 25° C. under nitrogen atmosphere. Triethylamine (1.45 mL, 0.0105 mol) was added drop wise to the above solution at 25° C. and the resulting reaction mixture was allowed to stir at the same temperature for next 10 minutes. After 10 minutes a solution of sebacoyl chloride in dichloromethane (0.223 mL, 0.00105 mol sebacoyl chloride in 2.2 mL dichloromethane) was added drop wise to the above reaction mixture at 25° C. The resulting clear reaction mixture was warmed to 45° C. whereby it was allowed to stir for next 2 hours. The reaction mixture was partitioned between dichloromethane (100 mL) and water (200 mL) and the aqueous layer was extracted with dichloromethane (2×100 mL). The combined organic fractions were washed with brine (100 mL), dried over sodium sulphate, filtered and concentrated in vacuo. The product was purified by flash chromatography using dichloromethane: methanol as mobile phase and the desired product eluted at around 1.5% methanol in dichloromethane to provide Compound-6 [0.3 g, 22% yield].

$^1$H NMR (DMSO, 400 MHz) δ 1.171 (s, 8H), 1.44-1.49 (m, 4H), 1.56-1.61 (m, 4H), 1.69-1.76 (m, 4H), 2.29 (t, 4H), 2.37 (t, 4H), 2.57 (t, 4H), 2.80 (t, 4H), 2.95 (broad s, 8H), 3.35 (broad s, 8H), 3.97 (t, 4H), 5.86 (broad s, 4H), 6.63-6.65 (m, 4H), 7.09-7.14 (m, 4H), 7.27-7.31 (m, 4H); m/z (M$^+$H) 1123.

Synthesis of Compound-7

Bis((7-(4-(4-(2,3-dichlorophenyl) piperazin-1-yl) butoxy)-2oxo-3,4-dihydroquinolin-1(2H)-yl) methyl) dodecanedioate Procedure:

A solution of Step-1 (1.0 g, 0.0021 mol) in dichloromethane (20 mL) was stirred at 25° C. under nitrogen atmosphere. Triethylamine (1.45 mL, 0.0105 mol) was added drop wise to the above solution at 25° C. and the resulting reaction mixture was allowed to stir at the same temperature for next 10 minutes. After 10 minutes a solution of dodecandioyl dichloride in dichloromethane (0.280 g, 0.00105 mol dodecandioyl dichloride in 2.5 mL dichloromethane) was added drop wise to the above reaction mixture at 25° C. The resulting clear reaction mixture was warmed to 45° C. whereby it was allowed to stir for next 2 hours. The reaction mixture was partitioned between dichloromethane (100 mL) and water (200 mL) and the aqueous layer was extracted with dichloromethane (2×100 mL). The combined organic were washed with brine (100 mL), dried over sodium sulphate, filtered and concentrated in vacuo. The product was purified by flash chromatography using dichloromethane: methanol as mobile phase and the desired product eluted at around 1.5% methanol in dichloromethane. Distillation of the product fractions provided Compound-7 [0.160 g, 11% yield].

$^1$H NMR (DMSO, 400 MHz) δ 1.16-1.18 (s, 12H), 1.47-1.50 (m, 4H), 1.57-1.62 (m, 4H), 1.71-1.75 (m, 4H), 2.28-2.32 (t, 4H), 2.38 (t, 4H), 2.57 (t, 4H), 2.80 (t, 4H), 2.95 (broad s, 8H), 3.34 (broad s, 8H), 3.97 (t, 4H), 5.86 (broad s, 4H), 6.63-6.65 (m, 4H), 7.10-7.15 (m, 4H), 7.28-7.31 (m, 4H); m/z (M$^+$H) 1149.7.

Synthesis of Compound-8

Synthesis of Tetradecandioyl Dichloride

Oxalyl chloride (1.35 mL, 0.015 mol) was added drop wise to a solution of Tetradecandioyl dichloride (1.0 g, 0.0039 mol) in dichloromethane at 25° C. After the addition was completed, the reaction mixture was stirred at same temperature for 2 hours, the reaction mixture was partitioned between dichloromethane (100 mL) and water (200 mL), the aqueous layer was extracted with dichloromethane (2×100 mL). The combined organic extracts were washed with brine (200 mL), dried over sodium sulphate filtered and concentrated in vacuo to provide the desired product (0.9 g, 90% yield) as a colorless liquid which was used directly for the next step without further purification.

Synthesis of Bis ((7-(4-(4-(2,3-dichlorophenyl) piperazin-1-yl) butoxy)-2oxo-3,4-dihydroquinolin-1 (2H)-yl) methyl) tetradecanedioate

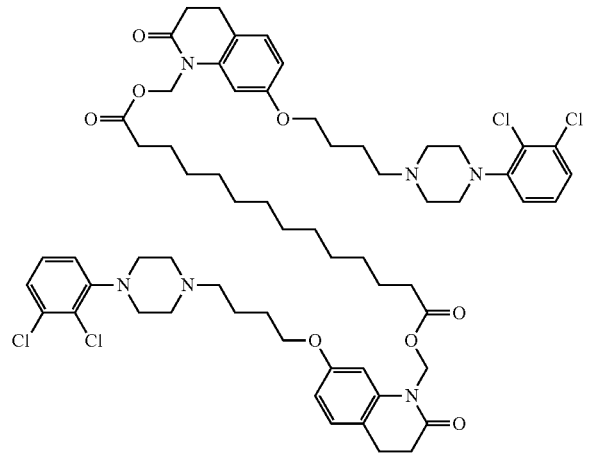 [SMILES: O=C(CCCCCCCCCCCCC(=O)OCN1C(=O)CCc2ccc(OCCCCN3CCN(c4cccc(Cl)c4Cl)CC3)cc21)OCN1C(=O)CCc2ccc(OCCCCN3CCN(c4cccc(Cl)c4Cl)CC3)cc21]

A solution of Step-1 (1.0 g, 0.0021 mol) in dichloromethane (20 mL) was stirred at 25° C. under nitrogen atmosphere. Triethylamine (1.45 mL, 0.0105 mol) was added drop wise to the above solution at 25° C. and the resulting reaction mixture was allowed to stir at the same temperature for next 10 minutes. After 10 minutes a solution of tetradecandioyl dichloride in dichloromethane (0.308 g, 0.00105 mol tetradecandioyl dichloride in 3.0 mL dichloromethane) was added drop wise to the above reaction mixture at 25° C. The resulting clear reaction mixture was warmed to 45° C. whereby it was allowed to stir for next 2 hours. The reaction mixture was partitioned between dichloromethane (100 mL) and water (200 mL) and the aqueous layer was extracted with dichloromethane (2×100 mL). The combined organic were washed with brine (200 mL), dried over sodium sulphate, filtered and concentrated in vacuo. The product was purified by flash chromatography using dichloromethane: methanol as mobile phase and the desired product eluted at around 1.8% methanol in dichloromethane to provide Compound-8 [0.170 g, 12% yield].

$^1$H NMR (DMSO, 400 MHz) δ 1.16-1.24 (m 18H), 1.47-1.51 (m, 4H), 1.57-1.62 (m, 4H), 1.70-1.75 (m, 4H), 2.30 (t, 4H), 2.38 (t, 4H), 2.57 (t, 4H), 2.80 (t, 4H), 2.96 (broad s, 8H), 3.34 (broad s, 8H), 3.97 (t, 4H), 5.86 (broad s, 4H), 6.654 (m, 4H), 7.10-7.15 (m, 4H), 7.27-7.31 (m, 4H); m/z (M$^+$H) 1177.9.

While this invention has been particularly shown and described with references to preferred embodiments thereof, it will be understood by those skilled in the art that various changes in form and details may be made therein without departing from the scope of the invention encompassed by the appended claims.

What is claimed:

1. A prodrug conjugate, having the formula:

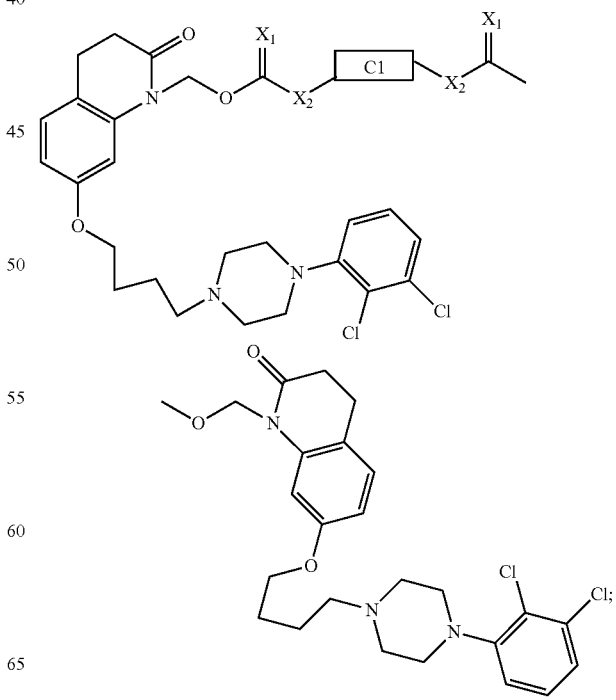

151
-continued
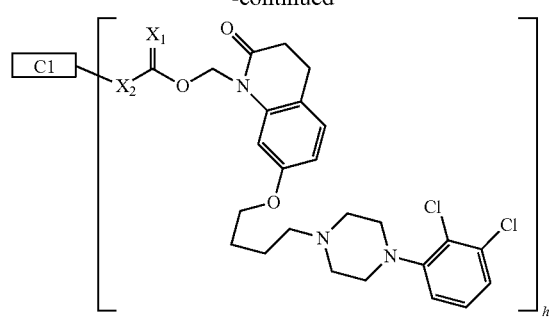
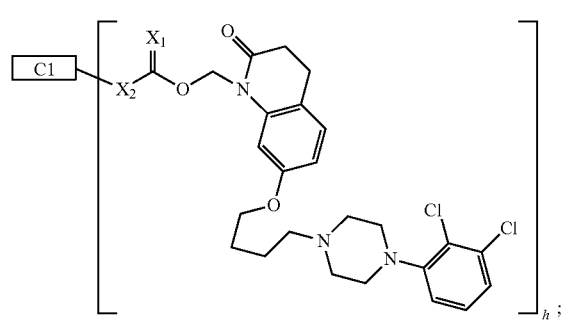
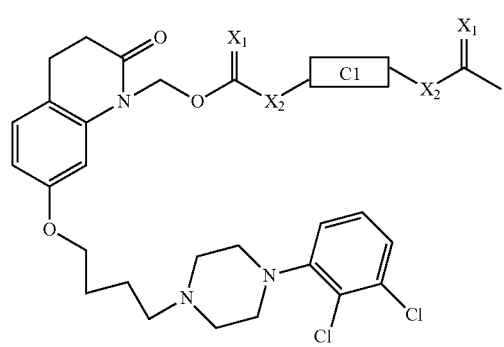
152
-continued
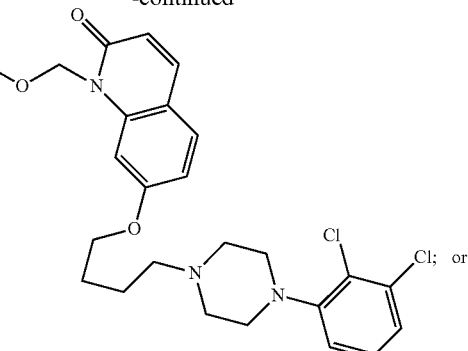
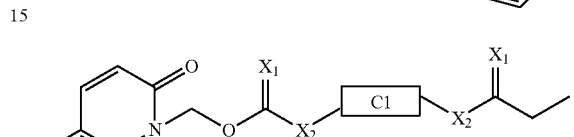
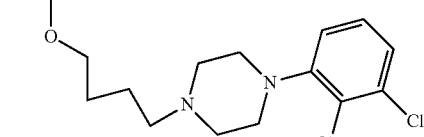
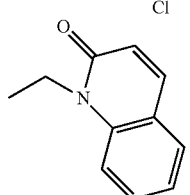
wherein
h is 3 or 4;
$X_1$ is O or S;
$R_{20}$ is selected from hydrogen, halogen, aliphatic, substituted aliphatic, aryl or substituted aryl;
C1 is a carrier moiety; and
$X_2$ is selected from direct bond, O, S or $NR_{20}$.
2. A prodrug conjugate having the formula:
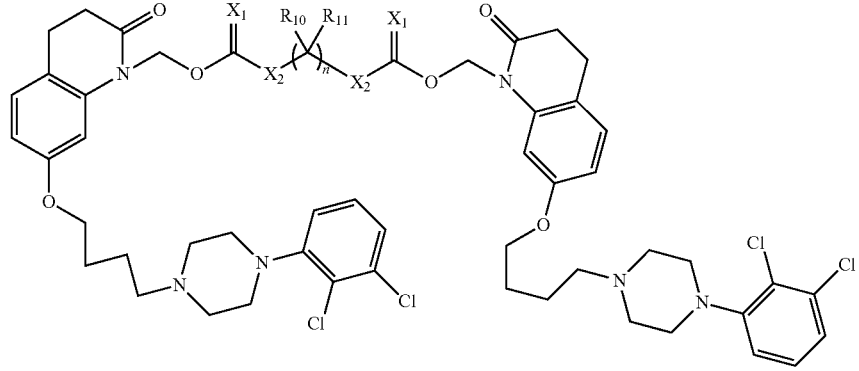

wherein n is selected from 4, 5, 6, 7, 8, 9, 10, 11, 12, 13, 14, 15, 16, 17, 18, 19, 20, 21, 22, 23, 24, 25, 26, 27, 28, 29 and 30;

each $R_{10}$ and $R_{11}$ is independently selected from hydrogen, halogen, —$OR_{20}$, —$SR_{20}$, —$NR_{20}R_{21}$, —$C(O)R_{20}$, —$C(O)OR_{20}$, —$C(O)NR_{20}R_{21}$, —$N(R_{20})C(O)R_{21}$, —$CF_3$, —CN, —$NO_2$, —$N_3$, acyl, optionally substituted alkoxy, optionally substituted alkylamino, optionally substituted dialkylamino, optionally substituted alkylthio, optionally substituted alkylsulfonyl, optionally substituted aliphatic, optionally substituted aryl or optionally substituted heterocyclyl;

alternatively two $R_{10}$ and $R_{11}$ together with the atoms to which they are attached may form an optionally substituted 3, 4, 5, 6 or 7 membered carbocyclic or heterocyclyl ring;

$X_1$ is O or S; and $X_2$ is selected from direct bond, O, S or $NR_{20}$;

wherein each $R_{20}$ and $R_{21}$ is selected from hydrogen, halogen, aliphatic, substituted aliphatic, aryl or substituted aryl.

3. A method for sustained delivery of a parent drug selected from aripiprazole and dehydroaripiprazole to a patient comprising administering to the patient a prodrug conjugate of claim 1, wherein upon administration to the patient, release of the parent drug from the prodrug is sustained.

4. A method for sustained delivery of a parent drug selected from aripiprazole and dehydroaripiprazole to a patient comprising administering to the patient a prodrug conjugate of claim 2, wherein upon administration to the patient, release of the parent drug from the prodrug is sustained.

5. A prodrug conjugate according to claim 1, selected from the group consisting of:

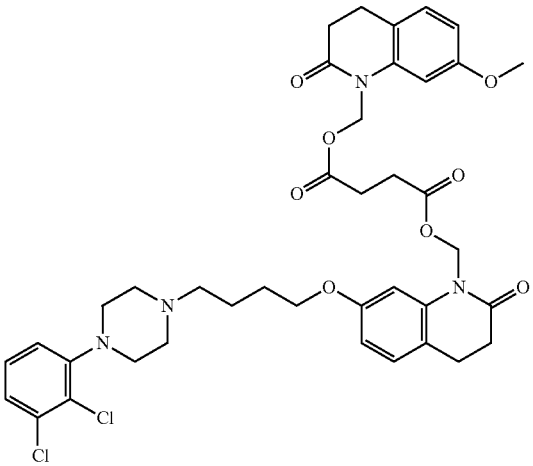

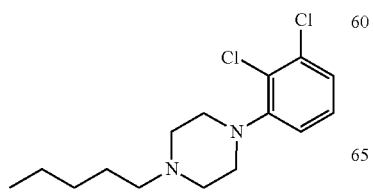

-continued

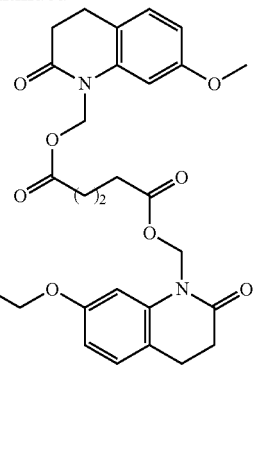

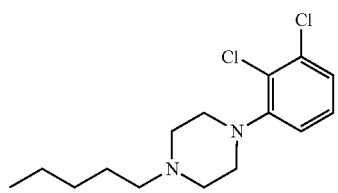

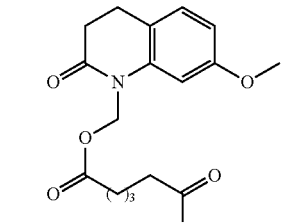

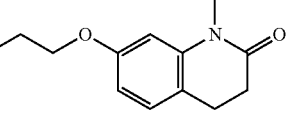

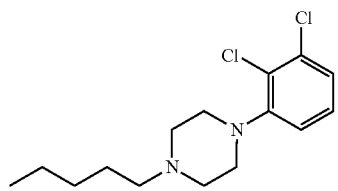

155
-continued
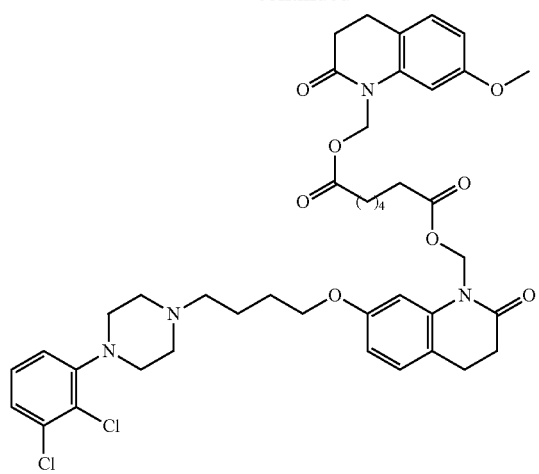
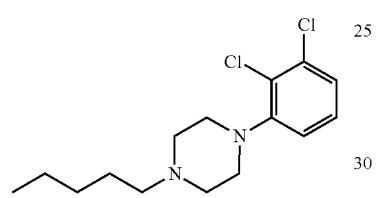
156
-continued
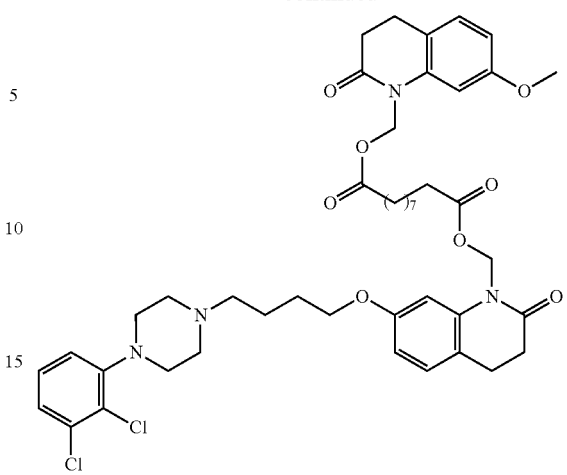
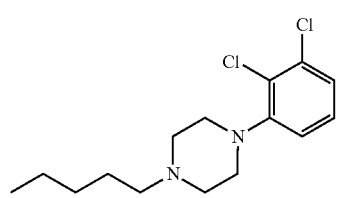
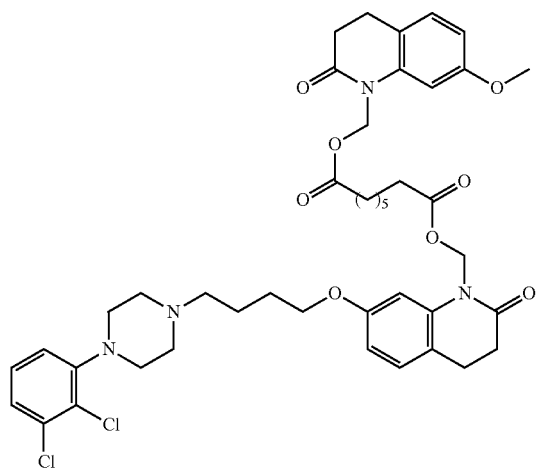
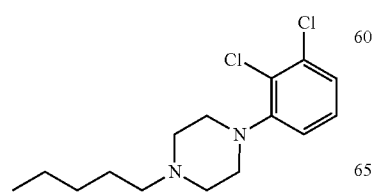
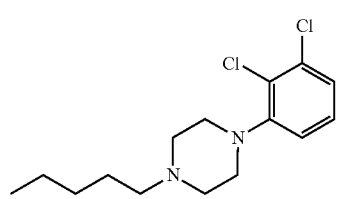

157
-continued
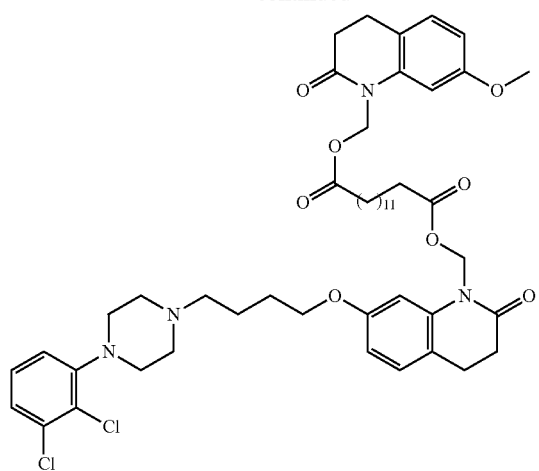
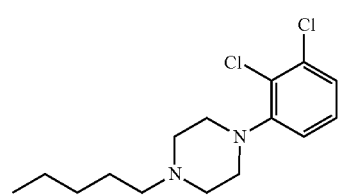
158
-continued
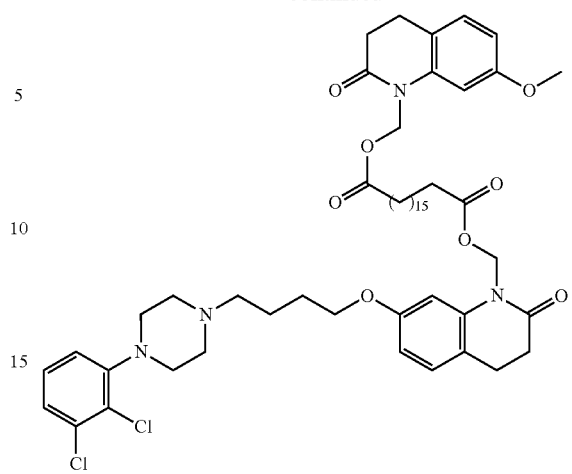
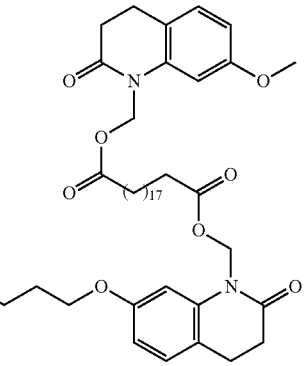
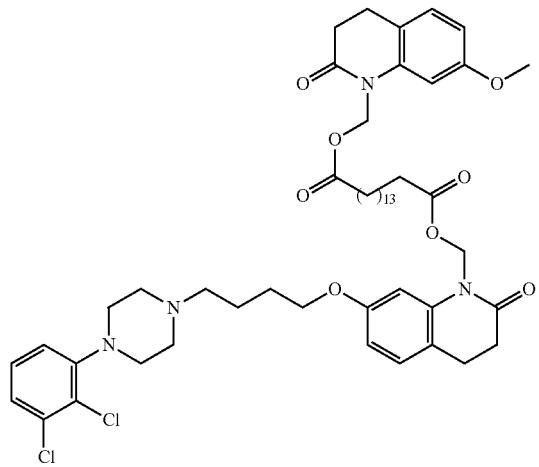
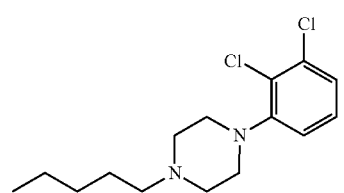
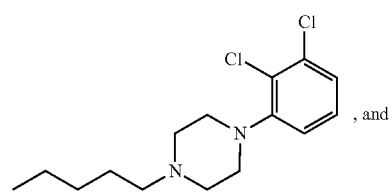

-continued
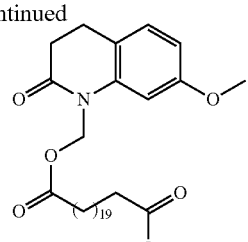
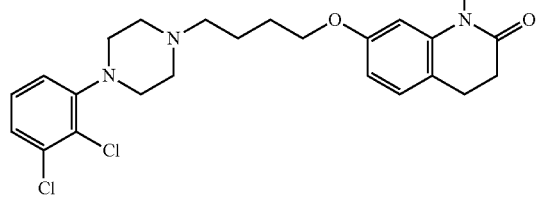
-continued
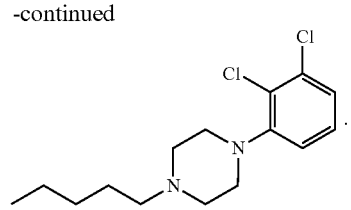
6. A method for sustained delivery of a parent drug selected from aripiprazole and dehydroaripiprazole to a patient comprising administering to the patient a prodrug conjugate of claim 5, wherein upon administration to the patient, release of the parent drug from the prodrug is sustained.
* * * * *

UNITED STATES PATENT AND TRADEMARK OFFICE
CERTIFICATE OF CORRECTION

PATENT NO. : 10,584,099 B2  Page 1 of 1
APPLICATION NO. : 15/864305
DATED : March 10, 2020
INVENTOR(S) : Tarek A. Zeidan and Laura Cook Blumberg It is certified that error appears in the above-identified patent and that said Letters Patent is hereby corrected as shown below:

In the Claims

At Column 152

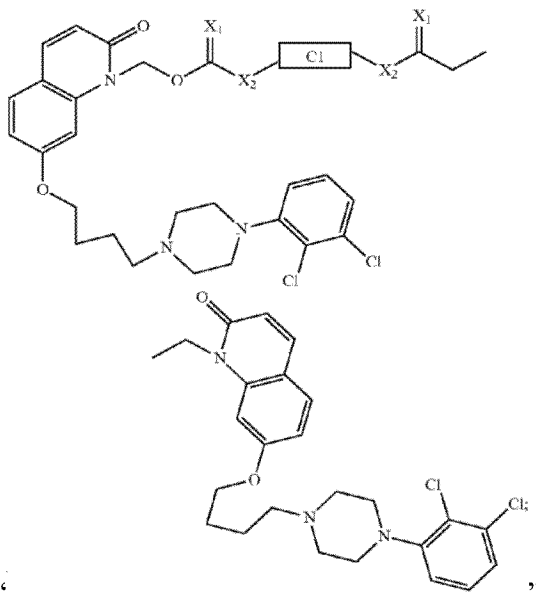

In Claim 1, at Lines 15-40 delete " " and insert

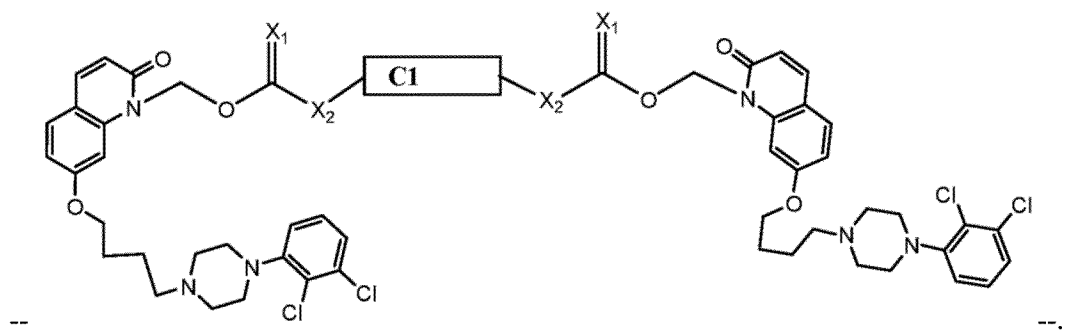

--  --.

Signed and Sealed this
Ninth Day of February, 2021

Drew Hirshfeld
*Performing the Functions and Duties of the
Under Secretary of Commerce for Intellectual Property and
Director of the United States Patent and Trademark Office*